US009937182B2

(12) United States Patent
Grobe et al.

(10) Patent No.: US 9,937,182 B2
(45) Date of Patent: Apr. 10, 2018

(54) THERAPEUTIC STRATEGIES FOR THE TREATMENT OF PREECLAMPSIA

(71) Applicant: UNIVERSITY OF IOWA RESEARCH FOUNDATION, Iowa City, IA (US)

(72) Inventors: Justin L. Grobe, Iowa City, IA (US); Mark K. Santillan, Iowa City, IA (US); Donna Ann Santillan, Iowa City, IA (US)

(*) Notice: Subject to any disclaimer, the term of this patent is extended or adjusted under 35 U.S.C. 154(b) by 0 days.

(21) Appl. No.: 14/766,574

(22) PCT Filed: Feb. 10, 2014

(86) PCT No.: PCT/US2014/015631
§ 371 (c)(1),
(2) Date: Aug. 7, 2015

(87) PCT Pub. No.: WO2014/124396
PCT Pub. Date: Aug. 14, 2014

(65) Prior Publication Data
US 2015/0374698 A1 Dec. 31, 2015

Related U.S. Application Data

(60) Provisional application No. 61/762,830, filed on Feb. 8, 2013, provisional application No. 61/762,831, filed on Feb. 8, 2013, provisional application No. 61/906,074, filed on Nov. 19, 2013.

(51) Int. Cl.
| | | |
|---|---|---|
| *A61K 31/55* | (2006.01) | |
| *A61K 31/495* | (2006.01) | |
| *A61K 31/44* | (2006.01) | |
| *A61K 31/519* | (2006.01) | |
| *G01N 33/543* | (2006.01) | |
| *G01N 33/68* | (2006.01) | |
| *A61K 31/404* | (2006.01) | |
| *A61K 45/06* | (2006.01) | |
| *A61K 38/11* | (2006.01) | |
| *A61K 31/444* | (2006.01) | |
| *A61K 31/498* | (2006.01) | |

(52) U.S. Cl.
CPC .......... *A61K 31/519* (2013.01); *A61K 31/404* (2013.01); *A61K 31/55* (2013.01); *A61K 38/11* (2013.01); *A61K 45/06* (2013.01); *C12Y 304/11003* (2013.01); *G01N 33/54386* (2013.01); *G01N 33/689* (2013.01); *A61K 31/444* (2013.01); *A61K 31/498* (2013.01); *G01N 2800/368* (2013.01)

(58) Field of Classification Search
CPC ..... A61K 31/55; A61K 31/498; A61K 31/444
USPC ....................... 514/215, 249, 334
See application file for complete search history.

(56) References Cited

U.S. PATENT DOCUMENTS

| | | |
|---|---|---|
| 5,733,787 A | 3/1998 | Messenger et al. |
| 6,210,971 B1 | 4/2001 | Messenger et al. |
| 2003/0121067 A1 | 6/2003 | Brennan et al. |
| 2007/0178530 A1 | 8/2007 | Poston et al. |
| 2007/0225333 A1 | 9/2007 | Bryans et al. |
| 2011/0251094 A1 | 10/2011 | Kas |
| 2011/0281880 A1 | 11/2011 | Oppenheimer et al. |
| 2012/0142559 A1 | 6/2012 | Tuytten et al. |

FOREIGN PATENT DOCUMENTS

| | | | |
|---|---|---|---|
| WO | WO2005075982 A2 | 8/2005 | |
| WO | WO 2005105779 A1 * | 11/2005 | .......... C07D 401/04 |
| WO | WO 2011143538 A1 * | 11/2011 | .......... A61K 31/737 |
| WO | WO2011157445 A1 | 12/2011 | |

OTHER PUBLICATIONS

Wrobel LJ, Dupre A, and Raggenbass M. Excitatory action of vasopressin in the brain of the rat: role of cAMP signaling. Neuroscience 172: 177-186, 2011.
Wu CS, Nohr EA, Bech BH, Vestergaard M, Catov JM, and Olsen J. Health of children born to mothers who had preeclampsia: a population-based cohort study. American journal of obstetrics and gynecology 201: 269.e261-269. e210, 2009.
Wu CS, Sun Y, Vestergaard M, Christensen J, Ness RB, Haggerty CL, and Olsen J. Preeclampsia and risk for epilepsy in offspring. Pediatrics 122: 1072-1078, 2008.
Yamamoto J, Yamane Y, Umeda Y, Yoshioka T, Nakai M, and Ikeda M. Cardiovascular hemodynamics and vasopressin blockade in DOCA-salt hypertensive rats. Hypertension 6: 397-407, 1984.
Yang CR, Phillips MI, and Renaud LP. Angiotensin II receptor activation depolarizes rat supraoptic neurons in vitro. The American journal of physiology 263: RI333-1338, 1992.
Yang J, Kamide K, Kokubo Y, Takiuchi S, Tanaka C, Banno M, Miwa Y, Yoshii M, Horio T, Okayama A, Tomoike H, Kawano Y, and Miyata T. Genetic variations of regulator of G-protein signaling 2 in hypertensive patients and in the general population. Journal of hypertension 23: 1497-1505, 2005.
Yang RH, Jin H, Wyss JM, and Oparil S. Depressor effect of blocking angiotensin subtype 1 receptors in anterior hypothalamus. Hypertension 19: 475-481, 1992.
Ye S, Zhong H, Duong VN, and Campese VM. Losartan reduces central and peripheral sympathetic nerve activity in a rat model of neurogenic hypertension. Hypertension 39: 1101-1106, 2002.
Zhang W, Anger T, Su J, Hao J, Xu X, Zhu M, Gach A, Cui L, Liao R, and Mende U. Selective loss of fine tuning of Gq/11 signaling by RGS2 protein exacerbates cardiomyocyte hypertrophy. The Journal of biological chemistry 281: 5811-5820, 2006.
Zhang X, Hense HW, Riegger GA, and Sehunkert H. Association of arginine vasopressin and arterial blood pressure in a population-based sample. Journal of hypertension 17: 319-324, 1999.
Zicha J, Kunes J, Lebl M, Pohlova I, Slaninova J, and Jelinek J. Antidiuretic and pressor actions of vasopressin in age-dependent DOCA-salt hypertension. The American journal of physiology 256: R138-145, 1989.

(Continued)

Primary Examiner — Kevin E Weddington
(74) Attorney, Agent, or Firm — McDonnell Boehnen Hulbert & Berghoff LLP

(57) ABSTRACT

Compositions and methods for treating preeclampsia in a subject in need thereof are disclosed.

12 Claims, 11 Drawing Sheets

(56) References Cited

OTHER PUBLICATIONS

Zimmerman MC, Lazartigues E, Sharma RV, and Davisson RL. Hypertension caused by angiotensin II infusion involves increased superoxide production in the central nervous system. Circulation research 95: 210-216, 2004.

Zulfikaroglu E, Islimye M, Tongue EA, Payasli A, Isman F, Var T, and Danisman N. Circulating levels of copeptin, a novel biomarker in pre-eclampsia. The journal of obstetrics and gynaecology research 37: 1198-1202, 2011.

International Search Report dated May 1, 2014 issued in connection with International Application No. PCT/US2014/015627, filed on Feb. 10, 2014, 6 pages.

International Search Report dated May 26, 2014 issued in connection with International Application No. PCT/US2014/015631, filed on Feb. 10, 2014, 5 pages.

Written Opinion of the International Searching Authority dated May 1, 2014 issued in connection with International Application No. PCT/US2014/015627, filed on Feb. 10, 2014, 6 pages.

Written Opinion of the International Searching Authority dated May 26, 2014 issued in connection with International Application No. PCT/US2014/015631, filed on Feb. 10, 2014, 6 pages.

Communication Pursuant to Rule 164(1) EPC dated Aug. 23, 2016 with Supplemental Partial European Search Report completed on Jul. 13, 2016, issued in connection with European Patent Application No. EP14749527, filed on Feb. 10, 2014, 6 pages.

"Copeptin (CPP) Elisa Kit," Antibodies online commercial site, Retrieved from the Internet: <http://www.antibodies-online.com/kit/365068/Copeptin+CPP+ELISA/> retrieved Jul. 13, 2016.

Landau, R., et al., "Alteration of circulating placental leucine aminopeptidase (P-LAP) activity in preeclampsia," Neuroendocrinol Lett 2010; 31(1):63-66.

Koshimizu TA, Nasa Y, Tanoue A, Oikawa R, Kawahara Y, Kiyono Y, Adachi T, Tanaka T, Kuwaki T, Mori T, Takeo S, Okamura H, and Tsujimoto G. V1a vasopressin receptors maintain normal blood pressure by regulating circulating blood volume and baroreflex sensitivity. Proceedings of the National Academy of Sciences of the United States of America 103: 7807-7812, 2006.

Kubo T, Yamaguchi H, Tsujimura M, Hagiwara Y, and Fukumori R. An angiotensin system in the anterior hypothalamic area anterior is involved in the maintenance of hypertension in spontaneously hypertensive rats. Brain research bulletin 52: 291-296, 2000.

Kubo T, Yamaguchi H, Tsujimura M, Hagiwara Y, and Fukumori R. Blockade of angiotensin receptors in the anterior hypothalamic preoptic area lowers blood pressure in DOCA-salt hypertensive rats. Hypertension research : official Journal of the Japanese Society of Hypertension 23: 109-118, 2000.

Laragh JH. Biochemical profiling and the natural history of hypertensive diseases: low-renin essential hypertension, a benign condition. Circulation 44: 971-974, 1971.

Levine RJ, Lam C, Qian C, Yu KF, Maynard SE, Sachs BP, Sibai BM, Epstein FH, Romero R, Thadhani R, and Karumanchi SA. Soluble endoglin and other circulating antiangiogenic factors in preeclampsia. The New England journal of medicine 355: 992-1005, 2006.

Littlejohn NK, Siel RB, Jr., Ketsawatsomkron P, Pelham CJ, Pearson NA, Hilzendeger AM, Buehrer BA, Weidemann BJ, Li H, Davis DR, Thompson AP, Liu X, Cassell MD, Sigmund CD, and Grobe JL. Hypertension in mice with transgenic activation of the brain renin-angiotensin system is vasopressin dependent. American journal of physiology Regulatory, integrative and comparative physiology 304: R818-828, 2013.

Livak KJ and Schmittgen TD. Analysis of relative gene expression data usmg real-time quantitative PCR and the 2(-Delta Delta C(T)) Method. Methods (San Diego, Calif) 25: 402-408, 2001.

Lykke JA, Langhoff-Roos J, Sibai BM, Funai EF, Triche EW, and Paidas MJ. Hypertensive pregnancy disorders and subsequent cardiovascular morbidity and type 2 diabetes mellitus in the mother. Hypertension 53: 944-951, 2009.

Magnussen EB, Vatten LJ, Smith GD, and Romundstad PR. Hypertensive disorders in pregnancy and subsequently measured cardiovascular risk factors. Obstetrics and gynecology 114: 961-970, 2009.

Matsuguchi Hand Schmid PG. Acute interaction of vasopressin and neurogenic mechanisms in DOC-salt hypertension. The American journal of physiology 242: H37-43, 1982.

Mattsson R, Sulila P, Bernadotte F, and Mattsson A. Allopregnancy in B-cell deprived C57/BL mice—an investigation focusing on the relationship between survival of the fetuses and anti-paternal immune activity of the mothers. Developmental and comparative immunology 12: 167-176, 1988.

Mayorov DN and Head GA. AT1 receptors in the RVLM mediate pressor responses to emotional stress in rabbits. Hypertension 41: 1168-1173, 2003.

Mohring J and Mohring B. Reevaluation of DOCA escape phenomenon. The American journal of physiology 223: 1237-1245, 1972.

Morgenthaler N G, Struck J, Alonso C and Bergmann A. Assay for the Measurement of Copeptin, a Stable Peptide Derived from the Precursor of Vasopressin. Clinical Chemistry 52:1, 112-119, 2006.

Morimoto S, Cassell MD, and Sigmund CD. The brain renin-angiotensin system in transgenic mice carrying a highly regulated human renin transgene. Circulation research 90: 80-86, 2002.

Neves MF, Virdis A, and Schiffrin EL. Resistance artery mechanics and composition m angiotensin II-infused rats: effects of aldosterone antagonism. Journal of hypertension 21: 189-198, 2003.

Northcott CA, Watts S, Chen Y, Morris M, Chen A, and Haywood Jr. Adenoviral inhibition of AT1a receptors in the paraventricular nucleus inhibits acute increases in mean arterial blood pressure in the rat. American journal of physiology Regulatory, integrative and comparative physiology 299: R1202-1211, 2010.

Odibo AO, Rada CC, Cahill AG, Goetzinger KR, Tuuli MG, Odibo L, Macones GA, and England SK. First-trimester serum soluble fins-like tyrosine kinase-1, free vascular endothelial growth factor, placental growth factor and uterine artery Doppler in preeclampsia. Journal of perinatology : official journal of the California Perinatal Association 33: 370-674, 2013.

Oparil S, Yang RH, Jin HG, Chen SJ, Meng QC, Berecek KH, and Wyss JM. Role of anterior hypothalamic angiotensin II in the pathogenesis of salt sensitive hypertension in the spontaneously hypertensive rat. The American journal of the medical sciences 307 Suppll: S26-37, 1994.

Os I, Kjeldsen SE, Skjoto J, Westheim A, Lande K, Aakesson I, Frederichsen P, Leren P, Hjermann I, and Eide IK. Increased plasma vasopressin in low renin essential hypertension. Hypertension 8: 506-513, 1986.

Padfield PL, Brown JJ, Lever AF, Morton JJ, and Robertson JI. Blood pressure in acute and chronic vasopressin axcess: studies of malignant hypertension and the syndrome of inappropriate antidiuretic hormone secretion. The New England journal of medicine 304: 1067-1070, 1981.

Papageorghiou AT, To MS, Yu CK, and Nicolaides KH. Repeatability of measurement ofuterine artery pulsatility index using transvaginal color Doppler. Ultrasound in obstetrics & gynecology : the official journal of the International Society of Ultrasound in Obstetrics and Gynecology 18: 456-459, 2001.

Park CG and Leenen FH. Effects of centrally administered losartan on deoxycorticosterone-salt hypertension rats. Journal of Korean medical science 16: 553-557, 2001.

Phillips MI. Angiotensin in the brain. Neuroendocrinology 25: 354-377, 1978.

Poon LC, Kametas NA, Chelemen T, Leal A, and Nicolaides KH. Maternal risk factors for hypertensive disorders in pregnancy: a multivariate approach. Journal of human hypertension 24: 104-110, 2010.

Poon LC, Karagiannis G, Leal A, Romero XC, and Nicolaides KH. Hypertensive disorders in pregnancy: screening by uterine artery Doppler imaging and blood pressure at 11-13 weeks. Ultrasound in obstetrics & gynecology : the official journal of the International Society of Ultrasound in Obstetrics and Gynecology 34: 497-502, 2009.

(56) References Cited

OTHER PUBLICATIONS

Ramsay DS. Effects of circulating angiotensin II on the brain. In: Frontiers in Neuroendocrinology, edited by Ganong WF and Martini L. New York: Raven, 1982, p. 263-285.
Robben J.H., Knoers N.V.A.M., and Deen P.M.T. Regulation of the Vasopressin V2 Receptor by Vasopressin in Polarized Renal Collecting Duct Cells. Molecular Biology of the Cell, vol. 15, 5693-5699, Dec. 2004.
Romero R, Mazor M, and Tartakovsky B. Systemic administration of interleukin-1 induces preterm parturition in mice. American journal of obstetrics and gynecology 165: 969-971, 1991.
Russell JA and Walley KR. Vasopressin and its immune effects in septic shock. Journal of innate immunity 2: 446-460, 2010.
Sakai K, Agassandian K, Morimoto S, Sinnayah P, Cassell MD, Davisson RL, and Sigmund CD. Local production of angiotensin II in the subfornical organ causes elevated drinking. The Journal of clinical investigation 117: 1088-1095, 2007.
Salim S, Sinnarajah S, Kehrl JH, and Dessauer CW. Identification ofRGS2 and type V adenylyl cyclase interaction sites. The Journal of biological chemistry 278: 15842-15849, 2003.
Santillan MK, Santillan DA, Sigmund CD, and Hunter SK. From molecules to medicine: a future cure for preeclampsia? Drug news & perspectives 22: 531-541, 2009.
Schinke M, Baltatu 0, Bohm M, Peters J, Rascher W, Bricca G, Lippoldt A, Ganten D, and Bader M. Blood pressure reduction and diabetes insipidus in transgenic rats deficient in brain angiotensinogen. Proceedings of the National Academy of Sciences of the United States of America 96: 3975-3980, 1999.
Semplicini A, Lenzini L, Sartori M, Papparella I, Cabo LA, Pagnin E, Strapazzon G, Benna C, Costa R, Avogaro A, Ceolotto G, and Pessina AC. Reduced expression of regulator of G-protein signaling 2 (RGS2) in hypertensive patients Increases calcium mobilization and ERKI/2 phosphorylation induced by angiotensin II. Journal of hypertension 24: 1115-1124, 2006.
Shah DM. The role of RAS in the pathogenesis of preeclampsia. Current hypertension reports 8: 144-152, 2006.
Shi P, Diez-Freire C, Jun JY, Qi Y, Katovich MJ, Li Q, Sriramula S, Francis J, Sumners C, and Raizada MK. Brain microglial cytokines in neurogenic hypertension. Hypertension 56: 297-303, 2010.
Siljee JE, Wortelboer EJ, Koster MP, Imholz S, Rodenburg W, Visser GH, de Vries A, Schielen PC, and Pennings JL. Identification of interleukin-1 beta, but no other inflammatory proteins, as an early onset pre-eclampsia biomarker in first trimester serum by bead-based multiplexed immunoassays. Prenatal diagnosis 33: 1183-1188, 2013.
Sinn PL, Zhang X, and Sigmund CD. JG cell expression and partial regulation of a human renin genomic transgene driven by a minimal renin promoter. The American journal of physiology 277: F634-642, 1999.
Steegers EA, von Dadelszen P, Duvekot JJ, and Pijnenborg R. Pre-eclampsia. Lancet 376: 631-644, 2010.
Sulila P, Holmdahl R, Hansson I, Bernadotte F, Mattsson A, and Mattsson R. An investigation of allogeneic pregnancy in multiparous mice subjected to in vivo depletion of CD8 (Ly2)-positive lymphocytes by monoclonal antibody treatment. Journal of reproductive immunology 14: 235-245, 1988.
Sun X, Kaltenbronn KM, Steinberg TH, and Blumer KJ. RGS2 is a mediator of nitric oxide action on blood pressure and vasoconstrictor signaling. Molecular pharmacology 67: 631-639, 2005.
Sun Z, Cade R, and Morales C. Role of central angiotensin II receptors in cold-induced hypertension. American journal of hypertension 15: 85-92, 2002.
Szczepanska-Sadowska E, Paczwa P, Lon S, and Ganten D. Increased pressor function of central vasopressinergic system in hypertensive renin transgenic rats. Journal of hypertension 16: 1505-1514, 1998.
Szinnai G, Morgenthaler NG, Berneis K, Struck J, Muller B, Keller U, and Christ-Crain M. Changes in plasma copeptin, the c-terminal portion of arginine vasopressin during water deprivation and excess in healthy subjects. The Journal of clinical endocrinology and metabolism 92: 3973-3978, 2007.
Takimoto E, Koitabashi N, Hsu S, Ketner EA, Zhang M, Nagayama T, Bedja D, Gabrielson KL, Blanton R, Siderovski DP, Mendelsohn ME, and Kass DA. Regulator of G protein signaling 2 mediates cardiac compensation to pressure overload and antihypertrophic effects of PDE5 inhibition in mice. The Journal of clinical investigation 119: 408-420, 2009.
Tang KM, Wang GR, Lu P, Karas RH, Aronovitz M, Heximer SP, Kaltenbronn KM, Blumer KJ, Siderovski DP, Zhu Y, and Mendelsohn ME. Regulator of G-protein signaling-2 mediates vascular smooth muscle relaxation and blood pressure. Nature medicine 9: 1506-1512, 2003.
Thadhani R, Kisner T, Hagmann H, Bossung V, Noack S, Schaarschmidt W, JankA, Kribs A, Cornely OA, Kreyssig C, Hemphill L, Rigby AC, Khedkar S, Lindner TH, Mallmann P, Stepan H, Karumanchi SA, and Benzing T. Pilot study of extracorporeal removal of soluble fms-like tyrosine kinase 1 in preeclampsia. Circulation 124: 940-950, 2011.
Trinder D, Phillips PA, Stephenson JM, Risvanis J, Aminian A, Adam W, Cooper M, and Johnston CI. Vasopressin VI and V2 receptors in diabetes mellitus. The American journal of physiology 266: E217-223, 1994.
Tsang S, Woo AY, Zhu W, and Xiao RP. Deregulation of RGS2 in cardiovascular diseases. Frontiers in bioscience (Scholar edition) 2: 547-557,2010.
ACOG practice bulletin. Diagnosis and management of preeclampsia and eclampsia. No. 33, Jan. 2002. Obstetrics and gynecology 99: 159-167, 2002.
Aoyagi T, Koshimizu TA, and Tanoue A. Vasopressin regulation of blood pressure and volume: findings from V1a receptor-deficient mice. Kidney international 76: 1035-1039, 2009.
Argent NB, Burrell LM, Goodship TH, Wilkinson R, and Baylis PH. Osmoregulation of thirst and vasopressin release in severe chronic renal failure. Kidney international 39: 295-300, 1991.
Bakris G, Bursztyn M, Gavras I, Bresnahan M, and Gavras H. Role of vasopressin in essential hypertension: racial differences. Journal of hypertension 15: 545-550, 1997.
Balanescu S, Kopp P, Gaskill MB, Morgenthaler NG, Schindler C, and Rutishauser J. Correlation of plasma copeptin and vasopressin concentrations in hypo-, iso-, and hyperosmolar States. The Journal of clinical endocrinology and metabolism 96: 1046-1052, 2011.
Bonjour JP and Malvin RL. Stimulation of ADH release by the renin-angiotensin system. The Americanjournal of physiology 218: 1555-1559, 1970.
Burnatowska-Hledin M, Zeneberg A, Roulo A, Grobe J, Zhao P, Lelkes PI, Clare P, and Barney C. Expression of VACM-1 protein in cultured rat adrenal endothelial cells is linked to the cell cycle. Endothelium: journal of endothelial cell research 8: 49-63, 2001.
Burnatowska-Hledin M, Zhao P, Capps B, Poel A, Parmelee K, Mungall C, Sharangpani A, and Listenberger L. VACM-1, a cullin gene family member, regulates cellular signaling. American journal of physiology Cell physiology 279: C266-273, 2000.
Burrell LM, Risvanis J, Johnston CI, Naitoh M, and Balding LC. Vasopressin receptor antagonism—a therapeutic option in heart failure and hypertension. Experimental physiology 85 Spec No. 259s-265s, 2000.
Calo LA, Pagnin E, Davis PA, Sartori M, Ceolotto G, Pessina AC, and Semplicini A. Increased expression of regulator of G protein signaling-2 (RGS-2) in Bartter's/Gitelman's syndrome. A role in the control of vascular tone and implication or hypertension. The Journal of clinical endocrinology and metabolism 89: 4153-4157, 2004.
Campos LA, Couto AS, Iliescu R, Santos JA, Santos RA, Ganten D, Campagnole-Santos MJ, Bader M, and Baltatu 0. Differential regulation of central vasopressin receptors in transgenic rats with low brain angiotensinogen. Regulatory peptides 119: 177-182, 2004.
Chikanza IC, Petrou P, and Chrousos G. Perturbations of arginine vasopressin secretion during inflammatory stress. Pathophysiologic implications. Annals of the New York Academy of Sciences 917:825-834, 2000.

(56) References Cited

OTHER PUBLICATIONS

Ciosek J and Guzek JW. (6R)-5,6,7,8-tetrahydro-alpha-biopterin affects vasopressin and oxytocin release from rat neurointermediate lobe in vitro. Experimental and clinical endocrinology 95: 287-291, 1990.

Ciosek J, Guzek JW, and Orlowska-Majdak M. Neurohypophysial vasopressin and oxytocin as influenced by (6R)-5,6,7,8-tetrahydro-alpha-biopterin in euhydrated and dehydrated rats. Biological chemistry Hoppe-Seyler 373: 1079-1083, 1992.

Coleman CG, Anrather J, Iadecola C, and Pickel VM. Angiotensin II type 2 receptors have a major somatodendritic distribution in vasopressin-containing neurons in the mouse hypothalamic paraventricular nucleus. Neuroscience 163: 129-142, 2009.

Crofton JT, Share L, Shade RE, Lee-Kwon WJ, Manning M, and Sawyer WH. The importance of vasopressin in the development and maintenance of DOC-salt hypertension in the rat Hypertension 1:31-38, 1979.

D'Antonio F, Rijo C, Thilaganathan B, Akolekar R, Khalil A, Papageourgiou A, and Bhide A. Association between first-trimester maternal serum pregnancy-associated plasma protein-A and obstetric complications. Prenatal diagnosis 33: 339-847, 2013.

da Silva AQ, Fontes MA, and Kanagy NL. Chronic infusion of angiotensin receptor antagonists in the hypothalamic Paraventricular nucleus prevents hypertension in a rat model of sleep apnea. Brain research 1368: 231-238, 2011.

Davisson RL, Yang G, Beltz TG, Cassell MD, Johnson AK, and Sigmund CD. The brain renin- angiotensin system contributes to the hypertension in mice containing both the human renin and human angiotensinogen transgenes. Circulation research 83: 1047-1058, 1998.

de Oliveira-Sales EB, Nishi EE, Boim MA, Dolnikoff MS, Bergamaschi CT, and Campos RR. Upregulation of ATIR and iNOS in the rostral ventrolateral medulla (RVLM) is essential for the sympathetic hyperactivity and hypertension in the 2K-1C Wistar rat model. American journal of hypertension 23: 708-715, 2010.

de Paula RB, Plavnik FL, Rodrigues CI, Neves Fde A, Kohlmann 0, Jr., Ribeiro AB, Gavras I, and Gavras H. Contribution of vasopressin to orthostatic blood pressure maintenance in essential hypertension. American journal of hypertension 6: 794-798, 1993.

Dubovsky JA, Albertini MR and McNeel DG. (2007) "MAD-CT-2 identified as a novel melanoma cancer-testis antigen using phage immunoblot analysis." J. Immunotherapy 30:675-683.

Fay MJ, Du J, Yu X, and North WG. Evidence for expression of vasopressin V2 receptor mRNA in human lung. Peptides 17: 477-481, 1996.

Foda AA and Abdel Aal IA. Maternal and neonatal copeptin levels at cesarean section and vaginal delivery. European journal of obstetrics, gynecology, and reproductive biology 165: 215-218, 2012.

Gagnon DJ, Cousineau D, and Boucher PJ. Release of vasopressin by angiotensin II and prostaglandin E2 from the rat neurohypophysis in vitro. Life sciences 12: 487-497, 1973.

Garovic VD and Hayman Sr. Hypertension in pregnancy: an emerging risk factor for cardiovascular disease. Nature clinical practice Nephrology 3: 613-622, 2007.

Gassanov N, Semmo N, Semmo M, Nia AM, Fuhr U, and Er F. Arginine vasopressin (AVP) and treatment with arginine vasopressin receptor antagonists (vaptans) in congestive heart failure, liver cirrhosis and syndrome of inappropriate antidiuretic hormone secretion (SIADH). European journal of clinical pharmacology 67: 333-346, 2011.

Gavras H. Pressor systems in hypertension and congestive heart failure. Role of vasopressin. Hypertension 16: 587-593, 1990.

Gendron RL, Nestel FP, Lapp WS, and Baines MG. Lipopolysaccharide-induced fetal resorption in mice is associated with the intrauterine production of tumour necrosis factor-alpha. Journal of reproduction and fertility 90: 395-402, 1990.

Gozdz A, Szczepanska-Sadowska E, Szczepanska K, Maslinski W, and Luszczyk B. Vasopressin V1a, V1b and V2 receptors mRNA in the kidney and heart of the renin transgenic TGR(mRen2)27 and Sprague Dawley rats. Journal of physiology and pharmacology: an official journal of the Polish Physiological Society 53: 349-357, 2002.

Greenberg A and Verbalis JG. Vasopressin receptor antagonists. Kidney International (2006) 69, 2124-2130.

Grobe JL, Grobe CL, Beltz TG, Westphal Sg, Morgan DA, Xu D, de Lange WJ, Li H, Sakai K, Thedens DR, Cassis LA, Rahmouni K, Mark AL, Johnson AK, and Sigmund CD. The brain Renin-angiotensin system controls divergent efferent mechanisms to regulate fluid and energy balance. Cell metabolism 12:431-442, 2010.

Grobe JL, Xu D, and Sigmund CD. An intracellular renin-angiotensin system in neurons: fact, hypothesis, or fantasy. Physiology (Bethesda, Md) 23: 187-193, 2008.

Gu S, Anton A, Salim S. Blumer KJ, Dessauer CW, and Heximer SP. Alternative translation initiation of human regulators of G-protein signaling-2 yields a set of functionally distinct proteins. Molecular pharmacology 73: 1-11, 2008.

Halabi CM, Beyer AM, de Lange WJ, Keen HL, Baumbach GL, Faraci FM, and Sigmund CD. Interference with PPAR gamma function in smooth muscle causes vascular dysfunction and hypertension. Cell metabolism 7: 215-226, 2008.

Hao J, Michalek C, Zhang W, Zhu M, Xu X, and Mende U. Regulation of cardiomyocyte signaling by RGS proteins: differential selectivity towards G proteins and susceptibility to regulation. Journal of molecular and cellular cardiology 41: 51-61, 2006.

Head GA and Mayorov DN. Central angiotensin and baroreceptor control of circulation. Annals of the New York of Sciences 940: 361-379, 2001.

Herse F, Dechend R, Harsem NK, Wallukat G, Janke J, Qadri F, Hering L, Muller DN, Luff FC, and Staff AC. Dysregulation of the circulating and tissue-based renin-angiotensin system in preeclampsia. Hypertension 49: 604-611, 2007.

Xeximer SP, Knutsen RH, Sun X, Kaltenbronn KM, Rhee MH, Peng N, Oliveira-dos-Santos A, Penninger JM, Muslin AJ, Steinberg TH, Wyss JM, Mecham RP, and Blumer KJ. Hypertension and prolonged vasoconstrictor signaling in RGS2-deficient mice. The Journal of clinical investigation 111: 445-452, 2003.

Heximer SP, Watson N, Linder ME, Blumer KJ, and Hepler JR. RGS2/GOS8 is a selective inhibitor of Gqalpha function. Proceedings of the National Academy of Sciences of the United States of America 94: 14389-14393, 1997.

Huang BS and Leenen FH. Both brain angiotensin II and "ouabain" contribute to sympathoexcitation and hypertension in Dahl S rats on high salt intake. Hypertension 32: 1028-1033, 1998.

Iovino M and Steardo L. Vasopressin release to central and peripheral angiotensin II in rats with lesions of the subfornical organ. Brain research 322: 365-368, 1984.

Itaya Y, Suzuki H, Matsukawa S, Kondo K, and Saruta T. Central renin-angiotensin system and the pathogenesis of DOCA-salt hypertension in rats. The American journal of physiology 251: H261-268, 1986.

Johren 0, Imboden H, Hauser W, Maye I, Sanvitto GL, and Saavedra JM. Localization of angiotensin-converting enzyme, angiotensin II, angiotensin II receptor subtypes, and vasopressin in the mouse hypothalamus. Brain research 157: 218-227, 1997.

Kajantie E, Eriksson JG, Osmond C, Thornburg K, and Barker DJ. Pre-eclampsia is associated with increased risk of stroke in the adult offspring: The Helsinki birth cohort study. Stroke; a journal of cerebral circulation 40: 1176-1180, 2009.

Karahasanovic A, Sorensen S, and Nilas L. First trimester pregnancy-associated plasma protein A and human chorionic gonadotropin-beta in early and late pre-eclampsia. Clin Chem Lab Med 2014; 52(4): 521-525.

Kashanian M, Aghbali F, and Mahali N. Evaluation of the diagnostic value of the first-trimester maternal serum high-sensitivity C-reactive protein level for prediction of pre-eclampsia. The journal of obstetrics and gynaecology research 39: 1549-1554, 2013.

Kato Y, Igarashi N, Hirasawa A, Tsujimoto G, and Kobayashi M. Distribution and developmental changes in vasopressin V2 receptor mRNA in rat brain. Differentiation; research in biological diversity 59: 163-169, 1995.

Kleinrouweler CE, Wiegerinck MM, Ris-Stalpers C, Bossuyt PM, van der Post JA, von Dadelszen P, Mol BW, and Pajkrt E. Accuracy

(56) References Cited

OTHER PUBLICATIONS of circulating placental growth factor, vascular endothelial growth factor, soluble fins-like tyrosine kinase 1 and soluble endoglin in the prediction of pre-eclampsia: a systematic review and meta-analysis. BJOG: an International journal of obstetrics and gynaecology 119:778-787,2012.
Knepel W, Nutto D, and Meyer DK. Effect of transection of subfornical organ efferent projections on vasopressin release induced by angiotensin or isoprenaline in the rat. Brain research 248: 180-184, 1982.
Office Action dated May 25, 2017, issued in connection with U.S. Appl. No. 14/766,528, filed Aug. 7, 2015, 10 pages.

\* cited by examiner

THERAPEUTIC STRATEGIES FOR THE TREATMENT OF PREECLAMPSIA

CROSS REFERENCE TO RELATED APPLICATIONS

This application is a U.S. National Phase of International Application No. PCT/US2014/015631, filed Feb. 10, 2014, which claims priority to U.S. Provisional Application No. 61/762,830, filed Feb. 8, 2013; U.S. Provisional Application No. 61/762,831, filed Feb. 8, 2013; and U.S. Provisional Application No. 61/906,074 filed Nov. 19, 2013, the disclosures of which are hereby incorporated by reference in their entireties.

BACKGROUND OF THE INVENTION

Hypertension complicates up to 10% of all pregnancies worldwide. In the United States, preeclampsia affects 5-7% of all pregnancies, approximately 300,000 pregnancies a year. Yet, it disproportionately represents 15% of all maternal-fetal morbidity and mortality. Preeclampsia is known to cause immediate maternal-fetal morbidities such as growth restriction, oligohydramnios, fetal death, maternal seizures, stroke, cerebrovascular hemorrhage, and maternal death (78). Mothers with a history of preeclampsia are at increased risk of future cardiac disease including myocardial infarction and stroke (24, 55, 56). Children born from preeclamptic pregnancies are also at increased risk of stroke (42), epilepsy (98), and metabolic, nutritional and blood disease (97) in later childhood or as an adult. Clearly, preeclampsia has immediate and long term effects on both the fetus and mother. However, its pathogenesis is poorly understood. Consequently, preventative, therapeutic, and curative modalities for preeclampsia are elusive. The only true cure for preeclampsia is the delivery of the fetus and dysfunctional placenta. This delivery is often preterm and contributes to additional morbidity and mortality (78). This fact emphasizes the importance of finding appropriate unifying pathways to be able to treat preeclampsia.

The neurohypophysial hormone, arginine vasopressin (AVP; FIG. 1), is a known regulator of blood pressure and composition in human and animal models. AVP is a major player in blood pressure control in selected populations including African Americans (4), the elderly (21), and in patients with congestive heart (26) or renal failure (3). This hormone appears to specifically be causative in patients with low-renin hypertension (81), which makes up a larger portion of the human essential hypertensive population (27%) than high-renin hypertension (16%) (51). However, whether AVP has a causative role in established preeclampsia has previously been unclear. Establishing such a role for AVP would provide a therapeutic target for the treatment of preeclampsia, which has to date remained elusive.

SUMMARY OF THE INVENTION

In a first aspect, a method of treating preeclampsia in a subject in need thereof, includes administering to the subject a therapeutically effective amount of a pharmaceutical compound that inhibits an arginine vasopressin receptor.

In a second aspect, a method of treating preeclampsia in a subject in need thereof, includes inhibiting production and/or secretion and/or effects of AVP and/or lowering the concentration of AVP in the blood of the subject.

In one embodiment, the method includes administering to the subject a therapeutically effective amount of a pharmaceutical compound that inhibits production and/or secretion and/or effects of AVP in the subject.

In another embodiment, the pharmaceutical compound inhibits the effects of AVP by inhibiting an arginine vasopressin receptor. In a further embodiment, the arginine vasopressin receptor includes at least one of V1A, V2, and V1B.

In one embodiment, the pharmaceutical compound is a vasopressin receptor antagonist. In a further embodiment, the pharmaceutical compound is selected from the group consisting of conivaptan, tolvaptan, and relcovaptan, and combinations thereof.

In another embodiment, the pharmaceutical compound is tetrahydrobiopterin (BH4) or a chemically related compound.

In one embodiment, the amount of the pharmaceutical compound is at least about 1 to about 50 mg per day.

In one embodiment, the concentration of AVP is lowered using an extracorporeal therapy technique. In a further embodiment, the extracorporeal therapy technique includes at least one of apheresis, hemodialysis, and hemofiltration.

In a third aspect, a composition for treatment of preeclampsia includes a therapeutically effective amount of a first arginine vasopressin receptor inhibitor and a therapeutically effective amount of a second arginine vasopressin receptor inhibitor.

In another embodiment, the first arginine vasopressin receptor inhibitor includes a first vaptan drug and the second arginine vasopressin receptor inhibitor comprises a second vaptan drug.

In a fourth aspect, a pharmaceutical dosage form includes a therapeutically effective amount of a first arginine vasopressin receptor inhibitor, a therapeutically effective amount of a second arginine vasopressin receptor inhibitor, and one or more pharmaceutically suitable carriers, diluent, and/or excipients.

In one embodiment, the dosage form includes an oral, injection, infusion, inhalation, transdermal, or implant dosage form.

In another embodiment, the pharmaceutical dosage form includes about 1 to about 500 mg of the first arginine vasopressin receptor inhibitor and about 1 to about 500 mg of the second arginine vasopressin receptor inhibitor.

In fifth aspect, a composition for treatment of preeclampsia includes a therapeutically effective amount of tetrahydrobiopterin (BH4) or a chemically related compound; and a therapeutically effective amount of an arginine vasopressin receptor inhibitor.

In a sixth aspect, a method of treating preeclampsia in a subject in need thereof includes the steps of a) removing whole blood from a patient, b) reducing or removing vasopressin in the removed blood, and c) recirculating the remaining blood components into the bloodstream of the patient.

DESCRIPTION OF THE INVENTION

Figure 1:
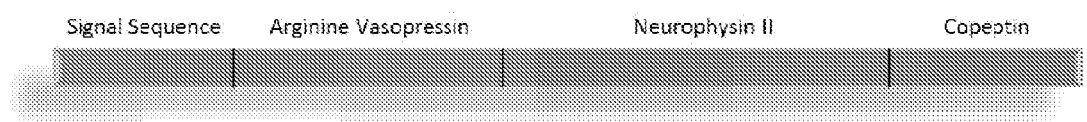
FIG. 1 The protein product of the vasopressin (AVP) gene. The signal sequence targets the protein for cellular export. AVP is then produced and released in a 1:1 molar ratio with the AVP carrier protein neurophysin II, and with copeptin. While AVP exhibits a very short half-life within the plasma, copeptin is much more stable and is primarily cleared into the urine where it can be detected easily by immuno-based assays (5).

Arginine vasopressin (AVP) is a peptide hormone synthesized primarily within magnocellular neurons of the supraoptic nucleus and paraventricular nuclei of the brain, and this hormone is translated in a 1:1 stoichiometric ratio with an inactive byproduct with a long half-life in the plasma, copeptin (FIG. 1). Axonal projections from these neurons comprise the posterior pituitary gland, and upon stimulation AVP is released into the circulation. AVP then acts upon four major types of receptors to elicit specific effects to raise blood pressure. V1A receptors are located within vascular smooth muscle and elicit vessel constriction. V1A receptors are also located throughout the central nervous system and elicit water-seeking behavior and increased sympathetic nervous activity. V1B receptors are located within parts of the hypothalamus and are involved in the regulation of ACTH release and therefore HPA-axis and glucocorticoid regulation. V2 receptors are located in the collecting duct of the kidney and mobilize aquaporin-2 to elicit water reabsorption. Finally, VACM-1 (also known as Cullin-5) is involved in cell cycle regulation. Together, the primary functions of AVP are thus to increase water intake, increase vascular contraction, and increase water reabsorption with the net effect of increasing blood pressure.

Substantial evidence supports a causative role for AVP in the development and maintenance of hypertension in many non-pregnant models. Mice with either tightly regulated or strongly overexpressed transgenic hyperactivity of the renin-angiotensin system (RAS) throughout the body require elevated AVP signaling to maintain hypertension (19, 61). Deoxycorticosterone acetate (DOCA)-salt hypertension, which is dependent upon elevated brain RAS activity (40, 50, 69) also depends upon AVP signaling. DOCA-salt treatment results in elevated plasma AVP levels (16, 57, 60, 99). Intracerebroventricular (ICV) infusion of the angiotensin converting enzyme (ACE) inhibitor, captopril, into rats both prevented and reversed DOCA-salt hypertension, and was associated with a reduction in plasma vasopressin levels despite a reduced blood pressure (40). The dependence of DOCA-salt hypertension on AVP has also been demonstrated using AVP-deficient Brattleboro rats, as the hypertensive effects of DOCA-salt are greatly diminished in these animals (16, 106). Complimenting these findings from various hypertensive models, TGR(ASrAOGEN) rats, which exhibit reduced glial production of angiotensinogen, are hypotensive and have reduced plasma AVP levels (79). These animals also exhibit altered patterns of AVP V1A receptor expression within the brain (11), further supporting a brain RAS-AVP interaction. Mice deficient for the V1A AVP receptor are hypotensive, though the relative importance of brain, vascular, cardiac, thrombocyte, and hepatic receptors is unclear (2, 48). Herein, a causative role for AVP in preeclampsia has been established. Moreover, treatments for preeclampsia targeting AVP have been identified, including inhibition of vasopressin receptor antagonists.

Preeclampsia is a medical condition characterized by high blood pressure and significant amounts of protein in the urine of a pregnant woman. If left untreated, it may develop into eclampsia, the life-threatening occurrence of seizures during pregnancy. While blood pressure elevation may be the most visible sign of the disease, it involves generalised damage to the maternal endothelium, kidneys, and liver, with the release of vasoconstrictive factors being a consequence of the original damage.

Preeclampsia may develop at any time after 20 weeks of gestation. Preeclampsia before 32 weeks is considered early onset, and is associated with increased morbidity. Its progress differs among patients; most cases are diagnosed before labor typically would begin. Preeclampsia may also occur up to six weeks after delivery. Apart from Caesarean section and induction of labor (and therefore delivery of the placenta), there is no known cure. It is the most common of the dangerous pregnancy complications; it may affect both the mother and fetus.

The term "vasopressin receptor antagonist" or "VRA", as used herein, refers to an agent which interferes with action at the vasopressin receptors. Most commonly VRAs have been used in the treatment of hyponatremia, especially in patients with congestive heart failure or liver cirrhosis.

VRAs may include tetracyclines or "vaptan" drugs, among others.

A tetracycline antibiotic, such as demeclocycline, may sometimes be used to block the action of vasopressin in the kidney in hyponatremia due to inappropriately high secretion of vasopressin, when fluid restriction has failed.

A new class of medication, called the "vaptan" drugs, may act by inhibiting the action of vasopressin on its receptors (V1A, V1B and V2). These receptors may have a variety of functions, with the V1A and V2 receptors may be expressed peripherally and involved in the modulation of blood pressure and kidney function respectively, while the V1A and V1B receptors may be expressed in the central nervous system. V1A may be expressed in many regions of the brain, and it has been linked to a variety of social behaviors in humans and animals.

The vaptan class of drugs contains a number of compounds with varying selectivity, several of which are either already in clinical use or in clinical trials. For example, conivaptan [N-(4-((4,5-dihydro-2-methylimidazo[4,5-d][1] benzazepin-6(1H)-yl)carbonyl)phenyl)-(1,1'-biphenyl)-2-carboxamide; YM 087, brand name Vaprisol®] is a non-peptide VRA. It was approved in 2004 for hyponatremia (low blood sodium levels) caused by syndrome of inappropriate antidiuretic hormone, and there is some evidence it may be effective in heart failure. Conivaptan inhibits two of the three subtypes of the vasopressin receptor (V1a and V2). Effectively, it causes iatrogenic nephrogenic diabetes insipidus.

Relcovaptan [1-([(2R,3S)-5-chloro-3-(2-chlorophenyl)-1-[(3,4-dimethoxyphenyl)sulfonyl]-3-hydroxy-2,3-dihydro-1H-indol-2-yl]carbonyl)-L-prolinamid; SR-49059] is a non-peptide vasopressin receptor antagonist, selective for the V1a subtype.

Nelivaptan [(2S,4R)-1-[(3R)-5-chloro-1-(2,4-dimethoxyphenyl)sulfonyl-3-(2-methoxyphenyl)-2-oxo-indolin-3-yl]-4-hydroxy-N,N-dimethyl-pyrrolidine-2-carboxamide] is a selective and orally active non-peptide vasopressin receptor antagonist selective for the V1b subtype.

V2 selective (V2RA) drugs may include Lixivaptan, Mozavaptan, Satavaptan, and Tolvaptan.

Lixivaptan [N-[3-chloro-4-(5H-pyrrolo-[2,1-c][1,4]benzodiazepin-; VPA-985] is a phase III pharmaceutical being developed by Cardiokine, Inc. Lixivaptan is, as of May 2010, in Phase III clinical trials involving patients with hyponatremia, including those with concomitant heart failure. Hyponatremia is an electrolyte disturbance in which the sodium concentration in the serum is lower than normal. Lixivaptan may help some patients eliminate excess fluids while retaining electrolytes.

Mozavaptan [N-[4-(5-Dimethylamino-2,3,4,5-tetrahydro-1-benzazepine-1-carbonyl)phenyl]-2-methylbenzamide; INN] is a vasopressin receptor antagonist marketed by Otsuka. In Japan, it was approved in October 2006 for hyponatremia (low blood sodium levels) caused by syndrome of inappropriate antidiuretic hormone (SIADH) due to ADH producing tumors.

Satavaptan [N-(tert-butyl)-4-[[(1s,4s)-5'-ethoxy-4-(2-morpholin-4-ylethoxy)-2'-oxospiro[cyclohexane-1,3'-indol]-1'(2'H)-yl]sulfonyl]-3-methoxybenzamide] is a vasopressin-2 receptor antagonist undergoing research for the treatment of hyponatremia. It is also being studied for the treatment of ascites.

Tolvaptan [N-(4-[[(5R)-7-chloro-5-hydroxy-2,3,4,5-tetrahydro-1H-1-benzazepin-1-yl]carbonyl]-3-methylphenyl)-2-methylbenzamide], also known as OPC-41061, is a selective, competitive vasopressin receptor 2 antagonist used to treat hyponatremia (low blood sodium levels) associated with congestive heart failure, cirrhosis, and the syndrome of inappropriate antidiuretic hormone.

Tolvaptan is also in fast-track clinical trials[2] for polycystic kidney disease. In a 2004 trial, tolvaptan, when administered with traditional diuretics, was noted to increase excretion of excess fluids and improve blood sodium levels in patients with heart failure without producing side effects such as hypotension (low blood pressure) or hypokalemia (decreased blood levels of potassium) and without having an adverse effect on kidney function. In a recently published trial (TEMPO 3:4 ClinicalTrials.gov number, NCT00428948) the study met its primary and secondary end points. Tolvaptan, when given at an average dose of 95 mg per day over a 3-year period, slowed the usual increase in kidney volume by 50% compared to placebo (2.80% per year versus 5.51% per year, respectively, $p<0.001$) and reduced the decline in kidney function when compared with that of placebo-treated patients by approximately 30% (reciprocal serum creatinine, −2.61 versus −3.81 (mg/mL)-1 per year, $p<0.001$).

Tetrahydrobiopterin, "BH4," or "THB" (trade name Kuvan) or sapropterin, refers to a naturally occurring essential cofactor of the three aromatic amino acid hydroxylase enzymes, used in the degradation of amino acid phenylalanine and in the biosynthesis of the neurotransmitters serotonin (5-hydroxytryptamine, 5-HT), melatonin, dopamine, norepinephrine (noradrenaline), epinephrine (adrenaline), and is a cofactor for the production of nitric oxide (NO) by the nitric oxide synthases. The chemical name of the compound is (6R)-2-Amino-6-[(1R,2S)-1,2-dihydroxypropyl]-5,6,7,8-tetrahydropteridin-4(1H)-one.

BH4 has multiple roles in human biochemistry. One is to convert amino acids such as phenylalanine, tyrosine, and tryptophan to precursors of dopamine and serotonin, the body's primary neurotransmitters). BH4 also serves as a catalyst for the production of nitric oxide. Among other things, nitric oxide is involved in vasodilation, which improves systematic blood flow. The role of BH4 in this enzymatic process is so critical that some research points to a deficiency of BH4—and thus, of nitric oxide—as being a core cause of the neurovascular dysfunction that is the hallmark of circulation-related diseases such as diabetes.

The term "chemically related compound," as used herein in the context of BH4, refers to a compound having similar chemical structure to that of BH4. For example, a chemically related compound may have any other suitable substitution group instead of the amino group in the aromatic ring of BH4. A chemically related compound may also have any other suitable substitution groups on any other location of the BH4.

The term "extracorporeal therapy," as used herein, refers to an extracorporeal medical procedure or a medical procedure which is performed outside the body. An exemplary extracorporeal therapy may include circulatory procedures. Circulatory procedures are procedures in which blood is taken from a patient's circulation to have a process applied to it before it is returned to the circulation. All of the apparatus carrying the blood outside the body is termed the extracorporeal circuit.

The present disclosure contemplates pharmaceutical formulations, dosage forms, kits, and methods wherein a compound, such as a pharmaceutical compound, that reverses or negates the effects of AVP or mimics thereof to reduce preeclampsia in a subject in need thereof.

The contemplated pharmaceutical formulations, dosage forms, kits, and methods may further include a plurality of drugs or pharmaceutically acceptable salts or derivatives thereof that inhibit production and/or secretion of AVP and/or AVP receptors together with one or more pharmaceutically acceptable carriers therefor, and optionally, other therapeutic and/or prophylactic ingredients. The carrier(s) should be acceptable in the sense of being compatible with the other ingredients of the formulation and being physiologically acceptable to the recipient thereof.

For example, compositions herein may be formulated for oral, rectal, nasal, topical (including buccal and sublingual), transdermal, vaginal, injection/injectable, and/or parental (including subcutaneous, intramuscular, intravenous, and intradermal) administration. Other suitable administration routes are incorporated herein. The compositions may be presented conveniently in unit dosage forms and may be prepared by any methods known in the pharmaceutical arts. Examples of suitable drug formulations and/or forms are discussed in, for example, Hoover, John E. Remington's Pharmaceutical Sciences, Mack Publishing Co., Easton, Pa.; 18.sup.th edition (1995); and Liberman, H. A. and Lachman, L. Eds., Pharmaceutical Dosage Forms, Marcel Decker, New York, N.Y., 1980. Illustrative methods include the step of bringing one or more active ingredients into association with a carrier that constitutes one or more accessory ingredients. In general, the compositions may be prepared by bringing into association uniformly and intimately one or more active ingredients with liquid carriers or finely divided solid carriers or both, and then, if necessary, shaping the product.

Pharmaceutical formulations may include those suitable for oral, intramuscular, rectal, nasal, topical (including buccal and sub-lingual), vaginal or parenteral (including intramuscular, subcutaneous and intravenous) administration or in a form suitable for administration by inhalation or insufflation. One or more of the compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

A salt may be a pharmaceutically suitable (i.e., pharmaceutically acceptable) salt including, but not limited to, acid addition salts formed by mixing a solution of the instant compound with a solution of a pharmaceutically acceptable acid. A pharmaceutically acceptable acid may be, for example, hydrochloric acid, methanesulphonic acid, fumaric acid, maleic acid, succinic acid, acetic acid, benzoic acid, oxalic acid, citric acid, tartaric acid, carbonic acid or phosphoric acid.

Suitable pharmaceutically-acceptable salts may further include, but are not limited to salts of pharmaceutically-acceptable inorganic acids, including, for example, sulfuric, phosphoric, nitric, carbonic, boric, sulfamic, and hydrobromic acids, or salts of pharmaceutically-acceptable organic acids such propionic, butyric, maleic, hydroxymaleic, lactic, mucic, gluconic, benzoic, succinic, phenylacetic, toluenesulfonic, benezenesulfonic, salicyclic sulfanilic, aspartic, glutamic, edetic, stearic, palmitic, oleic, lauric, pantothenic, tannic, ascorbic, and valeric acids.

Various pharmaceutically acceptable salts include, for example, the list of FDA-approved commercially marketed salts including acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

A hydrate may be a pharmaceutically suitable (i.e., pharmaceutically acceptable) hydrate that is a compound formed by the addition of water or its elements to a host molecule (for example, the free form version of the compound) including, but not limited to, monohydrates, dihydrates, etc.

A solvate may be a pharmaceutically suitable (i.e., pharmaceutically acceptable) solvate, whereby solvation is an interaction of a solute with a solvent which leads to stabilization of the solute species in a solution, and whereby the solvated state is an ion in a solution complexed by solvent molecules. Solvates and hydrates may also be referred to as "analogues."

A prodrug may be a compound that is pharmacologically inert but are converted by enzyme or chemical action to an active form of the drug (i.e., an active pharmaceutical ingredient) at or near the predetermined target site. In other words, prodrugs are inactive compounds that yield an active compound upon metabolism in the body, which may or may not be enzymatically controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism.

Carrier prodrugs are formed by combining the active drug with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as bipartite prodrugs. Prodrugs where the carrier is linked to the drug by a separate structure are referred to as tripartite prodrugs, whereby the carrier is removed by an enzyme-controlled metabolic process, and whereby the linking structure is removed by an enzyme system or by a chemical reaction. A hydroxy-protecting group includes, for example, a tert-butyloxy-carbonyl (t-BOC) and t-butyl-dimethyl-silyl (TBS). Other hydroxy protecting groups contemplated are known in the art.

In another embodiment, a dosage form and/or composition may include one or more active metabolites of the active ingredients in place of or in addition to the active ingredients disclosed herein. Dosage form compositions containing the active pharmaceutical ingredients may also contain one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (for example, anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, a kit may be a packaged collection of related materials, including, for example, a single and/or a plurality of dosage forms each approximating an effective amount of an active ingredient, such as, for example, an AVP receptor inhibitor and/or an additional drug. The included dosage forms may be taken at one time, or at prescribed interval.

As used herein, an oral dosage form may include capsules (a solid oral dosage form consisting of a shell and a filling, whereby the shell is composed of a single sealed enclosure, or two halves that fit together and which are sometimes sealed with a band and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), and capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle).

Oral dosage forms contemplated herein also include granules (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), or syrup (an oral solution containing high concentrations of sucrose or other sugars; the term has also been used to include any other liquid dosage form prepared in a sweet and viscid vehicle, including oral suspensions).

Oral dosage forms contemplated herein may further include a tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, for example, citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), and the like.

Injection and infusion dosage forms (i.e., parenteral dosage forms) include, but are not limited to, the following. Liposomal injection includes or forms liposomes or a lipid bilayer vesicle having phospholipids that encapsulate an active drug substance. Injection includes a sterile preparation intended for parenteral use. Five distinct classes of injections exist as defined by the USP. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution suitable for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

A parenteral carrier system may include one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

Inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols). Inhalation dosage forms further include foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. Inhalation dosage forms also include metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and aerosol spray being an aerosol product which utilizes a compressed gas as the propellant to provide the force necessary to expel the product as a wet spray and being applicable to solutions of medicinal agents in aqueous solvents.

Pharmaceutically suitable inhalation carrier systems may include pharmaceutically suitable inactive ingredients known in the art for use in various inhalation dosage forms, such as (but not limited to) aerosol propellants (for example, hydrofluoroalkane propellants), surfactants, additives, suspension agents, solvents, stabilizers and the like.

A transdermal dosage form may include, but is not limited to, a patch being a drug delivery system that often contains an adhesive backing that is usually applied to an external site on the body, whereby the ingredients either passively diffuse from, or are actively transported from some portion of the patch, and whereby depending upon the patch, the ingredients are either delivered to the outer surface of the body or into the body; and other various types of transdermal patches such as matrix, reservoir and others known in the art. The "pharmaceutically suitable transdermal carrier system" includes pharmaceutically suitable inactive ingredients known in the art for use in various transdermal dosage forms, such as (but not limited to) solvents, adhesives, diluents, additives, permeation enhancing agents, surfactants, emulsifiers, liposomes, and the like.

Suitable dosage amounts and dosing regimens may be selected in accordance with a variety of factors, including one or more particular conditions being treated, the severity of the one or more conditions, the genetic profile, age, health, sex, diet, and weight of the subject, the route of administration alone or in combination with pharmacological considerations including the activity, efficacy, bioavailability, pharmacokinetic, and toxicological profiles of the particular compound employed, whether a drug delivery system is utilized and whether the drug is administered as part of a drug combination. Therefore, the dosage regimen to be employed may vary widely and may necessarily deviate from the dosage regimens set forth herein.

Contemplated dosage forms may include an amount of one or more compounds that inhibit production and/or secretion of AVP and/or inhibit or otherwise block AVP receptors or the effects of AVP ranging from about 1 to about 1200 mg/kg, or about 1 to about 50 mg/kg, or about 5 to about 100 mg/kg, or about 25 to about 800 mg/kg, or about 100 to about 500 mg/kg, or 0.1 to 50 milligrams/kilogram (±10%), or 10 to 100 milligrams/kilogram (±10%), or 1 to 600 milligrams/kilogram (±10%), or 0.1 to 200 milligrams/kilogram (±10%), or 1 to 100 milligrams/kilogram (±10%), or 5 to 50 milligrams/kilogram (±10%), or 30 milligrams/kilogram (±10%), or 20 milligrams/kilogram (±10%), or 10 milligrams/kilogram (±10%), or 5 milligrams/kilogram (±10%), per dosage form, such as, for example, a tablet, a pill, a bolus, and the like.

In another embodiment, a dosage form may be administered to a subject in need thereof once per day, or twice per day, or once every 6 hours, or once every 4 hours, or once every 2 hours, or hourly, or twice an hour, or twice a day, or twice a week, or monthly. A therapeutically effective amount of a compound that inhibits production and/or secretion and/or effects of AVP and/or AVP receptors or mimics thereof, such as, for example, a "vaptan," may be any amount that begins to reduce preeclampsia features in a subject receiving the compound.

It is further contemplated that one active ingredient may be in an extended release form, while a second other may not be, so the recipient experiences, for example, a spike in the second active ingredient that dissipates rapidly, while the first active ingredient is maintained in a higher concentration in the blood stream over a longer period of time. Similarly, one of the active ingredients may be an active metabolite, while another may be in an unmetabolized state, such that the active metabolite has an immediate effect upon administration to a subject whereas the unmetabolized active ingredient administered in a single dosage form may need to be metabolized before taking effect in the subject.

Also contemplated are solid form preparations that include at least one active ingredient which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Solutions or suspensions may be applied topically and/or directly to the nasal cavity, respiratory tract, eye, or ear by conventional means, for example with a dropper, pipette or spray. Alternatively, one or more of the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form, for example, in capsules or cartridges of, for example, gelatin, or blister packs from which the powder may be administered by means of an inhaler.

The pharmaceutical preparations may be in unit dosage forms. In such form, the preparation may be subdivided into unit doses containing appropriate quantities of the active component. The unit dosage form can be a packaged preparation, such as a kit or other form, the package containing discrete quantities of preparation, such as packeted tablets, capsules, liquids or powders in vials or ampules. Also, the unit dosage form can be a capsule, tablet, cachet, or lozenge, or it can be the appropriate number of any of these in packaged form. Contemplated kits may include any combination of disclosed dosage forms.

In one embodiment, a method for the treatment of preeclampsia in a subject in need thereof includes administering to the subject a therapeutically effective amount of a pharmaceutical compound that inhibits an arginine vasopressin receptor.

In one embodiment, the amount of the pharmaceutical compound is at least about 1 to about 50 mg per day.

In another embodiment, the arginine vasopressin receptor includes at least one of V1A, V2, and V1B.

In one embodiment, the pharmaceutical compound is a vasopressin receptor antagonist. Examples of vasopressin receptor antagonists include "vaptan" drugs. Specific examples of vaptans includes conivaptan, tolvaptan, and relcovaptan, lixivaptan, mozavaptan, satavaptan. It is envisioned that combinations of vaptans and/or or additional vasopressin receptor antagonists may be combined into a single composition. It is further envisioned that drugs that inhibit secretion and/or production of AVP may be combined with vasopressin receptor antagonists to form a therapeutic composition for the treatment of preeclampsia.

In one example, a composition for treatment of preeclampsia includes a therapeutically effective amount of a first arginine vasopressin receptor inhibitor and optionally a therapeutically effective amount of a second arginine vasopressin receptor inhibitor. For example, a composition may include a first arginine vasopressin receptor inhibitor, such as conivaptan, and/or a second arginine vasopressin receptor inhibitor and/or an inhibitor of AVP secretion and/or production.

In another embodiment, a composition for treatment of preeclampsia may comprise a therapeutically effective amount of tetrahydrobiopterin (BH4) or a chemically related compound.

In one embodiment, a composition for treatment of preeclampsia may comprise a therapeutically effective amount of BH4 or a chemically related compound, and a therapeutically effective amount of at least one arginine vasopressin receptor inhibitor as discussed above or any inhibitors as understood by a person having ordinary skill in the art.

In one embodiment, a composition for treatment of preeclampsia may comprise a therapeutically effective amount of BH4 or a chemically related compound, a therapeutically effective amount of a first arginine vasopressin receptor inhibitor and optionally a therapeutically effective amount of a second arginine vasopressin receptor inhibitor. For example, a composition may comprise BH4 or a chemically related compound, a first arginine vasopressin receptor inhibitor, such as conivaptan, and/or a second arginine vasopressin receptor inhibitor and/or an inhibitor of AVP secretion and/or production.

In a third aspect, a pharmaceutical dosage form includes a therapeutically effective amount of a first arginine vasopressin receptor inhibitor, a therapeutically effective amount of a second arginine vasopressin receptor inhibitor, and one or more pharmaceutically suitable carriers, diluent, and/or excipients.

In one embodiment, the dosage form includes an oral, injection, infusion, inhalation, transdermal, or implant dosage form.

In another embodiment, the pharmaceutical dosage form includes about 1 to about 500 mg of conivaptan and about 1 to about 500 mg of at least one of tolvaptan and relcovaptan.

The treatments contemplated herein may be administered prophylactically before onset of preeclampsia, as well as after onset of preeclampsia. It is further envisioned that treatment regimens (e.g., dosing levels) may alter over time and may be informed by urine and/or serum measurements of vasopressin, neurophysin II, and/or copeptin levels.

In another aspect, a pharmaceutical dosage form may comprise a therapeutically effective amount of BH4 or a chemically related compound and one or more pharmaceutically suitable carriers, diluents, and/or excipients.

In one embodiment, a pharmaceutical dosage form may comprise a therapeutically effective amount of BH4 or a chemically related compound and a therapeutically effective amount of at least one arginine vasopressin receptor inhibitor. A suitable arginine vasopressin receptor inhibitor may include those as discussed above and any inhibitors as understood by a person having ordinary skill in the art.

In one specific embodiment, the arginine vasopressin receptor inhibitor may comprise at least one of conivaptan, tolvaptan and relcovaptan.

In one embodiment, a pharmaceutical dosage form may comprise a therapeutically effective amount of BH4 or a chemically related compound, a first arginine vasopressin receptor inhibitor, a therapeutically effective amount of a second arginine vasopressin receptor inhibitor, and one or more pharmaceutically suitable carriers, diluent, and/or excipients.

In one specific embodiment, the arginine vasopressin receptor inhibitor may comprise at least one of conivaptan, tolvaptan and relcovaptan.

An appropriate dosage level for the present invention may generally be about 0.001 to about 500 mg per kg subject body weight per day which can be administered in a single or multiple doses. Preferably, the dosage level will be about 0.01 to about 250 mg/kg per day; more preferably about 0.05 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage may be about 0.05 to about 0.5, about 0.5 to about 5 or about 5 to about 50 mg/kg per day. The dosage may be selected, for example, to include any dose within any of these ranges, for therapeutic efficacy and/or symptomatic adjustment of the dosage to the subject to be treated.

Dosage ranges for agents may be as low as 5 ng/day. In certain embodiments, about 10 ng/day, about 15 ng/day, about 20 ng/day, about 25 ng/day, about 30 ng/day, about 35 ng/day, about 40 ng/day, about 45 ng/day, about 50 ng/day, about 60 ng/day, about 70 ng/d, about 80 ng/day, about 90 ng/day, about 100 ng/day, about 200 ng/day, about 300 ng/day, about 400 ng/day, about 500 ng/day, about 600 ng/day, about 700 ng/day, about 800 ng/day, about 900 ng/day, about 1 μg/day, about 2 μg/day, about 3 μg/day, about 4 μg/day, about 5 μg/day, about 10 μg/day, about 15 μg/day, about 20 μg/day, about 30 μg/day, about 40 μg/day, about 50 μg/day, about 60 μg/day, about 70 μg/day, about 80 μg/day, about 90 μg/day, about 100 μg/day, about 200 μg/day, about 300 μg/day, about 400 μg/day, about 500 μg/day, about 600 μg/day, about 700 μg/day, about 800 μg/day, about 900 μg/day, about 1 mg/day, about 2 mg/day, about 3 mg/day, about 4 mg/day, about 5 mg/day, about 10 mg/day, about 15 mg/day, about 20 mg/day, about 30 mg/day, about 40 mg/day, or about 50 mg/day of an agent of the invention is administered.

In certain embodiments, the agents of the invention are administered in pM or nM concentrations. In certain embodiments, the agents are administered in about 1 pM, about 2 pM, about 3 pM, about 4 pM, about 5 pM, about 6 pM, about 7 pM, about 8 pM, about 9 pM, about 10 pM, about 20 pM, about 30 pM, about 40 pM, about 50 pM, about 60 pM, about 70 pM, about 80 pM, about 90 pM, about 100 pM, about 200 pM, about 300 pM, about 400 pM, about 500 pM, about 600 pM, about 700 pM, about 800 pM, about 900 pM, about 1 nM, about 2 nM, about 3 nM, about 4 nM, about 5 nM, about 6 nM, about 7 nM, about 8 nM, about 9 nM, about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, or about 900 nM concentrations.

In certain embodiments, the size of the active agent is important. In certain embodiments, the active agent is less than about 3 μm, less than about 2 μm, less than about 1 μm in diameter. In certain embodiments, the active agent is from about 0.1 μm to about 3.0 μm in diameter. In certain embodiments, the active agent is from about 0.5 μm to about 1.5 μm in diameter. In certain embodiments, the active agent is about 0.2 μm, about 0.3 μm, about 0.4 μm, about 0.5 μm, about 0.6 μm, about 0.7 μm, about 0.8 μm, about 0.9 μm, about 1.0 μm, about 1.1 μm, about 1.2 μm, about 1.3 μm, about 1.4 μm, or about 1.5 μm in diameter.

It may be advantageous for the pharmaceutical combination to be comprised of a relatively large amount of the first component compared to the second component. In certain instances, the ratio of the first active agent to second active agent is about 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, 15:1, 10:1, 9:1, 8:1, 7:1, 6:1, 5:1, 4:1, 3:1, 2:1, or 1:1. It further may be preferable to have a more equal distribution of pharmaceutical agents. In certain instances, the ratio of the first active agent to the second active agent is about 4:1, 3:1, 2:1, 1:1, 1:2, 1:3, or 1:4. It also may be advantageous for the pharmaceutical combination to have a relatively large amount of the second component compared to the first component. In certain instances, the ratio of the second active agent to the first active agent is about 30:1, 20:1, 15:1, 10:1, 9:1, 8:1, 7:1, 6:1, or 5:1. In certain instances, the ratio of the second active agent to first active agent is about 100:1, 90:1, 80:1, 70:1, 60:1, 50:1, or 40:1. In certain instances, the ratio of the second active agent to first active agent is about 200:1, 190:1, 180:1, 170:1, 160:1, 150:1, 140:1, 130:1, 120:1, or 110:1. A composition comprising any of the above-identified combinations may be administered in divided doses about 1, 2, 3, 4, 5, 6, or more times per day or in a form that will provide a rate of release effective to attain the desired results. The dosage form may contain both the first and second active agents. The dosage form may be administered one time per day if it contains both the first and second active agents.

For example, a formulation intended for oral administration to humans may contain from about 0.1 mg to about 5 g of the first therapeutic agent and about 0.1 mg to about 5 g of the second therapeutic agent, both of which are compounded with an appropriate and convenient amount of carrier material varying from about 5 to about 95 percent of the total composition. Unit dosages will generally contain between about 0.5 mg to about 1500 mg of the first therapeutic agent and 0.5 mg to about 1500 mg of the second therapeutic agent. The dosage may be about 25 mg, 50 mg, 100 mg, 200 mg, 300 mg, 400 mg, 500 mg, 600 mg, 800 mg, or 1000 mg, etc., up to about 1500 mg of the first therapeutic agent. The dosage may be about 25 mg, 50 mg, 100 mg, 200 mg, 300 mg, 400 mg, 500 mg, 600 mg, 800 mg, or 1 000 mg, etc., up to about 1500 mg of the second therapeutic agent.

In one aspect, a method of treating preeclampsia in a subject in need thereof is disclosed. The present method of treating preeclampsia in a subject may comprise the step of removing vasopressin from the circulation system (e.g., blood) of a patient. In one embodiment, the method may comprise the steps of a) removing whole blood from a patient; b) separating the blood into individual components; c) reducing or removing vasopressin in the blood; and d)

re-circulating the remaining blood components into the bloodstream of the patient. In one embodiment, the present method of treating preeclampsia may be applied by using any suitable apparatus. For example, one may use any commercially available extracorporeal therapy techniques, such as apheresis, hemodialysis (also haemodialysis), hemofiltration, and others. For example, column-based modulation of vasopressin may be used as part of a multifaceted or singular treatment or prevention for preeclampsia focused on decreasing circulating vasopressin. An extracorporeal apheresis type column may be used to this end. Similar to apheresis columns used in renal hemodialysis, in this embodiment, a column may be used to pass human blood through that: 1) chelates and/or absorbs circulating vasopressin and/or copeptin using a chelator of vasopressin, such as but not limited to, an antibody that is attached to the stationary phase of the column and/or internal column surfaces; 2) inactivates circulating vasopressin and/or copeptin using a column loaded with LNPEP and/or vasopressinase; 3) simultaneously inactivates or chelates other effectors of preeclampsia such as sFLT-1; and 4) all of the above.

Much like hemodialysis, treatment using these developed columns would involve placing an intravenous (IV) line into a patient which would pump the patient blood extracorporeally through the IV line into the developed column. The column chelates or otherwise inactivates vasopressin and/or copeptin. The blood will then be pumped back into the patient to improve the subject's health.

There are currently preliminary data to suggest that extracorporeal removal of sFLT-1 is possible using column technology. In a pilot study by Thadhani, et al. (93), five women with very preterm preeclampsia underwent a single dextran sulfate cellulose apheresis treatment. In these women, the treatment decreased circulating sFlt-1, reduced proteinuria, and stabilized blood pressure without adverse effects to the mother and fetus. A developed extracorporeal column to chelate and/or inactivate vasopressin and/or copeptin can be used in a similar way.

Unless defined otherwise in this specification, technical and scientific terms used herein have the same meaning as commonly understood by one of ordinary skill in the art to which this invention belongs and by reference to published texts.

It should be understood that while various embodiments in the specification are presented using "comprising" language, under various circumstances, a related embodiment may also be described using "consisting of" or "consisting essentially of" language. It is to be noted that the term "a" or "an," refers to one or more, for example, "an immunoglobulin molecule," is understood to represent one or more immunoglobulin molecules. As such, the terms "a" (or "an"), "one or more," and "at least one" is used interchangeably herein.

The following examples set forth preferred markers and methods in accordance with the invention. It is to be understood, however, that these examples are provided by way of illustration and nothing herein should be taken as a limitation upon the overall scope of the invention.

EXAMPLES

The following examples illustrate that vasopressin infusion recapitulates all in one model, simultaneously, all of the key phenotypes of preeclampsia: increased blood pressure, renal morphological pathologies, proteinuria, intrauterine growth restriction, and spontaneous preterm labor. There-fore, these examples establish a causative role of vasopressin in preeclampsia and have enabled the identification of tools and agents for the successful treatment of preeclampsia.

Example 1. Hypertension in Mice with Transgenic Activation of the Brain Renin-Angiotensin System is Vasopressin Dependent Activity of the local tissue renin-angiotensin system (RAS) within the brain has been implicated in the development and maintenance of elevated blood pressure in many forms of hypertension. Evidence specifically demonstrating a causal role for brain RAS activity in hypertension comes from various rodent models. These many models include peripheral angiotensin infusion models (63, 82, 107), both elevated (20) and suppressed (38, 50, 69) plasma renin models, psychogenic (59), cold exposure (88), renal injury (103), sleep apnea (18) models, transgenic TGR (mRen2)27 rats (89), and both Dahl salt-sensitive (38) and spontaneously hypertensive rats (SHR) maintained on high-salt diets (49, 65, 102). Two major mechanisms have been documented that account for the blood pressure effects of brain angiotensin. First, actions of the RAS within the supraoptic (SON) and paraventricular hypothalamic nuclei (PVN) stimulate the production and release of arginine vasopressin (AVP, also known as antidiuretic hormone, ADH, or argipressin) (6, 15, 23, 40, 70, 73, 89). Second, hindbrain and brain stem actions of the RAS alter baroreflex function and sympathetic output (30, 34). Interestingly, a population of AVP-expressing neurons project from the PVN to the hindbrain and spinal cord and appear to be involved in the regulation of sympathetic nervous activity, suggesting a possible AVP-mediated cross-talk between these two mechanisms.

Although some studies have failed to document a substantial role for AVP in blood pressure control in heterogenous groups of human subjects (67), AVP has been implicated as a significant contributor to blood pressure control in selected populations of humans (26, 66). Specifically, African Americans (4), the elderly (21), and patients with congestive heart failure (26) or chronic renal failure (3) all exhibit AVP-dependent hemodynamic changes (9). Importantly, these populations of humans all exhibit low levels of circulating renin (105). As low-renin hypertension accounts for a larger (27%) fraction of human essential hypertensives than high-renin hypertension (16%) (51), it is unclear whether therapeutic targeting of AVP may have been prematurely overlooked as an antihypertensive therapy for selected populations of hypertensive patients.

Together, these findings have led us to question whether the elevations in AVP are necessary to cause or maintain hypertension due to chronically elevated brain RAS activity and to probe the mechanism(s) of action of AVP in this context. We hypothesized that transgenic activation of the brain RAS would elevate plasma AVP, and that actions of AVP are required to induce hypertension by the brain RAS through some combination of vasoconstriction and altered renal function. To examine these hypotheses, we utilized a unique transgenic animal model previously developed in our laboratory (29, 76). This double-transgenic model (the "sRA" model) takes advantage of the species specificity of the renin-mediated cleavage of angiotensinogen to cause brain-specific hyperactivity of the RAS. We have previously demonstrated that these animals exhibit a robust chronic hypertension, polydipsia, polyuria, and an elevated resting metabolic rate. Importantly, we have also previously determined that sRA mice exhibit elevated plasma AVP levels and a suppression of the circulating RAS despite elevated renal sympathetic nerve activity (29). Here we demonstrate elevated neuronal AVP immunostaining (specifically in the supraoptic nucleus), increased daily secretion of AVP, robust desensitization of the vasculature of sRA mice to AVP, and the necessity of V2 AVP receptor signaling in the maintenance of hypertension and hyponatremia in this model. These findings highlight a major role for AVP in the hypertension of sRA mice.

Materials and Methods:

Animals. All animal work was approved by the University of Iowa Animal Care and Use Committee and was performed in accordance with the National Institutes of Health "Guide for the Care and Use of Laboratory Animals."

Double-transgenic (sRA) mice were generated as previously described (29, 76). Briefly, "sR" mice expressing human renin under transcriptional control by the neuron-specific synapsin promoter were bred with "A" mice expressing human angiotensinogen under transcriptional control by its own promoter (line 11110/2×4284/1). Because of the species specificity of the reaction, human angiotensinogen is only cleaved to form angiotensin I by human renin. Hyperactivity of the RAS is thereby restricted to sites of overlapping transgene expression in sRA offspring (i.e., subsections of the central nervous system that normally produce angiotensinogen).

Immunohistochemistry Immunohistochemical detection of AVP in the brain was performed on 50 μm thick sections using a rabbit polyclonal antibody to a synthetic peptide corresponding to the first six amino acids of arginine8-vasopressin (Phoenix Pharmaceuticals, Burlingame, Calif.). Sections were cut from six (3 sRA, 3 wild type) brains perfusion fixed with 4% paraformaldehyde and 0.5% glutaraldehyde and incubated in a 1:1,000 dilution of antibody for 24 h at 4° C. The brains of sRA mice were "notched" for identification and incubated with sections from wild-type animals. After incubation in a biotinylated goat anti-rabbit secondary antibody and avidin-horseradish peroxidase, immunoreactivity was detected using 3,3=-diaminobenzidine as a chromagen. On four sections from each animal, matched for rostrocaudal level, AVP-immunostained fragments larger than 10 μm were counted in the PVN and SON using ImageJ software from the NIH.

Blood pressure (tail-cuff). Here we first examined blood pressure in sRA mice using a Visitech Systems BP-2000 tail-cuff blood pressure monitoring system, as previously described (84). Briefly, animals were acclimated to warmed restraint boxes daily for 1 wk. Once acclimated, 30 measurements of systolic blood pressure were averaged from each animal daily for 2 wk to assess baseline blood pressure. Conivaptan (Vaprisol, YM 087, 22 ng/h sc, Baxter Healthcare) or tolvaptan (OPC-41061, 22 ng/h sc, Sigma Aldrich) was delivered to distinct subsets of mice by osmotic minipump (model 1004, Alzet). After osmotic minipump implantation, pressures were recorded daily for 10 days to assess drug effects.

Blood pressure (telemetry). Radiotelemetric blood pressures were recorded from the carotid artery essentially as previously reported (29). Briefly, a telemeter probe (DSI, model TA11PA-C10) was inserted into the common carotid artery under ketamine-xylazine anesthesia. After >2 days of recovery, blood pressure, heart rate, and spontaneous physical activity were recorded for 30 s every 5 min using the Dataquest program (DSI). After baseline recordings, mice were chronically delivered conivaptan and tolvaptan via osmotic minipump that was implanted through an interscapular incision into the subcutaneous space of the back under isoflurane anesthesia.

Aortic Vascular Reactivity: Abdominal aortic rings were assessed for vascular reactivity as previously described (32). Briefly, mice were euthanized by overdose of pentobarbital (50 mg, i.p.), and the abdominal aorta was quickly removed and placed in Kreb's buffer containing (in mmol/L): 118.3 NaCl, 4.7 KCl, 1.2 MgSO4, 1.2 KH2PO4, 25 NaHCO3, 2.5 CaCl2 and 11 glucose. Vascular rings (4-5 mm in length) were suspended in oxygenated Kreb's buffer (95% O2/5% CO2) in organ baths at 37° C. and connected to a force transducer via steel hooks. Resting tension was adjusted to 0.5 grams over 45 minutes. Contractile responses were tested in response to AVP ($10^{-10}$-$10^{-6}$ mol/L), phenylephrine (PE, $10^{-8}$-3×$10^{-5}$), endothelin-1 (ET-1, $10^{-10}$-$10^{-7}$), prostaglandin F2α (PGF2α, $10^{-7}$-$10^{-4}$), and angiotensin II (Ang II, $10^{-10}$-$10^{-7}$). Following sub-maximal contraction with PGF2α (40-50% of max; 3×$10^{-6}$-6×$10^{-6}$), relaxation responses to acetylcholine ($10^{-8}$-3×$10^{-5}$) and sodium nitroprusside ($10^{-9}$-$10^{-5}$) were determined.

Mesenteric Artery Vascular Reactivity: Secondary branches of mesenteric artery were dissected and placed in chilled oxygenated (21% O2, 5% CO2, and 74% N2) Kreb's buffer. A segment (~1 mm long) of artery was transferred to a vessel chamber (DMT), cannulated with glass micropipettes and secured with silk ligatures. The artery was slowly pressurized to 40 mmHg without flow. After 30 min equilibration, vessel viability was tested by constriction response to 100 mM KCl. Vascular responses to PE (10-9-10-5 mol/L), AVP (10-12-10-7 mol/L), and ET-1 (10-11-10-8 mol/L) were then assessed. The artery was then superfused with calcium-free Krebs buffer containing 10-5 mol/L sodium nitroprusside and 2 mmol/L EGTA to maximally dilate the vessel. Internal and external diameters were measured at 75 mm Hg. Wall thickness, media/lumen ratio and cross sectional area (CSA) were calculated as previously described by Neves, et al. (62).

Gene Expression: Mesenteric arteries (superior mesenteric artery excluded) and kidneys were snap frozen in liquid nitrogen and RNA was extracted in Trizol®. Total RNA was isolated using an RNA Purelink® Minikit (Invitrogen) following the manufacturer's protocol. Concentrations were determined using a NanoDrop ND-1000. cDNA was generated by RT-PCR using SuperScript III® (Invitrogen). qRT-PCR was performed using TaqMan gene expression assays (Applied Biosystems): RGS2 (Mm00501385_m1), RGS5 (Mm00501393_m1), V1A (Mm00444092_m1), ETA (Mm01243722_m1), GAPDH (4352932E), or SYBR188 green assays (primer sequences in Table 1: NKCC2, NCC, NHE3, ENaC-α, ENaC-β, ENaC-γ, NKA-α, V2R, AQP1, AQP2, AQP3, AQP4, PGES, and UT1-A) normalized against β-actin. SYBR-green reagents from Bio-Rad were utilized, and all real time reactions were performed on a Bio-Rad iQ5 iCycle®.

| Gene | Primer Sequences | |
|---|---|---|
| NKCC2 | Forward: 5'-CCATGGTAACCTCTATCACTGGGT-3' | SEQ ID NO. 1 |
| | Reverse: 5'-TCAAGCCTATTGACCCACCGAACT-3' | SEQ ID NO. 2 |

-continued

| Gene | Primer Sequences | |
|---|---|---|
| NCC | Forward: 5'-AAGTCGGGTGGCACCTATTTCCTT-3' | SEQ ID NO. 3 |
| | Reverse: 5'-TTACGGTTTCTGCAAAGCCCACAG-3' | SEQ ID NO. 4 |
| NHE3 | Forward: 5'-TCCTCTCAGCCATTGAGGACATCT-3' | SEQ ID NO. 5 |
| | Reverse: 5'-ACTTTGCTGAGGAACTTCCGGTCA-3' | SEQ ID NO. 6 |
| ENaCα | Forward: 5'-ACAATGGTTTGTCCCTGACACTGC-3' | SEQ ID NO. 7 |
| | Reverse: 5'-TCACGTTGAAGCCACCATCATCCA-3' | SEQ ID NO. 8 |
| ENaCβ | Forward: 5'-TCTGCCAACCCTGGGACTGAATTT-3' | SEQ ID NO. 9 |
| | Reverse: 5'-TGGCATAGATGCCCTCCTCTCTAA-3' | SEQ ID NO. 10 |
| ENaCγ | Forward: 5'-GCCAATCAGTGTGCAAGCAATCCT-3' | SEQ ID NO. 11 |
| | Reverse: 5'-TTATTTGCTGGCTTTGGTCCCAGG-3' | SEQ ID NO. 12 |
| Na-K ATPase-α | Forward: 5'-TGAAGCTGACACCACGGAGAATCA-3' | SEQ ID NO. 13 |
| | Reverse: 5'-TGCCGCTTAAGAATAGGCAGGTT-3' | SEQ ID NO. 14 |
| V2R | Forward: 5'-TGTGATTGTCTACGTGCTGTGCTG-3' | SEQ ID NO. 15 |
| | Reverse: 5'-GGGTTGGTACAGCTGTTAAGGCTA-3' | SEQ ID NO. 16 |
| AQP1 | Forward: 5'-CTGGGCATTGAGATCATTGGCACT-3' | SEQ ID NO. 17 |
| | Reverse: 5'-TGATACCGCAGCCAGTGTAGTCAA-3' | SEQ ID NO. 18 |
| AQP2 | Forward: 5'-TAGCCCTGCTCTCTCCATTGGTTT-3' | SEQ ID NO. 19 |
| | Reverse: 5'-AAACTTGCCAGTGACAACTGCTGG-3' | SEQ ID NO. 20 |
| AQP3 | Forward: 5'-ATGGTGGCTTCCTCACCATCAACT-3' | SEQ ID NO. 21 |
| | Reverse: 5'-AGGAAGCACATTGCGAAGGTCACA-3' | SEQ ID NO. 22 |
| AQP4 | Forward: 5'-TGCCAGCTGTGATTCCAAACGAAC-3' | SEQ ID NO. 23 |
| | Reverse: 5'-TCCCATGATAACTGCGGGTCCAAA-3' | SEQ ID NO. 24 |
| PGES | Forward: 5'-TTTGCAACAAGTACTGGCCCATGC-3' | SEQ ID NO. 25 |
| | Reverse: 5'-TGTTCGGTACACGTTGGGAGAGAT-3' | SEQ ID NO. 26 |
| UT1-A | Forward: 5'-CACTGGCGACATGAAGGAATGCAA-3' | SEQ ID NO. 27 |
| | Reverse: 5'-GGGTTGTTGACAAACATCACCTGAGC-3' | SEQ ID NO. 28 |
| B-actin | Forward 5'-CATCCTCTTCCTCCCTGGAGAAGA-3' | SEQ ID NO. 29 |
| | Reverse 5'-ACAGGATTCCATACCCAAGAAGGAAGG-3' | SEQ ID NO. 30 |

Blood and urine analyses: Plasma was obtained by collecting whole blood by submandibular bleed into lithium heparin coated tubes, then centrifuged at 5,000×g for 5 minutes, and the supernatant transferred to a fresh tube and frozen at −80° C. until analysis. Urine was collected using Nalgene single-mouse metabolism cages as previously described (29). Copeptin was measured using an ELISA kit (USCN Life Sciences), according to the manufacturer's instructions. Blood chemistries and urine creatinine were determined using a handheld iSTAT clinical chemistry analyzer (Abbott), with CHEM8+ cartridges. Urine protein was determined using a bicinchoninic acid assay kit (Thermo Fisher/Pierce), according to the manufacturer's instructions.

Statistics: Data were analyzed by ANOVA with repeated measures as appropriate. Post-hoc analyses were performed using Bonferroni multiple-comparisons procedures. EC50 and maximum response calculations were performed by fitting individual dose-response data sets to a four-parameter logistic function (Hillslope method); y=min+(max204 min)/(1+(x/EC50)^Hillslope). All mRNA fold changes were calculated using the Livak method (54). All analytical comparisons were performed using SigmaStat/SigmaPlot (Systat). All data are presented as mean±sem.

Figure 2:
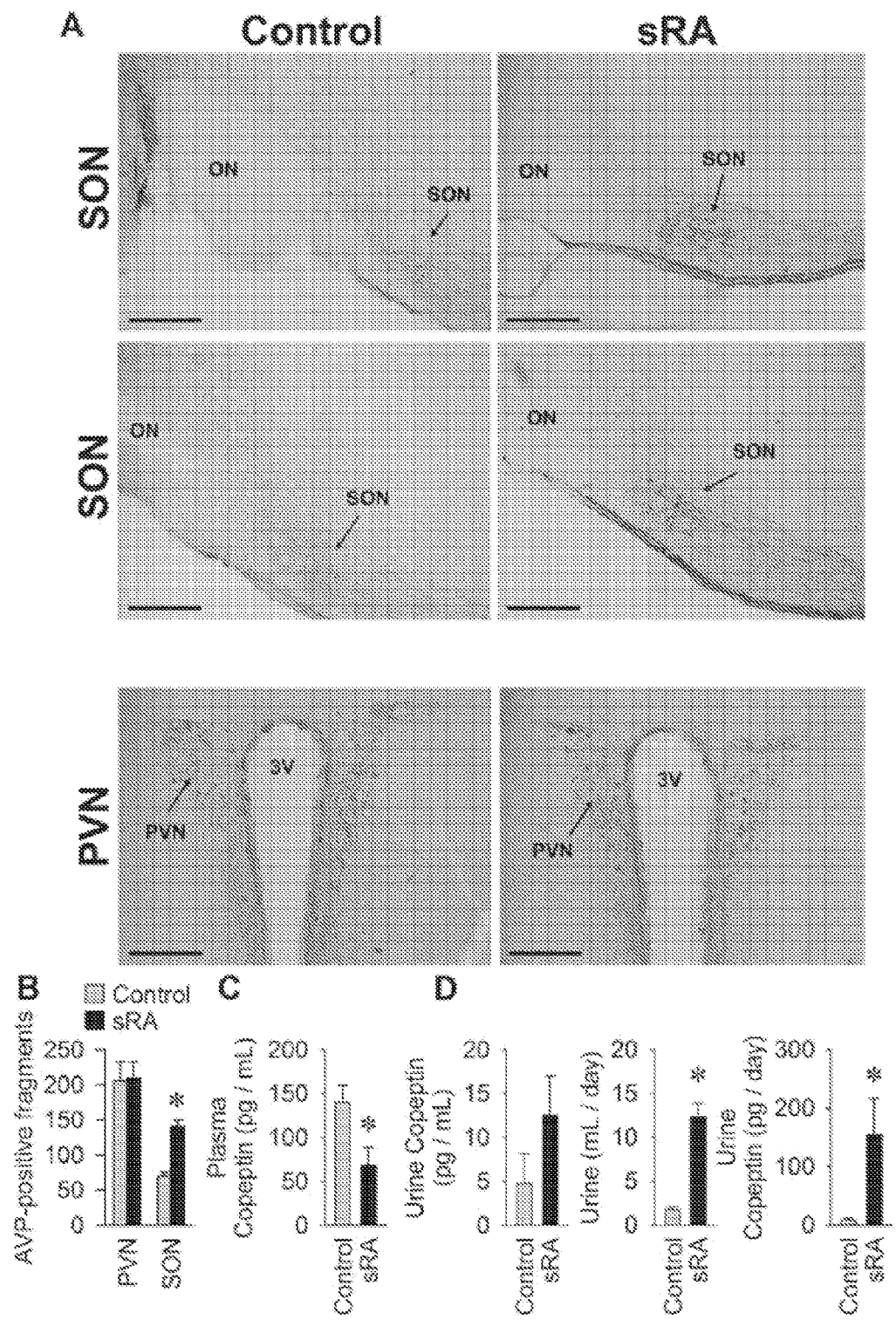
FIG. 2. Elevated vasopressin in sRA mice. A: arginine vasopressin (AVP) immunoreactivity in the supraoptic (SON, top and middle rows, from four separate animals) and paraventricular (PVN, bottom row, from two separate animals) nuclei in female sRA and control animals. Note the increased numbers of strongly immunoreactive AVP neurons in the retrochiasmatic part of the SON in sRA animals. ON, optic tract; 3V, third ventricle. Bars=200 μm. B: total immunoreactive cell fragments per side, greater than 10 μm in diameter, in four serial sections (spaced 200 μm apart) through the PVN and SON of littermate control and sRA mice (n=3 females each group). C: plasma copeptin levels (n=4 male+4 female control, 4 male+4 female sRA). D: urine copeptin concentration, total daily urine volume, and total daily copeptin loss into urine (n=12 male+5 female control, 10 male+7 female sRA). All data are means±SE. *P<0.05 vs. control.

Results:

In both sRA and wild-type animals, AVP immunoreactivity was observed in the cells in the suprachiasmatic (SCN), SON, PVN, and circular nuclei of the hypothalamus as expected (41, 100). AVP-immunoreactive fibers were traceable from the SON and PVN to the median eminence (FIG. 2A). Though there was no obvious difference in the numbers of AVP immunoreactive neurons in the SCN and PVN between sRA and wild-type animals, neuronal and fiber immunoreactivity was consistently denser in the sRA animals. The most striking difference between sRA and control animals was the doubling of the number of AVP immunoreactive neurons detected in the retrochiasmatic part of the SON in sRA animals (FIGS. 2A and B) compared with the retrochiasmatic SON in wild-type animals. Copeptin is the COOH-terminal fragment of the fully translated AVP proprotein and is therefore translated in a 1:1 molar ratio with AVP. Because it exhibits a far greater biological half-life than AVP, it has been proposed as a more reliable measure of chronic AVP release than AVP itself (90). Copeptin levels were significantly reduced in plasma from sRA mice (FIG. 2C). Because of its small size (38 amino acids, 4.22 kDa), however, this protein is rapidly cleared from the plasma by the kidneys. Copeptin concentrations appeared elevated in the urine from sRA mice, though the difference was not significantly different. After we accounted for the grossly elevated (~7-fold) urine production rate of sRA mice, however, it is clear that the total daily copeptin clearance into urine is grossly elevated in sRA mice (~20-fold, FIG. 2D). These data together indicate that there is an approximate 20-fold increase in AVP secretion in sRA mice. This large difference in total daily copeptin loss to urine was still present (8-fold) after normalization for total daily urine creatinine (creatinine: control, 0.20±0.03 vs. sRA, 0.40±0.05 mg/day, P<0.01, and copeptin/creatinine: control, 49±36 vs. sRA, 406±176 pg/mg, P=0.05) or (10-fold) after normalization total daily urine protein (protein: control, 41±4 vs. sRA, 86±9 mg/day, P<0.01, and copeptin/protein: control, 180±100 vs. sRA, 1,845±665 mg/mg, P=0.02).

Figure 3:
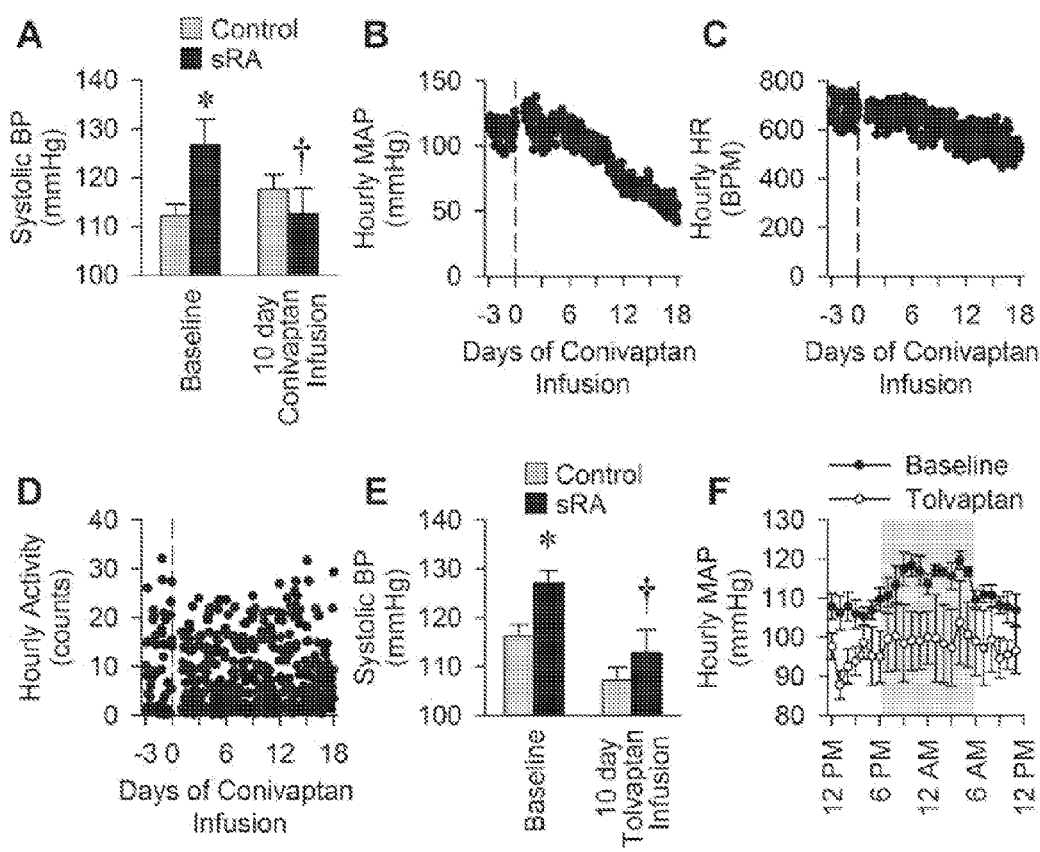
FIG. 3. Blood pressure responses to vasopressin receptor antagonists. A: systolic blood pressure (BP), monitored by tail-cuff, at baseline and with 10 days of chronic subcutaneous infusion (22 ng/h) of the V1A/V2 nonpeptide antagonist conivaptan (n=2 male+4 female control, 2 male+4 female sRA). Hourly telemetric blood pressure (B, MAP) and heart rate (C, HR) recordings for 3 days preceding and 18 days during subcutaneous infusion of the nonselective V1A/V2 receptor antagonist conivaptan (22 ng/h) in a female sRA mouse are shown. D: spontaneous ambulatory physical activity counts during conivaptan infusion experiment (in B and C). E: systolic BP, monitored by tail-cuff, at baseline and with 10 days of chronic subcutaneous infusion (22 ng/h) of the V2-selective antagonist tolvaptan (n=4 male+5 female control, 4 male+6 female sRA). F: hourly average radiotelemetric MAP recordings from (n=4 female) sRA mice at baseline and after 10 days of subcutaneous tolvaptan infusion (Drug X Time, P=0.029). All data are means±SE. *P<0.05 vs. control, †P<0.05 vs. baseline sRA.

Under baseline conditions, sRA mice exhibited a hypertension that was easily detectable by tail-cuff (FIG. 3A). These data replicate our previously published measures of hypertension in this model, as determined by direct cannulas and by radiotelemetry (29, 76). Chronic subcutaneous infusion of the nonselective, nonpeptide AVP V1A/V2 receptor antagonist conivaptan resulted in a complete normalization of the hypertension in sRA mice. Continuous recording of blood pressures in an exemplar sRA mouse at baseline and during 18 days of continuous subcutaneous conivaptan infusion documented a gradual but substantial reduction in blood pressure (FIG. 3B) that was paralleled by a slight reduction in heart rate (FIG. 3C). Importantly, spontaneous physical activity remained normal throughout the recording period, suggesting that the animal was not lethargic or otherwise ill due to the surgery and conivaptan infusion (FIG. 3D).

To dissect the relative contributions of various vasopressin receptor subtypes in the hypertension of sRA mice, we next examined the blood pressure consequences of chronic subcutaneous infusion of the V2-selective antagonist tolvaptan. Chronic infusion of tolvaptan caused a nearly identical normalization of blood pressure (FIG. 3E) to that observed with conivaptan (FIG. 3A). Importantly, this blood pressure reduction was confirmed in a cohort of sRA mice tested using radiotelemetry (FIG. 3F).

Figure 4:
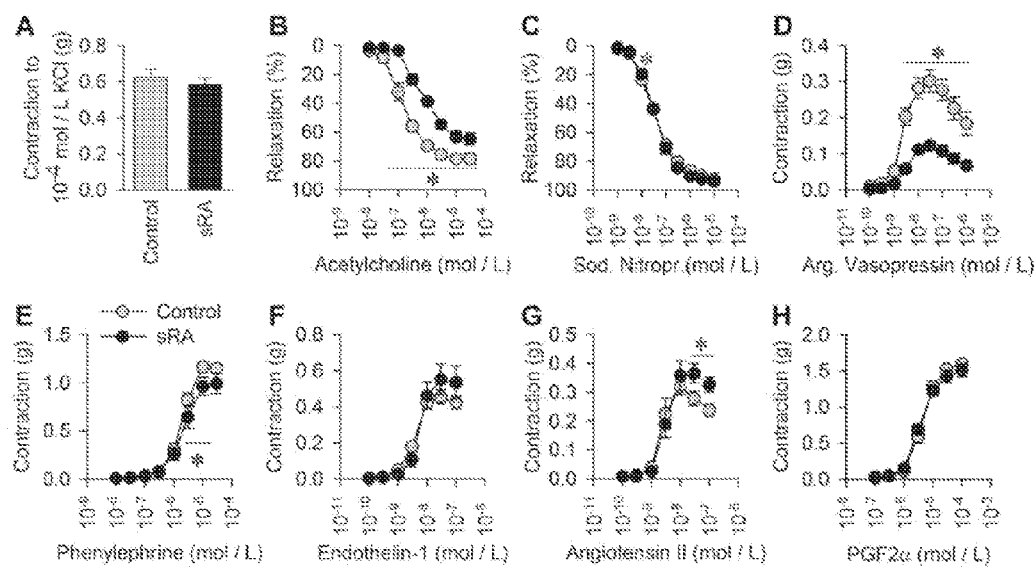
FIG. 4. Vascular reactivity of abdominal aorta. A: maximum contractile response to 100 mmol/l KCl. B and C: relaxation responses to graded doses of acetylcholine and sodium nitroprusside after half-maximal contraction to PGF2α. D-H: contractile responses to graded doses of arginine vasopressin, phenylephrine, endothelin-1, angiotensin II, and prostaglandin-F2α (PGF2α) (n=6 male control, 5 male sRA). All data are means±SE. *P<0.05 vs. control.

Additional evidence for chronic hypertension and vasopressin-specific changes in sRA mice comes from vascular reactivity assays. First, abdominal aortic rings were examined ex vivo for reactivity to selected vasoconstrictor and vasodilator compounds. Aortic rings from sRA mice exhibited normal constrictor responses to potassium chloride (FIG. 4A). Abdominal aortic rings exhibited a robust rightward shift in responses to the vasodilator acetylcholine (Table 2), but normal responses to sodium nitroprusside, indicating endothelial dysfunction typical in chronic hypertension models (FIGS. 4, B and C). Supporting a chronic elevation in AVP levels, abdominal aortas from sRA mice exhibited a robust suppression of constrictor responses to AVP (FIG. 4D), reflected both in a trend toward a rightward (reduced) potency shift and a significant suppression of maximal response (Table 2). No potency or efficacy changes were observed in contractile responses to PE, ET-1, ANG II, or PGF2α (FIG. 4, E-H), suggesting AVP specific changes in the sRA vasculature.

TABLE 2

Potency and efficacy analyses of various vasoactive compounds in abdominal aortas and 2°-branch mesenteric artery of male sRA and control littermate mice.
Table 2. Potency and efficacy analyses of various vasoactive compounds in abdominal aortas and 2°-branch mesenteric artery of male sRA and control littermate mice

| Compound | $EC_{50}$ | | Maximum Response | |
| --- | --- | --- | --- | --- |
| | Control | sRA | Control | sRA |
| Abdominal aorta | nmol/l | nmol/l | g | g |
| Phenylephrine | 1.900 ± 250 | 2.430 ± 620 | 1.18 ± 0.05 | 1.02 ± 0.10 |
| Angiotensin II | 2.26 ± 0.45 | 4.24 ± 1.14 | 0.32 ± 0.03 | 0.38 ± 0.03 |
| Arginine vasopressin | 2.19 ± 0.19 | 3.72 ± 0.73* | 0.29 ± 0.03 | 0.12 ± 0.01† |
| Prostaglandin $F_{2\alpha}$ | 4.600 ± 750 | 3.600 ± 290 | 1.59 ± 0.06 | 1.50 ± 0.10 |
| Endothelin-1 | 3.40 ± 0.33 | 5.19 ± 0.93 | 0.45 ± 0.04 | 0.55 ± 0.09 |
| | nmol/l | nmol/l | % | % |
| Acetylcholine | 130 ± 35 | 879 ± 298* | 78.9 ± 3.3 | 70.4 ± 8.9 |
| Sodium nitroprusside | 29.4 ± 3.7 | 34.2 ± 1.7 | 91.5 ± 0.5 | 93.5 ± 0.8 |
| Mesenteric artery | nmol/l | nmol/l | % | % |
| Phenylephrine | 1.460 ± 660 | 560 ± 80 | 67.3 ± 3.0 | 64.5 ± 4.1 |
| Arginine vasopressin | 0.57 ± 0.15 | 15.89 ± 13.46 | 52.5 ± 3.2 | 17.3 ± 6.5† |
| Endothelin-1 | 1.68 ± 0.43 | 0.45 ± 0.17* | 67.8 ± 4.3 | 58.0 ± 4.6 |

Data are presented as means ± SE. Aortas: Control, n = 6; sRA, n = 5. Mesenteric artery: Control, n = 6; sRA, n = 6.
*P ≤ 0.05, and
†P ≤ 0.001 vs. Control.

Figure 5:
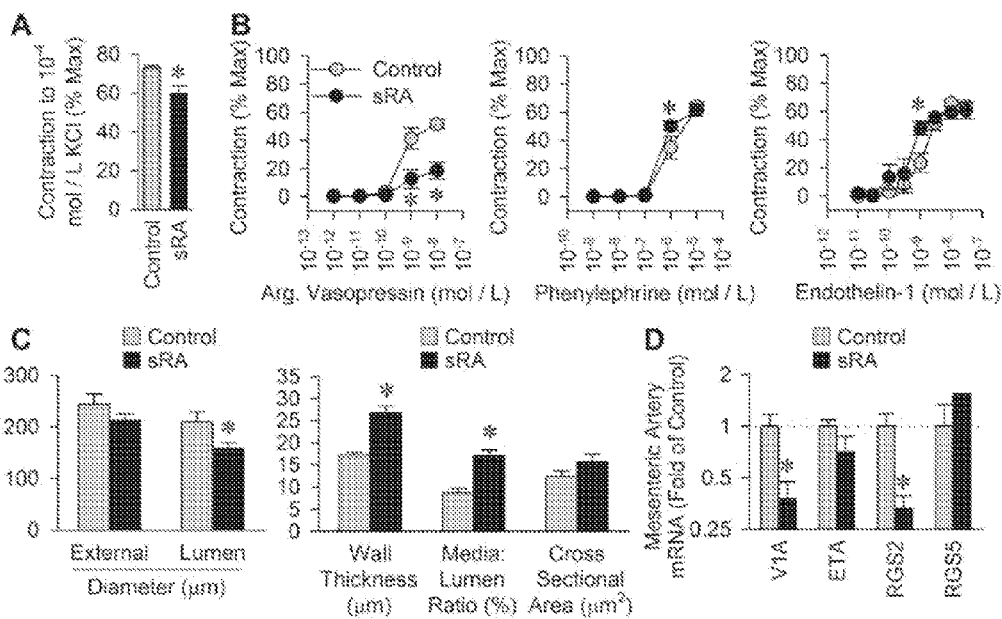
FIG. 5. Mesenteric artery vascular reactivity. A: maximum contractile response to 100 mmol/1 KCl. B: contractile responses to graded doses of arginine vasopressin, phenylephrine, and endothelin-1 (n=6 male control, 6 male sRA). C: external and lumen diameters, wall thickness, media-to-lumen ratio, and cross-sectional area of mesenteric arteries maintained at 75 mmHg lumen pressure, in calcium-free conditions. D: mesenteric artery mRNA expression of the AVP V1A receptor, the endothelin-1 ETA receptor, RGS2, and RGS5 (V1A, RGS2, and RGS5; n=4 male+5 female control, 4 male+3 female sRA. ETA, n=4 male control, 4 male sRA). All data are means±SE. *P<0.05 vs. control.

Acknowledging that smaller arteries are important in controlling peripheral resistance, vascular reactivity of second order branches of mesenteric arteries were next examined using pressurized myography. Mesenteric artery branches exhibited a significant reduction in contractile response to potassium chloride (FIG. 5A); however, normalization of other constrictor responses to this lower KCl response in sRA mice had no qualitative effect on data interpretation (not shown). Similar to abdominal aortic rings, mesenteric arteries from sRA mice exhibited a trend toward a rightward shift and a substantial suppression of maximal response (Table 2) to AVP (FIG. 5B).

Mesenteric arteries exhibited normal contractile responses to PE, with no change in efficacy or potency. In response to ET-1, mesenteric arteries from sRA mice exhibited a normal maximal response and a small but statistically significant leftward potency shift. These data confirm an AVP specific desensitization in smaller arteries of sRA mice, further supporting the conclusion that AVP is chronically elevated in sRA mice. Mesenteric arteries from sRA mice exhibited substantial eutrophic inward remodeling, providing further evidence of chronic hypertension in this model. While no difference in external diameter was detected between control and sRA mice (FIG. 5C), lumen diameter was significantly smaller in sRA mice because of increased wall thickness. This resulted in an increased media-tolumen ratio but no significant change in cross-sectional area.

To explain the reduced vascular reactivity to AVP, we next measured expression of the V1A receptor. Mesenteric arteries from sRA mice exhibited significantly suppressed V1A receptor mRNA but no change in ETA receptor expression (FIG. 5D). Furthermore, there was a selective downregulation of regulator of G protein signaling-2 (RGS2) expression but no change in RGS5 expression.

In contrast to vascular V1A downregulation, renal V2 receptors and aquaporin-2 mRNA levels were unchanged in sRA mice (Table 3). The only renal transporter that showed significant changes in expression in sRA mice was the sodium chloride cotransporter (NCC, 5-fold of control, P<0.05), though the sodium/hydrogen exchanger (NHE) showed a trend toward reduction (NHE3, 0.6-fold of control, P=0.08) and the ENaC-α subunit showed a trend toward elevation (ENaC-α, 10-fold of control, P=0.08). It should be noted that these renal gene expression assays were performed on only male sRA and littermate control mice, and the statistical power is low due to a small number of replicates per group (n=4 each). Thus it is possible that the changes in NHE3 and ENaC-α may both be physiologically significant.

TABLE 3

Renal expression of selected receptors and transporters in sRA and littermate control mice.
Table 3. Renal expression of selected receptors and transporters in sRA and littermate control mice

| Gene | Control (n = 4) | sRA (n = 4) | t-Test P Value |
| --- | --- | --- | --- |
| AVPR2 | 1.000 (0.840-1.191) | 0.778 (0.583-1.038) | 0.425 |
| NCC | 1.000 (0.736-1.359) | 5.232 (3.850-7.112) | 0.009 |
| NHE3 | 1.000 (0.825-1.212) | 0.605 (0.522-0.701) | 0.075 |
| NKCC2 | 1.000 (0.632-1.581) | 0.621 (0.415-0.929) | 0.464 |
| ENaCα | 1.000 (0.468-2.135) | 10.021 (4.556-22.041) | 0.080 |
| ENaCβ | 1.000 (0.657-1.522) | 0.596 (0.282-1.263) | 0.611 |
| ENaCγ | 1.000 (0.669-1.495) | 1.682 (1.120-2.525) | 0.398 |
| Na—K-ATPase-α | 1.000 (0.620-1.613) | 0.819 (0.553-1.215) | 0.744 |
| AQP1 | 1.000 (0.610-1.640) | 0.643 (0.511-0.808) | 0.441 |
| AQP2 | 1.000 (0.747-1.338) | 0.541 (0.440-0.665) | 0.133 |
| AQP3 | 1.000 (0.636-1.571) | 0.317 (0.192-0.524) | 0.640 |
| AQP4 | 1.000 (0.397-2.521) | 0.483 (0.237-0.983) | 0.506 |
| PGES | 1.000 (0.779-1.283) | 0.616 (0.237-1.597) | 0.164 |
| UT1-A | 1.000 (0.486-2.057) | 0.569 (0.406-0.799) | 0.643 |

Data are presented as fold-of-control; means ± SE. See text for abbreviations and more information.

Figure 6:
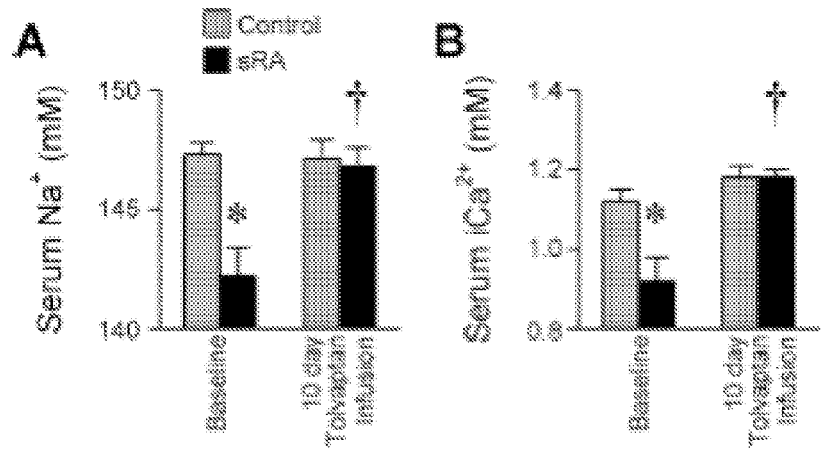
FIG. 6. Serum electrolytes. A: serum sodium concentration. B: serum-ionized calcium concentration (baseline: n=8 male and 12 female control, 5 male and 8 female sRA; tolvaptan: n=4 male and 5 female control, 4 male and 6 female sRA). All data are means±SE. *P<0.05 vs. control. † P<0.05 vs. baseline sRA.

Finally, to more directly probe a V2-mediated mechanism in the cardiovascular phenotypes of sRA mice, we examined blood chemistry responses to tolvaptan (Table 4). We previously documented an approximate 4 mM hyponatremia in sRA mice under baseline conditions (29). Here we determined that sRA mice were hyponatremic (FIG. 6A) and hypocalcemic (FIG. 6B), and chronic tolvaptan delivery corrected both of these imbalances (genotype X drug interaction P<0.05 for both). sRA mice also exhibited alterations in chloride, total CO2, glucose, blood urea nitrogen, creatinine, hematocrit, and anion gap, and whereas tolvaptan treatment did affect some of these endpoints (potassium, chloride, and blood urea nitrogen), it did so in a manner independent of genotype as no genotype X drug interactions were uncovered (Table 4).

TABLE 4

Blood chemistry at baseline or following tolvaptan infusion in sRA and control littermate mice.

| | Females | | | | Males | | | |
| --- | --- | --- | --- | --- | --- | --- | --- | --- |
| | Baseline | | Tolvaptan | | Baseline | | Tolvaptan | |
| Parameter | Control (n = 12) | sRA (n = 8) | Control (n = 5) | sRA (n = 6) | Control (n = 8) | sRA (n = 5) | Control (n = 4) | sRA (n = 4) |
| Females | | | | | | | | |
| Age, wk | 23.5 ± 0.1 | 23.6 ± 0.2 | 22.7 ± 0.2 | 22.6 ± 0.2 | 19.4 ± 1.1 | 18.5 ± 1.3 | 22.5 ± 0.3 | 22.5 ± 0.3 |
| Sodium, mM$^{G,T,G\times T}$ | 147.3 ± 0.7 | 142.6 ± 1.2 | 146.2 ± 0.7 | 146.3 ± 0.7 | 147.4 ± 0.9 | 141.4 ± 2.8 | 48.3 ± 1.3 | 147.5 ± 1.9 |
| Potassium, mM$^T$ | 6.6 ± 0.3 | 6.5 ± 0.5 | 6.4 ± 0.1 | 5.3 ± 0.3 | 6.5 ± 0.5 | 6.8 ± 0.7 | 6.6 ± 0.5 | 5.4 ± 0.1 |
| Chloride, mM$^{G,S,T}$ | 115.7 ± 1.0 | 110.3 ± 1.7 | 112.4 ± 0.5 | 105.2 ± 1.6 | 119.4 ± 2.0 | 115.8 ± 2.2 | 115.5 ± 0.3 | 107.0 ± 2.7 |
| Ionized calcium, mM$^{G,T,G\times T}$ | 1.15 ± 0.04 | 1.01 ± 0.04 | 1.19 ± 0.05 | 1.18 ± 0.03 | 1.07 ± 0.06 | 0.78 ± 0.12 | 1.18 ± 0.04 | 1.18 ± 0.03 |
| Total CO$_2$, mM$^{G,T}$ | 18.4 ± 1.1 | 21.6 ± 2.1 | 24.0 ± 1.1 | 28.8 ± 1.7 | 17.0 ± 1.2 | 18.8 ± 1.7 | 24.0 ± 0.8 | 26.0 ± 3.4 |
| Glucose, mg/dl$^{G,S\times T}$ | 215 ± 8 | 193 ± 16 | 190 ± 13 | 136 ± 15 | 196 ± 11 | 155 ± 16 | 182 ± 7 | 181 ± 28 |
| BUN, mg/dl$^{G,T}$ | 22.4 ± 1.5 | 42.4 ± 4.9 | 18.4 ± 0.9 | 24.5 ± 1.7 | 28.5 ± 4.0 | 40.8 ± 9.0 | 21.5 ± 0.9 | 27.3 ± 2.1 |

TABLE 4-continued

Blood chemistry at baseline or following tolvaptan infusion in sRA and control littermate mice.

| | Females | | | | Males | | | |
| --- | --- | --- | --- | --- | --- | --- | --- | --- |
| | Baseline | | Tolvaptan | | Baseline | | Tolvaptan | |
| Parameter | Control (n = 12) | sRA (n = 8) | Control (n = 5) | sRA (n = 6) | Control (n = 8) | sRA (n = 5) | Control (n = 4) | sRA (n = 4) |
| Crenfinine, mg/dl$^{G}$* | 0.21 ± 0.01 | 0.33 ± 0.06 | 0.24 ± 0.02 | 0.33 ± 0.04 | 0.21 ± 0.01 | 0.24 ± 0.02 | 0.25 ± 0.03 | 0.30 ± 0.04 |
| Hematocrit, % RBC$^{G,G\times S}$ | 45.8 ± 0.5 | 52.6 ± 0.6 | 45.4 ± 0.7 | 49.8 ± 1.1 | 43.8 ± 0.7 | 52.6 ± 0.9 | 43.8 ± 1.1 | 52.0 ± 1.1 |
| Anion gap, mM$^{G,G\times S}$ | 21.2 ± 0.6 | 18.4 ± 1.0 | 17.0 ± 1.5 | 18.5 ± 0.7 | 18.3 ± 1.4 | 14.8 ± 4.4 | 16.3 ± 0.5 | 21.0 ± 2.4 |

Values are means ± SE.
Three-way ANOVA results:
$^{G}$p < 0.05 main effect of genotype,
$^{S}$p < 0.05 main effect of sex,
$^{T}$p < 0.05 main effect of tolveptan (22 ng/h, 10 days sc),
$^{G\times S}$p < 0.05 genotype × sex interaction,
$^{G\times T}$p < 0.05 genotype × tolvaptan interaction,
$^{S\times T}$p < 0.05 sex × tolvaptan interaction.
*Lower detection limit for crestinine assay was 0.20 mg/dl;
values below detection were assigned value of 0.20. All end points were evaluated from check capillary blood collected in lithium-heparin coated tubes and tested using CHEM8+ cartridges in an iSTAT handheld chemistry analyzer (Abbon Labs).

Discussion

Here we examined a unique double-transgenic mouse model to test the hypothesis that AVP is required for the hypertension induced by the brain RAS. Immunohistochemical examination of the brain revealed elevated AVP levels in the retrochiasmatic part of the supraoptic hypothalamic nucleus but no consistent change in PVN immunostaining in sRA mice. Confirming a required role for AVP signaling in the hypertension, chronic blockade of vasopressin V1A/V2 receptors resulted in normalization of blood pressure in sRA mice. While vascular reactivity in multiple arteries to PE, ET-1, ANG II, and PGF2α were largely unchanged in sRA mice, responses to AVP were greatly desensitized. Selective inhibition of V2 receptors had a potent antihypertensive action in sRA mice and normalized the hyponatremia typical of this model. Together, these data strongly support a required role for AVP, acting at V2 receptors, in the maintenance of brain RAS-derived hypertension.

Increased AVP signaling has been suggested as a mechanism for the hypertension in many models. Mice with either tightly regulated or strongly overexpressed transgenic hyperactivity of the RAS throughout the body require elevated AVP signaling to maintain hypertension (19, 61). Deoxycorticosterone acetate (DOCA)-salt hypertension, which is dependent on elevated brain RAS activity (40, 50, 69), also depends on AVP signaling. DOCA-salt treatment results in elevated plasma AVP levels (16, 57, 60, 99). Intracerebroventricular infusion of the angiotensin-converting enzyme inhibitor captopril into rats both prevented and reversed DOCA-salt hypertension and was associated with a reduction in plasma vasopressin levels despite a reduced blood pressure (40). The dependence of DOCA-salt hypertension on AVP has also been demonstrated using AVP-deficient Brattleboro rats, as the hypertensive effects of DOCA-salt are greatly diminished in these animals (16, 106). Complimenting these findings from various hypertensive models, TGR(ASrAOGEN) rats, which exhibit reduced glial production of angiotensinogen, are hypotensive and have reduced plasma AVP levels (79). These animals also exhibit altered patterns of AVP V1A receptor expression within the brain (11), further supporting a brain RAS-AVP interaction. Mice deficient for the V1A AVP receptor are hypotensive, though the relative importance of brain, vascular, cardiac, thrombocyte, and hepatic receptors is unclear (2, 48).

Effects of the RAS on the production and release of AVP were reported as early as 1970, when Bonjour and Melvin (6) demonstrated that peripherally administered renin or angiotensin II resulted in dose-dependent increases in plasma AVP in dogs. Evidence for direct actions of angiotensin on AVP release within the brain was provided by ex vivo experiments using isolated rat neurohypophysis (23). Electrolytic lesion of the subfornical organ (39) or transection of efferent projections from the subfornical organ (47) both attenuate the release of AVP into the plasma in response to intravenous ANG II. Thus the demonstrations here of elevated brain AVP staining and increased daily copeptin (and thereby AVP) release in sRA transgenic mice were expected. Further work is required to causally link specific RAS receptor subtypes to the AVP elevation, as morphological and functional evidence support roles for both AT1 and AT2 receptors in AVP release.

The strongly increased AVP immunoreactivity in the SON implicates ANG II-mediated hyperactivity in the supraopticneurohypophysial pathway as leading to elevated AVP in sRA mice. ANG II injections into the SON depolarize neurosecretory cells (100), ANG II-immunoreactive neurons and axon terminals are found in the rodent SON intermingled with AVP immunoreactive neurons, and ANG II and AVP are colocalized in some neurons (41). It is thus likely that local production and/or actions of ANG II within the SON regulate AVP production and secretion.

AVP is an endogenous agonist for at least four subtypes of receptors. The V1A receptor subtype is primarily found in the vasculature, signals primarily through Gαq, and mediates vasoconstriction. V1A receptors are also present in neurons and appear to signal through cAMP to regulate neuronal function (2, 96). The V1B receptor subtype is primarily found in the brain, signals through Gαq, and stimulates adrenocorticotropic hormone. The V2 receptor subtype is primarily found in the collecting duct of kidney nephrons, signals through Gαs, and stimulates water reabsorption through aquaporin mobilization. There is some evidence for expression of V2 receptors in extrarenal tissues such as lung (22) and cerebellum (45), though their physiological significance in these tissues is unclear. Finally, AVP is also an agonist at the VACM-1 receptor, also known as Cullin-5, where it elicits calcium mobilization in endothelial cells and renal collecting ducts (7, 8). Our determination that mesenteric artery V1A receptors were downregulated in sRA mice but renal V2 receptor expression was unchanged may suggest a greater role for AVP-mediated renal water retention in the hypertension of sRA mice. Though not directly tested herein, this conclusion is supported by the slow time course for the effects of conivaptan (several days of infusion to see an effect, FIG. 3B), the antihypertensive effects of tolvaptan (FIGS. 3, E and F), and the normalization of baseline hyponatremia and hypocalcemia in this model (Table 4 and FIG. 6) that are typical of the syndrome of inappropriate secretion of antidiuretic hormone (SIADH) (25). RGS2 is expressed throughout the cardiovascular system and acts to negatively regulate G$\alpha$q-mediated GPCR signaling, and therefore oppose vasoconstrictor responses (80). Studies in human patients have revealed a negative correlation between RGS2 expression and blood pressure, with hypertensive patients showing reduced RGS2 expression and hypotensive patients exhibiting elevated RGS2 expression (37, 80, 101). A similar correlation is observed in hypertensive animal models (10, 11) and was again observed in the present study (FIG. 5D). RGS2 is known to be regulated in a tissue-specific manner, and within cardiovascular tissues RGS2 is controlled through multiple biphasic mechanisms (104). Acute activation of G$\alpha$q by various hormone/receptor combinations upregulates RGS2 rapidly, possibly to serve as a negative feedback mechanism. In contrast, chronic stimulation of G$\alpha$q systems appears to cause a tonic suppression of RGS2 expression (10, 11, 95, 104). Mice deficient for RGS2 exhibit robust hypertension due to chronic increases in peripheral vasoconstriction (33, 36). Vasopressin-induced calcium transients in vascular smooth muscle cells from RGS2 knockout mice are augmented, highlighting the relationship between RGS2 and AVP signaling, presumably through V1A receptors (92) as these receptors utilize G$\alpha$q signaling (2, 96). RGS2 knockout mice also exhibit substantially greater end-organ damage from chronic hypertension than do wild-type animals (87). RGS2 also attenuates cAMP signaling in the kidney through modulation of adenylyl cyclases (31, 91), which may result in modulation of AVP signaling through V2 receptors, G$\alpha$s, and cAMP. Indeed, modulation of RGS2 greatly affects renal V2 receptor signaling and the renal effects of AVP in vivo (77). Thus it is tempting to speculate that modulation of RGS2 in various tissues, along with elevated AVP signaling, may contribute to the maintenance of hypertension in the context of chronically elevated brain RAS activity. Differential regulation patterns for V1A receptors and V2 receptors in pathological states have previously been described. Gózdz et al. (28) previously demonstrated that in the TGR (mRen2)27 rat model of high-renin hypertension, cardiac V1A receptors are upregulated compared with control Sprague-Dawley rats, while renal V2 receptors are unchanged between strains. Trinder et al. (94) previously demonstrated that in the streptozotocin-injection model of Type 1 diabetes mellitus, rats exhibited reduced hepatic and renal expression of V1 receptors and AVP-induced inositol phosphate production, while renal V2 receptors and AVP-induced cAMP production are again unchanged. Thus our observation that vascular V1A receptors were downregulated and vascular reactivity to AVP was desensitized while renal V2 receptors and their function were largely unchanged is not unprecedented.

Previously, we demonstrated a robust (twofold) elevation in plasma AVP levels in female sRA mice under baseline conditions (collected 4 h into the light phase of a 12:12 light-dark cycle), and this difference was not detected in males (29). The doubling of plasma AVP concentration was achieved in sRA males as well, following a very brief (4 h) water restriction that had no effect on plasma AVP in control males. In the present study we determined that copeptin loss to urine (the major mechanism for clearance of this 4-kDa peptide) was the same in both male and female mice (FIG. 2D). While urine copeptin measures relate to the rate of AVP secretion, direct plasma AVP measures relate to both AVP secretion and degradation/clearance. Thus we now hypothesize that AVP secretion rates are similarly elevated in both male and female sRA mice, but that there exist sex-specific differences in the rates of AVP degradation/clearance. The determination that AVP receptor blockade effectively eliminated hypertension in both sexes in the present study (FIG. 3) further supports this hypothesis. Studies into the sex-specific differences in AVP clearance mechanisms are ongoing.

Perspectives and Significance: Collectively, our data support a model of elevated brain RAS activity driving an increase in AVP secretion. AVP action upon V2 receptors subsequently contributes to elevated blood pressure and hyponatremia. We hypothesize that these effects are mediated through excessive water retention, which when combined with the extreme polydipsia of this model, results in a polyuria phenotype possibly through a pressure-diuresis mechanism. Based on the well-known function of V2 receptors in renal collecting duct aquaporin-2 mobilization, we suspect a renal-mediated mechanism is hyperactive in sRA mice, though we have not here directly examined the localization of the V2 receptors responsible for the observed antihypertensive actions of tolvaptan. These data may support the use of the sRA mouse as an experimental model of the SIADH (25) or other diseases characterized by elevated AVP production or reduced clearance. The brain-specific generation and action of angiotensin peptides is gaining substantial interest for the regulation of cardiovascular function, fluid balance, metabolic control, and even learning and memory. Vasopressin is also well-recognized for its role in fluid balance, blood pressure regulation, and various behaviors (pair bonding, altruism, learning, memory, fluid, and food intake), and its production and release are well known to be stimulated by angiotensins within the brain. Therefore, the implication of vasopressin as a primary mediator of angiotensinergic hypertension simultaneously 1) identifies vasopressin as a possible mediator of other newly recognized functions of the brain RAS (e.g., metabolic control, learning and memory, etc.); and 2) identifies angiotensin-sensitive, vasopressin-producing brain structures (e.g., the supraoptic nucleus) as major cardiovascular regulatory centers that may deserve substantially more investigation for therapeutically targeting hypertension and other disorders, especially in selected human populations with low-renin hypertension (3, 4, 9, 21, 26, 51, 66, 67, 105).

Example 2. Early First Trimester Prediction of Preeclampsia by Copeptin: Is Vasopressin Hypersecretion an Initiating Event in the Pathogenesis of Preeclampsia?

Preeclampsia affects 5-7% of all pregnancies, approximately 300,000 per year in the U.S. Yet, it disproportionately causes 15% of all maternal-fetal morbidity and mortality (78). Preeclampsia is known to cause immediate and long term maternal-fetal morbidities such as fetal growth restriction, maternal-fetal death, and future adult neurological and cardiovascular diseases for mother and child (24, 42, 55, 56, 97, 98). Because its pathogenesis is poorly understood, preventative, therapeutic, and curative modalities for preeclampsia are elusive. This emphasizes the importance of finding appropriate unifying pathways to be able to predict and treat preeclampsia. One potential pathway is the vasopressin pathway.

Vasopressin exhibits a short biological half-life (on the order of 5-20 minutes in blood), which complicates direct measurement of this hormone. Vasopressin is translated in 1:1 stoichiometric ratio with a small, inactive pro-segment, copeptin. Copeptin is eliminated primarily by renal excretion and is very stable in plasma. Consequently, it is a very useful biomarker for vasopressin secretion (3). Zulfikaroglu et al. (108) recently documented a late second/early third trimester elevation in circulating copeptin in preeclamptics. Furthermore, selected populations exhibit vasopressin-dependent hypertension, including African Americans, the elderly, and patients in chronic heart or renal failure (3, 4, 9, 21). These populations are also characterized by low circulating renin-angiotensin system activity. Interestingly, relative to normotensive pregnancies, preeclamptic pregnancies also exhibit reduced circulating activity of the renin-angiotensin system (35). These data lead us to hypothesize a potential causative role for vasopressin hypersecretion in the development of preeclampsia, and the possible utility of copeptin as a novel predictive biomarker for preeclampsia in early pregnancy.

Methods

Biosample and Clinical Data Acquisition: Maternal plasma and clinical patient information were obtained through the University of Iowa IRB-approved (IRB #200910784) Maternal Fetal Tissue Bank (MFTB). In this bank, pregnant women are prospectively recruited from the beginning of their prenatal care. MFTB inclusion criteria include any women >18 years old receiving prenatal care at the University of Iowa Hospitals & Clinics who are English speaking. The MFTB exclusion criteria include prisoners, HIV+ or Hepatitis C positive women. Women who enroll into the MFTB provide a maternal blood sample for research whenever they have clinically indicated blood draws throughout pregnancy. All maternal blood in the MFTB is uniformly processed. Maternal plasma and the buffy coat are isolated, aliquoted, and stored at −80° C. Maternal and neonatal clinical data obtained by the MFTB is obtained via a data extraction from the electronic medical record using standardized data extraction forms. Extracted clinical data is routinely monitored for accuracy and completeness by two of the authors (MKS and DAS). Additional data is also extracted by bioinformatics collaborators from the University of Iowa Institute for Clinical and Translational Science who are able to query the central electronic medical record database.

Cohort Assembly: Inclusion criteria for preeclampsia cases included women who delivered at UIHC, were enrolled in the MFTB, and carried the diagnosis of preeclampsia at the time of delivery. The diagnosis and classification of cases of preeclampsia were based on the standard American College of Obstetrics and Gynecology (ACOG) definitions for analysis (1). These cases were identified by cross-referencing the MFTB database with the bioinformatics query of mild and severe preeclampsia ICD-9 codes (642.4x, 642.5x, 642.7x, 642.9x) of bank participants at the time of delivery. The electronic medical record of each potential case was evaluated to confirm the diagnosis of preeclampsia by the ACOG definitions. Maternal age-matched plasma samples and corresponding clinical data for the control population were obtained by utilizing the MFTB database. The gestational age at the time of the collection of the samples were classified by trimesters: first trimester (<13 completed gestational weeks), second trimester (13-26 completed gestational weeks), and third trimester (>26 weeks).

Procedures: All maternal plasma copeptin concentrations were measured in duplicate using a commercial enzyme-linked immunosorbent assay (ELISA) specific for human copeptin (USCN Life Science, Inc, Houston, Tex.). The assay was performed according to the manufacturer's instructions. The minimum detectable dose of human copeptin for this assay was 5.4 pg/mL. The intra-assay coefficient of variation is <10% and the interassay coefficient of variation is <12%. To examine if renal function or vasopressin degradation throughout pregnancy affected copeptin concentration, plasma Cystatin C (Sigma-Aldrich, St. Louis, Mo.) and vasopressinase (LNPEP, USCN Life Science, Inc, Houston, Tex.) were measured in duplicate in all samples utilizing commercial ELISA kits.

Animal Studies: Female C57Bl/6J mice were obtained from Jackson Laboratories between 8-12 weeks of age. Osmotic minipumps infusing vasopressin (240 ng/hr) or saline vehicle were inserted into the subcutaneous space via incision between the scapulae. Following three days of recovery, females were mated with male C57Bl/6J mice. Presence of a vaginal plug indicated gestational day 0.5. Blood pressure was tracked before mating and throughout gestation by tail-cuff plethysmography. On gestational day 18, females were sacrificed for necropsy. Pup weight was recorded. Dam kidney sections were generated and imaged by electron microscopy by the University of Iowa Department of Pathology. All studies were approved by the University of Iowa Animal Care and Use Committee (ACURF #1211239).

Statistical Analyses: The major aim of this study was to determine if differences in first-trimester copeptin concentrations between pregnant women who did and did not develop preeclampsia predicted the development of preeclampsia. Using the smallest effect size in late gestation maternal plasma copeptin concentrations from Zulfikaroglu et al. between control (310 pg/mL) and mild preeclamptics (620 pg/mL) with the largest reported standard deviation of 180 pg/mL, power of 80% and $\alpha=0.05$, only 7 participants per group are required. In order to account for a parsimonious, mixed effects regression model of 3 variables, a minimum of 30 samples per group was utilized.

All statistical analyses were performed with SigmaPlot 12.0 software (Systat Software, Inc, California) and confirmed using SAS 9.1 software (SAS Institute Inc, Cary, N.C.). Stepwise regression was used to develop a model for this dataset and to evaluate for possible confounding. Logistic regression models were constructed and receiver operating characteristic curves were constructed for regression diagnostics. In addition, chi square or Fisher exact test was utilized for categorical variables. For continuous variables, the Student's t-test or if criteria for normality were not met, Mann-Whitney test was utilized. All variables were tested at significance level of 0.05.

Results

A total of 30 individual control (C) subjects and 51 individual preeclamptic (P) subjects were utilized in this study. A full complement of first (C=12, P=20), second (C=10, P=20), and third (C=30, P=51), trimester plasma samples were not available for each participant. Maternal age, gravida, body mass index, percentage of those with chronic hypertension and preexisting diabetes were similar between the control and preeclamptic groups (Table 5). In addition, the racial distribution between these groups were also similar and reflective of the Iowa population with a predominantly Caucasian populace based on current Iowa census data. Of these maternal characteristics, only history of preeclampsia was significantly higher in the control group vs. the preeclamptic group (53.3% vs. 17.7%, p=0.002). When evaluating the delivery characteristics between the two groups (Table 5), typical differences were observed between groups. The preeclampsia group exhibited a significantly lower gestational age at delivery (36.2 vs. 38.7 weeks, P=0.001), higher percentage of twin gestation (21.6 vs. 0%, P=0.016), and lower birthweight (2777.0 vs. 3424.0 grams, P=0.0001). These findings are consistent with the known morbidities associated with preeclampsia: higher rate of preterm delivery, higher rate of twin gestation, and lower birthweight due to vascular causes and earlier delivery (85).

Further, we determined if clinically significant covariates would alter the association of the development of preeclampsia and copeptin concentration at particular trimesters. Logistic regression models were constructed with the diagnosis of preeclampsia as the dependent variable. Participants were dichotomized according to being above or below the determined cutoff for a particular trimester. Using the trimester specific cutoff values (first trimester: 1018 pg/mL, second trimester: 943 pg/mL, third trimester: 860 pg/mL), models were generated using the status of being above or below the cutoff as an independent variable while controlling for clinically significant covariates. After controlling for clinically significant covariates such as maternal age, body mass index, diabetes, chronic hypertension, history of preeclampsia, and twin gestation, copeptin concentration was still significantly associated with the development of preeclamp-

TABLE 5

Group Characteristics.

| Group Characteristics | Nonpregnant (n = 33) | Control (n = 31) | Preeclampsia (n = 50) | P Value |
|---|---|---|---|---|
| Maternal Characteristics | | | | |
| Maternal Age (years) | 31.4 | 30.0 | 30.0 | 0.86 |
| Gravida | 1.3 | 2.6 | 2.7 | <0.001 |
| Body Mass Index (kg/m$^2$) | 29.6 | 30.4 | 31.9 | 0.48 |
| Chronic Essential Hypertension | 9.1% | 29.0% | 20.0% | 0.13 ($\chi^2$ = 4.1) |
| Preexisting Diabetes | 3.0% | 9.7% | 10.0% | 0.47 ($\chi^2$ = 1.5) |
| History of Preeclampsia | 0% | 51.6% | 18.0% | 0.002 ($\chi^2$ = 25.7) |
| Race: Caucasian, not Hispanic | 90.9% | 87.1% | 90.0% | 0.63 ($\chi^2$ = 6.2) |
| Race: Hispanic | 0% | 6.5% | 4.0% | 0.63 ($\chi^2$ = 6.2) |
| Race: Asian | 6.1% | 3.2% | 0% | 0.63 ($\chi^2$ = 6.2) |
| Race: African-American | 3.0% | 3.2% | 2.1% | 0.63 ($\chi^2$ = 6.2) |
| Pregnancy Characteristics | | | | |
| Gestational Age at Delivery (wk) | | 38.7 | 36.2 | 0.001 |
| Mode of Delivery: Vaginal | | 53.3% | 34.0% | 0.09 ($\chi^2$ = 4.75) |
| Mode of Delivery: C-Section | | 40.0% | 64.0% | 0.09 ($\chi^2$ = 4.75) |
| Mode of Delivery: Operative Vaginal Delivery | | 6.7% | 2.0% | 0.09 ($\chi^2$ = 4.75) |
| Twin Gestation | | 0% | 21.6% | 0.016 ($\chi^2$ = 5.76) |
| Birthweight (grams) | | 3424.0 | 2777.0 | <0.001 |
| 1 minute APGAR | | 7.2 | 7.3 | 0.95 |
| 5 minute APGAR | | 8.7 | 8.5 | 0.49 |

Figure 7:
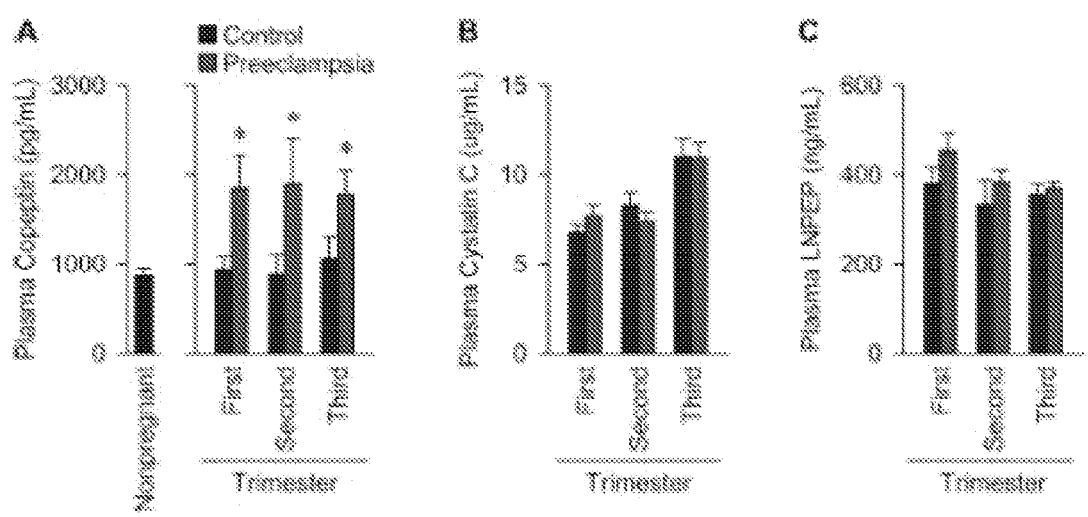
FIG. 7. Maternal plasma copeptin, cystatin C, and vasopressinase (LNPEP) protein concentrations by trimester of pregnancy. (A) Compared to non(pregnant women and women with normotensive pregnancies, plasma copeptin concentrations were significantly elevated in all three trimesters of pregnancy in women that eventually developed preeclampsia. Importantly, copeptin was grossly elevated as early as the sixth week of pregnancy. (B) Plasma cystatin C was affected by gestational age in a similar manner in women that did or did not experience preeclampsia. (C) Plasma LNPEP was essentially unchanged by gestational age and by preeclampsia status. *P<0.05 vs. non-pregnant and gestational time-matched control pregnant samples.

As seen in FIG. 7A, measurement of the maternal plasma copeptin concentration revealed a significant increase in mean copeptin in pregnant women who developed preeclampsia in comparison with control, non-preeclamptic women in the first trimester (2045 vs. 903 pg/mL, p=0.008), second trimester (1806 vs. 706 pg/mL, p=0.001), and third trimester (1890 vs. 822 pg/mL, p=0.0006). These group differences in plasma copeptin are likely not associated with changes in renal function and vasopressin degradation as measured by plasma Cystatin C and Vasopressinase respectively as these levels were similar between groups in each trimester (FIGS. 7B and 7C).

Figure 8:
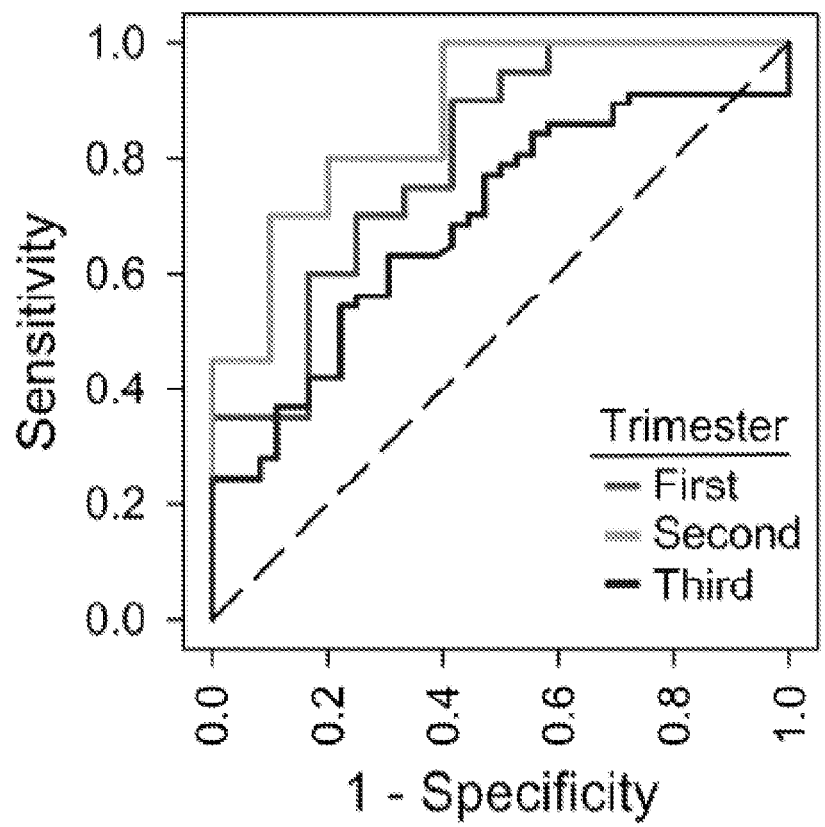
FIG. 8. Predictive value of maternal plasma copeptin without adjustment for any covariates. Receiver operator characteristic (ROC) analyses of the utility of copeptin, without correction for covariates, as a predictive tool for the subsequent development of preeclampsia.
Figure 9:
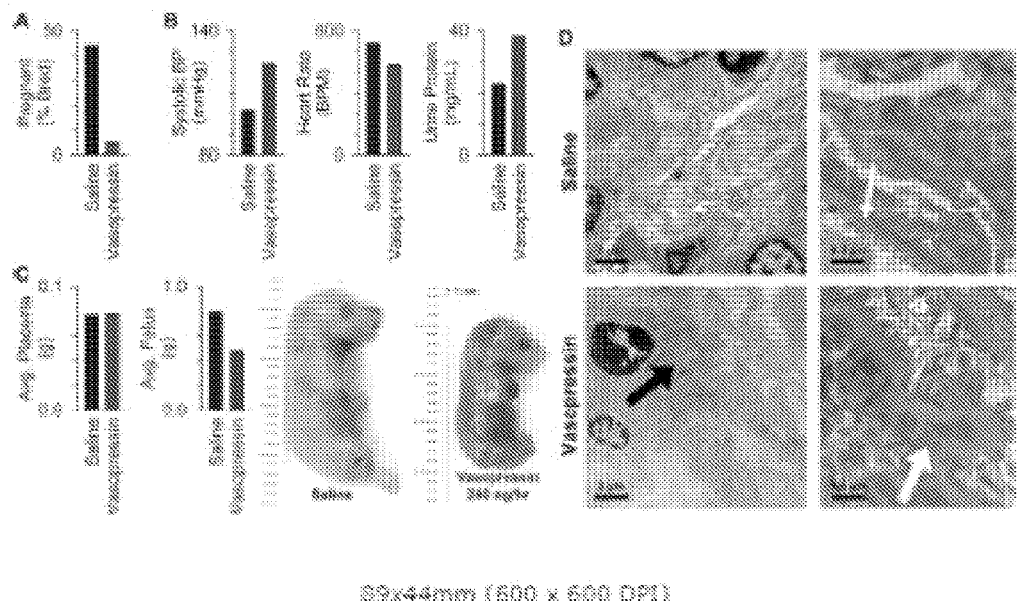
FIG. 9. Sufficiency of vasopressin to induce preeclampsia-like phenotypes in C57Bl/6J mice. (A) Vasopressin infusion significantly reduced fecundity. X2 P<0.005. (B) Vasopressin infusion appears to induce hypertension and proteinuria in pregnant mice. (C) Images of example gestational day 18 fetuses, illustrating substantial fetal growth restriction by vasopressin infusion. (D) Electron micrographs of renal cortex, illustrating glomerular endotheliosis. Top two panels are from a saline infused animal which had a glomerular basement membrane thickness within normal limits (thin white arrow). The bottom two panels are from an animal that received vasopressin infusion. Redundant endothelial cell membrane is present (thick black arrow), and basement membranes are markedly thickened with electron dense material (thick white arrow).

Given this significant increase in copeptin, we constructed receiver operating characteristic curves for each trimester to interrogate if maternal plasma copeptinconcentration was predictive of the development of preeclampsia. Furthermore, optimal copeptin concentration cutoffs were determined from these curves. As seen in FIG. 8, the ROCs demonstrated significant areas under the curve in the first trimester (AUC=0.80, p=0.005), second trimester (AUC=0.87, p=0.002), and third trimester (AUC=0.72, p=0.004). These data indicate that the mean maternal plasma copeptin concentration is predictive of the development of preeclampsia.

sia in the first, second and third trimester (Table 6). With the exception of the model including the second trimester [copeptin] cutoff and a history of preeclampsia, all models significantly predict the development of preeclampsia. These results confirm our observation that copeptin concentration is significantly elevated in the plasma of pregnant women who will develop preeclampsia in comparison to controls. This robust elevation in copeptin concentration occurs early in the first trimester and remains elevated throughout pregnancy despite potential confounding effects of clinically significant obstetrical and vascular covariates. Finally, we observed that the chronic elevation of vasopressin during pregnancy is sufficient to cause preeclampsia-like phenotypes in mice. Vasopressin infusion significantly reduced the rate of pregnancy (FIG. 9A), highlighting a role for this hormone in reproductive pathophysiology. Vasopressin infusion during successful pregnancy resulted in cardinal preeclampsia phenotypes, including a robust increase in blood pressure and apparent proteinuria (FIG. 9B), substantial fetal growth restriction (FIG. 9C) and pathognomic glomerular endotheliosis (FIG. 9D).

TABLE 6

Using first, second and third trimester specific cutoffs, maternal plasma copeptin remains significantly predictive of the development of preeclampsia despite adjustment of significant clinical covariates.

|  | Beta [Copeptin] | Adjusted Odds Ratio | P Value |
|---|---|---|---|
| First Trimester Model [Copeptin] Cutoff = 1018 pg/mL |  |  |  |
| 1st Trimester [Copeptin] | 1.8 | 6.05 | 0.025 |
| 1st Trimester [Copeptin] + Maternal Age | 2.2 | 9.03 | 0.018 |
| 1st Trimester [Copeptin] + Body Mass Index | 1.8 | 6.05 | 0.026 |
| 1st Trimester [Copeptin] + Diabetes | 2.1 | 8.17 | 0.024 |
| 1st Trimester [Copeptin] + Chronic Essential Hypertension | 1.9 | 6.69 | 0.024 |
| 1st Trimester [Copeptin] + History of Preeclampsia | 2.6 | 13.46 | 0.028 |
| 1st Trimester [Copeptin] + Twin Gestation | 1.6 | 4.95 | 0.05 |
| Second Trimester Model [Copeptin] Cutoff = 943 pg/mL |  |  |  |
| 2nd Trimester [Copeptin] | 2.8 | 16.44 | <0.001 |
| 2nd Trimester [Copeptin] + Maternal Age | 3.1 | 22.20 | <0.001 |
| 2nd Trimester [Copeptin] + Body Mass Index | 2.9 | 18.17 | <0.001 |
| 2nd Trimester [Copeptin] + Diabetes | 2.8 | 16.44 | <0.001 |
| 2nd Trimester [Copeptin] + Chronic Essential Hypertension | 3.2 | 24.53 | <0.001 |
| 2nd Trimester [Copeptin] + History of Preeclampsia | 20 | 485165195.41 | 0.995 |
| 2nd Trimester [Copeptin] + Twin Gestation | 3.1 | 22.20 | 0.0047 |
| Third Trimester Model [Copeptin] Cutoff = 860 pg/mL |  |  |  |
| 3rd Trimester [Copeptin] | 1.3 | 3.67 | 0.017 |
| 3rd Trimester [Copeptin] + Maternal Age | 1.3 | 3.67 | 0.017 |
| 3rd Trimester [Copeptin] + Body Mass Index | 1.4 | 4.06 | 0.012 |
| 3rd Trimester [Copeptin] + Diabetes | 1.7 | 5.47 | 0.008 |
| 3rd Trimester [Copeptin] + Chronic Essential Hypertension | 1.3 | 3.67 | 0.017 |
| 3rd Trimester [Copeptin] + History of Preeclampsia | 1.3 | 3.67 | 0.038 |
| 3rd Trimester [Copeptin] + Twin Gestation | 1.6 | 4.95 | 0.008 |

Our data demonstrates that copeptin is a strong predictor of the development of preeclampsia. More importantly, it is predictive of the development of preeclampsia throughout pregnancy as early as the sixth gestational week. This finding represents a major advance in the prediction of preeclampsia. Currently, anti-angiogenic factors like sFLT-1 and Endoglin are elevated as early as 12 weeks before the diagnosis of preeclampsia (52). Follow up analyses of sFLT-1, Endoglin, and other anti-angiogenic factors suggest that testing characteristics of these factors are poor in application to clinical practice (46). Furthermore, a limitation of these factors is that the significant changes in antiangiogenic factors overall have been reported to occur only as early as the second trimester.

In recent years, substantial effort has been invested to identify first trimester predictors of preeclampsia. These investigations have included first trimester circulating hyperglycosylated human chorionic gonadotropin (hCG) (43), Interleukin-1β (83), high sensitivity C-reactive protein (44), and Pregnancy-associated plasma protein-A (PAPPA) (17). These factors have been shown to be poor to moderately predictive of preeclampsia. Given the promise of antiangiogenic markers in the pathogenesis of preeclampsia, they have been investigated in the first trimester. In conjunction with uterine artery Doppler (UAD) analyses, these factors have been shown to only be moderately predictive (AUC=0.74) of preeclampsia (64). An elevated uterine artery Doppler pulsatile index in the first trimester is correlated with the development of preeclampsia. Poon et al. demonstrated that UAD coupled with maternal history and aneuploidy markers in the first trimester can be very predictive of preeclampsia with AUC=0.96. In and of itself, UADs have an AUC=0.91 (71, 72). Although this may be a powerful tool, reliable UAD requires substantial training for sonographers to decrease significant interassay variability through verified programs such as the Fetal Medicine Foundation (68). Such training may not be as available in all hospital settings. Clearly, there is utility in finding a simple predictor of preeclampsia as early in pregnancy as possible, and copeptin represents the first simple and individually predictive biomarker. Coupling plasma copeptin measures with other known first-trimester assays may further increase predictive power. Multiple processes involving placental dysregulation, endothelial cell dysfunction, immunology, oxidative stress, altered vascular biology, and angiogenesis make finding a singular cause of preeclampsia nearly impossible. As preeclampsia is a disease resulting from multiple pathways, the development of a predictive model and the search for a therapeutic pathway for preeclampsia treatment may need to come from the upstream regulators or inducers of these multiple pathways. Vasopressin sits at the crux of many of these pathways. The acknowledgement of copeptin, and thereby vasopressin secretion, as a novel, very early-pregnancy diagnostic biomarker for preeclampsia, plus results from our vasopressin-infused mouse model collectively support the hypothesis that elevated vasopressin secretion in early pregnancy may contribute to the development of preeclampsia. Arginine vasopressin is a peptide hormone synthesized primarily within magnocellular neurons of the supraoptic nucleus and paraventricular nuclei of the brain, though it is produced by selected peripheral tissues in small quantities. Axonal projections from magnocellular neurons comprise the posterior pituitary gland, and upon stimulation vasopressin is released into the circulation. Vasopressin then acts upon multiple receptor types to ultimately increase blood volume, vascular constriction, and reduce osmolality (75).

The connection of vasopressin to the pathogenesis of preeclampsia is strengthened by the immunoactive nature of vasopressin and the immunologic initiating events of preeclampsia. As reviewed by Russell and Walley (75), and by Chikanza and Grossman (12), vasopressin has a variety of immunomodulatory effects. Depending on site of action and dose, vasopressin is known to affect and be affected by tumor necrosis factor-α, interleukin-1β, interferon-γ, β-endorphin, and prostaglandin E2—many of which are altered in preeclampsia. Vasopressin is known to stimulate the autologous mixed lymphocyte response. Vasopressin is produced by, and acts upon, human T cells, B cells, and monocytes/macrophages. High doses of vasopressin cause an amplification of prostaglandin E2 synthesis by human dermal fibroblasts. Further, vasopressin-deficient hypertension Brattleboro rats exhibit substantial changes in circulating immune cell populations and function, including increased neutrophils. These data suggest a potential link between the elevated vasopressin secretion in early pregnancy observed in the present study with excessive peripheral immune activation, and the subsequent development of preeclampsia. Based on our data and others, we therefore posit that vasopressin may play an important role in initiating the immunologic milieu that precipitates preeclampsia.

Our study has benefited from the high quality of clinical data and biosample fidelity provided by the Maternal Fetal Tissue Bank. Furthermore, our study was strengthened by being appropriately powered to evaluate our desired outcomes. One weakness of our study is the predominantly Caucasian population in Iowa. Even though the relationship of copeptin and preeclampsia is robust after clinical covariate adjustment, we are not appropriately powered to analyze the variance due to race. A larger sample size would be necessary for that analysis despite finding significant covariate adjusted associations.

The temporal organization of molecular events and clinical associations that define preeclampsia has been somewhat muddled to date, as essentially all known mechanisms occur or develop in rapid succession during late-pregnancy. Our data clearly demonstrate an early-pregnancy elevation in vasopressin secretion, thus aligning all other known mechanisms as potential targets of vasopressin action. These results highlight the utility of plasma vasopressin/copeptin measurements in the prediction of preeclampsia, and are consistent with a potential causative role for vasopressin in preeclampsia. While our data from mice demonstrate the sufficiency of vasopressin to cause preeclampsia-like phenotypes, future studies are required to elucidate the tissues, receptors, and mechanisms that mediate the induction of preeclampsia by vasopressin. Substantial clinical studies are required to assess the necessity of vasopressin signaling for the development of preeclampsia, and the utility of targeting this system to treat the disorder. Finally, additional investigations will be required to identify the mechanisms that induce excessive vasopressin secretion, to better understand the event(s) that initiate preeclampsia.

Example 3. Vasopressin Infusion Causes Dose-Dependent Increase In Late-Pregnancy Blood Pressure Applicants envisioned that chronic infusion of vasopressin during pregnancy will increase blood pressure, as experienced by subjects suffering from preeclampsia.

Method: Wildtype C57Bl/6J female mice were chronically infused with varied doses of arginine vasopressin (Sigma-Aldrich), via subcutaneous osmotic minipumps (Alzet), for three days preceding mating, then through gestational day 16. Mice were first acclimated to the restraint devices used for recordings for one week ("week −3") before data recordings began. Blood pressure was assessed daily for two weeks preceding minipump implantation, through gestational day 16. Blood pressure was measured using tail-cuff plethysmography (Visitech). On any given recording day, the mouse was restrained and lightly warmed throughout the (30 min) recording period. Thirty consecutive 1 min inflation/deflation cycles were performed and successful pressure determinations were averaged within recording period for each mouse. Data sets from individual days with fewer than 10 successful determinations were excluded from analyses. Daily blood pressure values were averaged within animal for each week for statistical comparisons.

Figure 10:
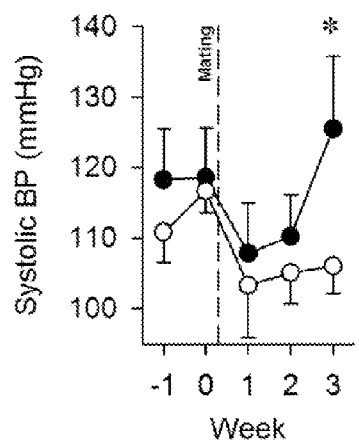
FIG. 10. Chronic vasopressin (AVP) infusion causes a dose- and time-dependent increase in blood pressure during pregnancy. Chronic subcutaneous infusion of AVP at 24 ng/hr causes a late-pregnancy increase in blood pressure that is not achieved by a 10-fold lower infusion rate (2.4 ng/hr).

Results: Blood pressure was indistinguishable among groups for the two weeks preceding pump implantation and mating, and again for the first two weeks of pregnancy (FIG. 10). During the third week of pregnancy (gestational days 14-16, "week 3"), mice infused with vasopressin at 24 ng/hr, s.c. demonstrated a significantly ($P=0.03$ by Tukey multiple-comparisons procedure) increased blood pressure compared to pregnant mice infused with only 2.4 ng/hr, s.c. vasopressin.

Discussion: Pregnancy is typically accompanied by a slow reduction, then normalization of blood pressure. In contrast, preeclamptic pregnancies exhibit relatively normal patterns of blood pressure control in early trimesters, which are then followed by a rapid onset of hypertension in the third trimester. The data presented here illustrate the sufficiency of vasopressin infusion (in a dose- and time-dependent manner) to increase blood pressure during pregnancy. Notably, this increase in pressure occurs specifically in late pregnancy, which closely matches the time course of preeclampsia progression in humans. These data bolster the assertion that vasopressin infusion represents the first (and currently, the only) animal model of the early-pregnancy events that lead to preeclampsia, and that vasopressin hypersecretion/infusion is capable of inducing preeclampsia.

These conclusions are consistent with the concept that inhibiting vasopressin production/release/steady-state/action may represent a novel therapeutic route to prevent and treat preeclampsia and/or reduce the severity of the disease.

Example 4. Vasopressin Infusion During Pregnancy in Mice Results in Substantial Intrauterine Growth Restriction and Spontaneous Fetal Resorption Chronic infusion of vasopressin at 24 ng/hr, s.c. throughout pregnancy (3 days preceding through GD18) causes interrupted or restricted fetoplacental development, a hallmark phenotype of preeclamptic pregnancies.

Methods: Nine adult wildtype female mice were obtained from in-house breeding colonies that are based on the C57Bl/6 background strain. Three days before breeding, females were implanted with subcutaneous osmotic minipumps (Alzet) to continuously deliver arginine vasopressin (AVP, Sigma-Aldrich) at 24 ng/hr. Females were mated for two consecutive nights with wildtype male C57BL/6J males purchased from Jackson Laboratories. GD1 was defined based upon the presence of a vaginal sperm plug. On gestational day 18, female mice were sacrificed by CO2 asphyxiation, and fetuses and fetoplacental units were isolated by blunt dissection.

Figure 11:
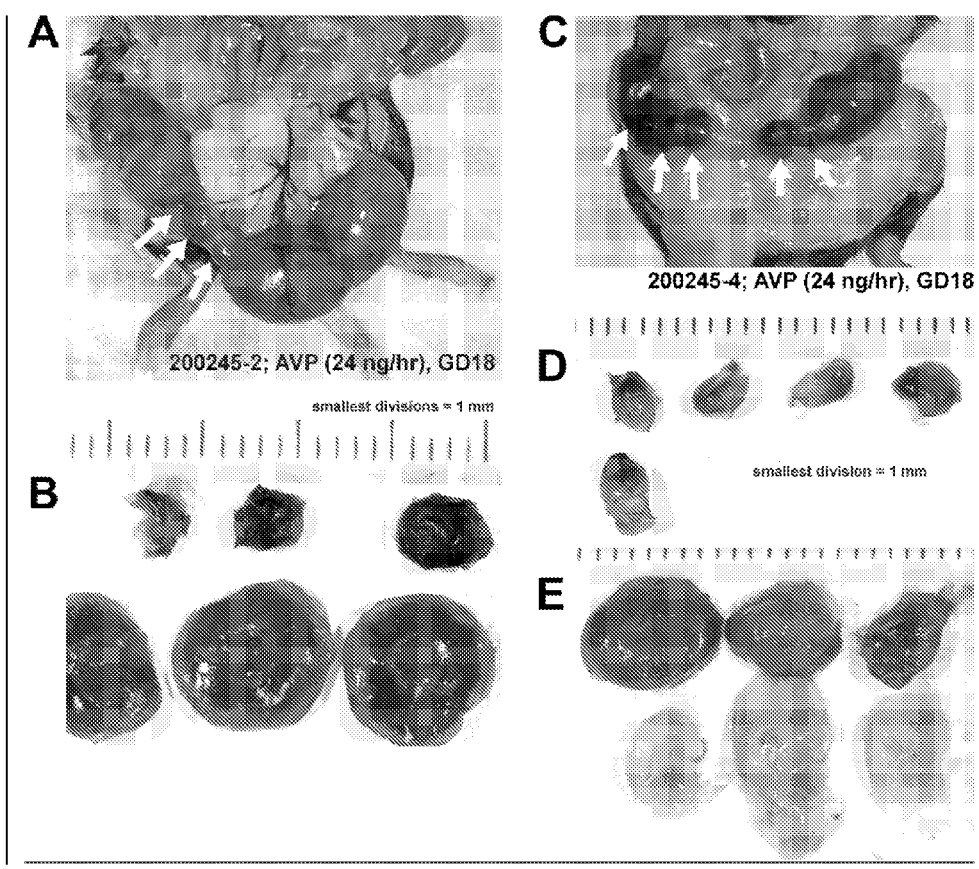
FIG. 11. Effects of 24 ng/hr AVP infusion throughout pregnancy on fetal development. (A) Photo of uterus and fetuses in situ on GD18 of a wildtype mouse chronically infused with AVP. White arrows identify three reabsorbed fetal/placental units within the uterus. (B) Magnified images of the six placentas from the pregnant mouse in panel A, illustrating the necrotic nature and small size of the three placentas identified in panel A. (C) Photo of uterus and fetuses in situ on GD18 of a second wildtype mouse chronically infused with AVP. White arrows identify five reabsorbed fetal/placental units. (D) Magnified images of the five placentas identified in panel C. (E) Magnified images of the three thriving fetuses and placentas from the pregnancy identified in panel C. Notably the fetuses are smaller than normal placentas (not shown) and even smaller than other growth-restricted placentas in panel B. Also, fetuses from this pregnancy are substantially smaller than historical, normal GD18 pups (each would normally reach ~20 mm from nose to anus by this gestational age).

Results: Six of the nine female mice became pregnant despite the limited mating time-course. Of these six dams, one (200372-3) carried seven fetuses of relatively normal size compared to fetuses of historical mice (0.90-0.99 grams/fetus for C57BL/6 mice, and 0.97-1.00 grams/fetus for DBA/1 mice, (10)). Regardless, as a group, fetuses across all six pregnancies were substantially smaller than historical controls (10) ($0.4929\pm0.0397$ gram/fetus, n=48, P<0.0001 by one-sample t-test against 0.90 gram historical control C57Bl/6 fetus mass; summarized in Table 7). Three dams carried a mixture of growth-restricted fetuses plus fetoplacental units that had necrotized and begun the resorption process (see FIG. 11 for examples), bringing the total number of resorbed fetoplacental units to 17%.

Discussion: Intrauterine growth restriction and fetal resorption are unusual events in unchallenged wildtype mice. Gendron demonstrated that roughly 2% of fetoplacental units undergo resorption in CFW/SWxDBA/2 crosses (27). Sulila reported a resorption frequency of between 4-7% for C57 mice and 0-13% for DBA mice (86). Mattsson reported a resorption frequency of between 3-7% for C57 females mated to CBA males (58). In the current experiment, 17% of fetoplacental units were resorbed. Five of six pregnant mice exhibited abnormal pregnancies involving growth restriction and/or fetal resorption (e.g.—in the two pregnancies depicted in FIG. 11, eight of fourteen fetoplacental units were resorbed, and all eight remaining fetuses were growth-restricted), far beyond the expected rate of such events. These data highlight the powerfully negative effects that elevated vasopressin can have on the fetoplacental unit during pregnancy, and are therefore consistent with our assertion that vasopressin is sufficient to cause key phenotypes of preeclampsia such as growth restriction or death.

minipumps (Alzet) were implanted to deliver vasopressin at 0.24, 2.4, or 24 ng/hr (six mice each group). After three days, mice were mated with wildtype C57BL/6J male mice for one night (thereby defining gestational day zero). On GD16, mice were placed into single-mouse metabolic cages (Nalgene) to collect urine for two consecutive nights. On GD18, mice were sacrificed to quantify and collect fetuses and placentas. Urine protein was assessed by commercially-available BCA assay (Pierce).

Figure 12:
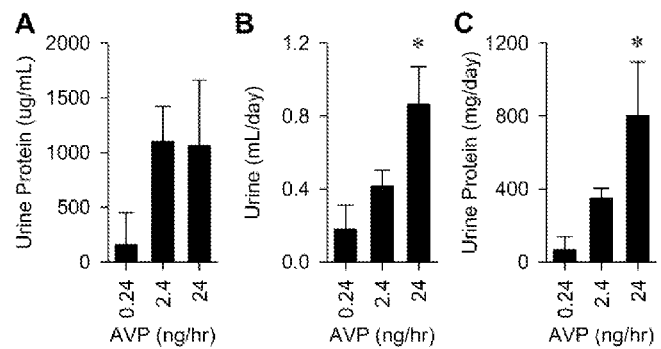
FIG. 12. Vasopressin infusion causes dose-dependent proteinuria at GD17-GD18 in pregnant C57BL/6J female mice. (A) 24-hour urine protein concentration. One-way ANOVA P=0.322. (B) 24-hour urine volume. One-way ANOVA P=0.046. (C) 24-hour total urine protein. One-way ANOVA P=0.030. For all panels, * P<0.05 versus 0.24 ng/hr dose by Tukey multiple-comparisons procedure.

Results: Of the six mice infused with each dose of vasopressin, three became pregnant during 24 ng/hr infusion; five became pregnant during 2.4 ng/hr infusion; and two became pregnant during 0.24 ng/hr infusion. In pregnant mice, urine protein content was elevated in a dose-dependent manner with vasopressin infusion (FIG. 12). Similar effects were observed in non-pregnant mice (not shown).

Figure 13:
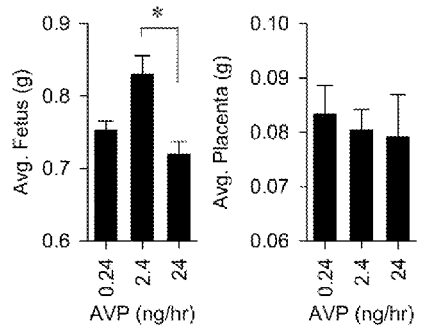
FIG. 13. Vasopressin infusion causes dose-dependent intrauterine growth restriction in pregnant C57BL/6J female mice. (A) Average fetus masses. One-way ANOVA P=0.012. (B) Average placental masses. One-way ANOVA P=0.897. For both panels, * P<0.05 versus 2.4 ng/hr dose by Tukey multiple-comparisons procedure.

Fetal masses were significantly suppressed for dams infused with 24 ng/hr vasopressin compared to 2.4 ng/hr vasopressin (FIG. 13). Placental masses were indistinguishable across treatment groups.

Figure 14:
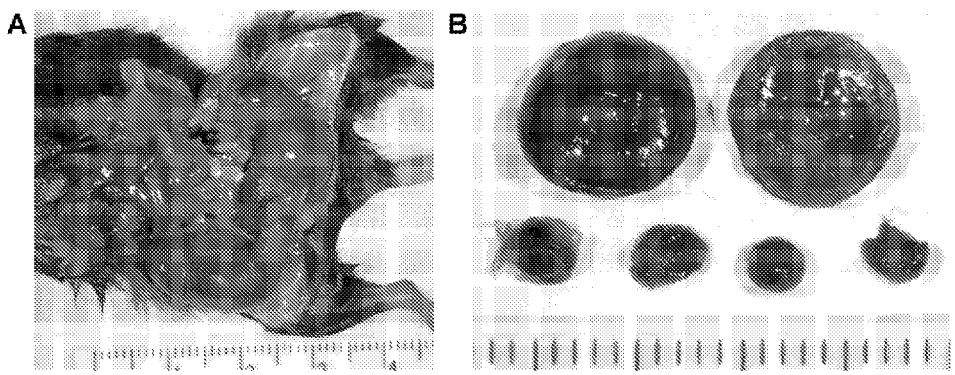
FIG. 14. Preterm (GD17) labor in 24 ng/hr vasopressin-infused C57BL/6J mouse. On gestational day 17, one mouse that had been chronically infused with vasopressin (24 ng/hr, s.c.) exhibited preterm labor. One pup had been born and the mother had consumed the placenta and part of the pup before the delivery was noted by laboratory staff. The second pup was stuck in the birth canal and required technician intervention. The animal was immediately sacrificed and photographs were obtained of the uterus and fetoplacental units. (A) In situ image of the uterus containing two developing fetuses and four partially resorbed fetoplacental units. (B) Magnified image of placentas from two developing fetuses and four partially resorbed fetoplacental units. Same ruler shown in both photos; smallest division is 1 mm.

In the 24 ng/hr vasopressin infusion group, one pregnant mouse exhibited preterm labor (FIG. 14). This dam began delivering pups spontaneously on gestational day 17. Labo-

TABLE 7

Raw fetal and placental masses from dams chronically infused with vasopressin (24 ng/hr).

| | \multicolumn{12}{c}{Mouse} | | | | | | | | | | | |
|---|---|---|---|---|---|---|---|---|---|---|---|---|
| | 200372-3 | | 200301-4 | | 200245-2 | | 200245-4 | | 200301-2 | | 200357-1 | |
| | \multicolumn{12}{c}{Mating code} | | | | | | | | | | | |
| | HD9 | | HD3 | | HD4 | | HD5 | | HD2 | | HD6 | |
| | Fetus | Placenta | Fetus | Placenta | Fetus | Placenta | Fetus | Placenta | Fetus | Placenta | Fetus | Placenta |
| | 0.9287 | 0.0725 | 0.2866 | 0.0315 | 0.7964 | 0.0679 | 0.0154 | 0.0494 | 0.3756 | 0.0687 | 0.4865 | 0.0599 |
| | 1.0395 | 0.0866 | 0.2599 | 0.0762 | 0.5962 | 0.0629 | 0.0699 | 0.0410 | 0.3352 | 0.0810 | 0.4962 | 0.0709 |
| | 1.1359 | 0.0753 | 0.3328 | 0.0747 | 0.8258 | 0.0860 | 0.0261 | 0.0261 | 0.3805 | 0.0828 | 0.4780 | 0.0663 |
| | 1.0723 | 0.0810 | 0.3609 | 0.0876 | 0.8183 | 0.0898 | | <0.01 | 0.3954 | 0.0796 | 0.4092 | 0.0509 |
| | 1.0064 | 0.0706 | 0.3085 | 0.0710 | 0.8336 | 0.0770 | | <0.01 | 0.3094 | 0.0638 | 0.4962 | 0.0480 |
| | 0.9679 | 0.0702 | 0.3087 | 0.0789 | | 0.0070 | | <0.01 | 0.3777 | 0.0840 | 0.4543 | 0.0648 |
| | 0.9034 | 0.0766 | 0.2955 | 0.0620 | | 0.0157 | | <0.01 | 0.4078 | 0.0936 | 0.5241 | 0.0767 |
| | | | 0.3356 | 0.0687 | | 0.0324 | | <0.01 | 0.3880 | 0.0477 | 0.4999 | 0.0678 |
| | | | 0.3129 | 0.0669 | | 0.0433 | | | 0.3971 | 0.0827 | 0.4399 | 0.0426 |
| | | | 0.3034 | 0.0714 | | | | | | | 0.4501 | 0.0471 |
| | | | 0.3086 | 0.0640 | | | | | | | 0.5057 | 0.0569 |
| | | | 0.2516 | 0.0529 | | | | | | | 0.3521 | 0.0499 |
| | | | | | | | | | | | | 0.0067 |
| Count | 7 | 7 | 12 | 12 | 5 | 9 | 3 | 8 | 9 | 9 | 12 | 13 |
| Avg mass (g) | 1.0077 | 0.0761 | 0.3054 | 0.0672 | 0.7741 | 0.0536 | 0.0371 | 0.0388 | 0.3741 | 0.0760 | 0.4660 | 0.0545 |
| sam | 0.0310 | 0.0023 | 0.0088 | 0.0041 | 0.0449 | 0.0101 | 0.0167 | 0.0068 | 0.0106 | 0.0046 | 0.0140 | 0.0049 |

| | Fetus | Placenta | Resorb |
|---|---|---|---|
| Total count | 48 | 53 | 10 (17%) |
| Avg mass (g) | 0.4929 | 0.0628 | |
| sem | 0.0397 | 0.0028 | |

Example 5. Chronic Infusion of Vasopressin During Pregnancy in C57BL/6J Female Mice Results in Dose-Dependent Proteinuria and Intrauterine Growth Restriction Hypothesis: Chronic infusion of vasopressin during pregnancy will induce proteinuria and intrauterine growth restriction, hallmark phenotypes of preeclampsia.

Method: Eighteen female C57BL/6J mice were obtained from the Jackson Laboratories. Subcutaneous osmotic ratory personnel intervened as quickly as possible to sacrifice the dam, to collect placentas and fetuses and to quantify the frequency of resorbed fetoplacental units.

Discussion: Vasopressin infusion during pregnancy resulted in a dose-dependent increase in severity of proteinuria. Further, the current cohort of vasopressin-infused dams carried growth-restricted fetuses. Specifically, the highest vasopressin dose resulted in greater growth restriction than the medium and lowest doses, but notably all three groups exhibit substantially suppressed fetal masses compared to historical data for C57BL/6 mice (0.9-1.0 grams, (27, 58, 86)).

Preterm labor is an extremely rare event in non-human animals such as mice (74). Thus the induction of preterm labor in one of the high-dose vasopressin infused dams is very notable. Together, these data illustrate that elevated vasopressin levels during pregnancy cause major phenotypes of preeclampsia including proteinuria (and thereby kidney damage), intrauterine growth restriction, and even preterm labor.

Example 6. Inhibition of Vasopressin Secretion by Tetrahydrobiopterin (BH4)

Summary: Inhibition of vasopressin production & secretion may represent a novel therapeutic approach to prevent or treat preeclampsia. We examined the utility of daily BH4 treatment (once daily injection, 10 mg/kg/day, i.p.) to inhibit vasopressin secretion in mice.

Background & Hypothesis: Double-transgenic "sRA" mice express human renin via the neuron-specific synapsin promoter, and human angiotensinogen via its own promoter (29, 76). This results in chronic increases in the generation of angiotensin peptides within the brain, which results in polydipsia, polyuria, and elevated resting metabolic rate. sRA mice also exhibit robust hypertension that is mediated through, and dependent upon, gross elevations in vasopressin secretion rates (53). Notably sRA mice maintain a baseline hyponatremia, underscoring the concept that the source of stimulation of vasopressin hypersecretion in this model is independent of dehydration.

BH4 is used clinically to treat phenylketonuria (PKU), and is marked under the names "Kuvan" and "Sapropterin." BH4 has previously been shown to interfere with vasopressin regulation in the neurohypophysis. In isolated neurointermediate lobes, BH4 reduces vasopressin content under baseline and potassium-stimulated conditions. In rats, BH4 reduces neurohypophysial vasopressin under euhydrated but not dehydrated conditions (13, 14). Together these results suggest that BH4 specifically modulates hypothalamic vasospressin production to selected (non-dehydration) stimuli.

As preeclampsia is characterized as a state of elevated vasopressin secretion in the absence of dehydration stimuli, we propose the general hypothesis that BH4 will reduce vasopressin secretion during preeclampsia. Specifically, here we hypothesized that BH4 treatment would reduce vasopressin levels in sRA mice.

Methods: Double-transgenic sRA mice and littermate controls were placed into single-mouse metabolic cages (Nalgene), and maintained on a 12:12 light:dark cycle at 22° C. with ad libitum access to standard chow (Teklad 7013) and water. Mice were injected once daily (i.p.) with BH4 to achieve 10 mg/kg/day. On the fourth day, mice were sacrificed by $CO_2$ asphyxiation and trunk blood was collected into lithium heparin-coated tubes and placed on ice between 11:30 AM and 1:00 PM (5.5 to 7 hours into the light phase of the standard light cycle). Blood was then centrifuged at 2,000×g for 20 minutes. Plasma was collected and stored at −80° C. until analysis. Plasma samples were analyzed for vasopressin using a commercially-available ELISA kit (Cayman, catalog #583951), according to the manufacturer's instructions. Results falling outside the range of the standard curve (>3,000 pg/mL or <23.4 pg/mL) were set to the maximum or minimum (3,000 or 23.4 pg/mL), respectively, for statistical comparisons. Data were analyzed by three-way ANOVA followed by Tukey all-pairwise multiple comparison procedures.

Figure 15:
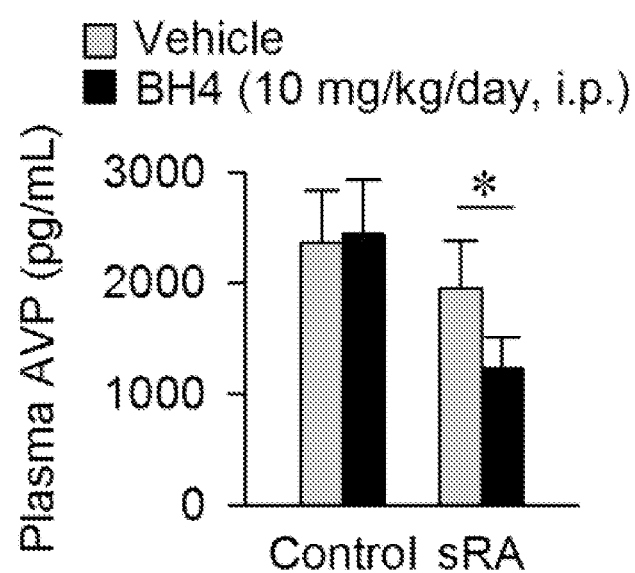
FIG. 15. Plasma vasopressin (AVP) levels in control and double-transgenic sRA mice. Steady-state AVP levels were unchanged in control littermate mice with BH4 treatment, however three days of BH4 (10 mg/kg/day, i.p.) significantly (*P=0.017) reduced steady-state AVP levels in sRA mice. Control+Vehicle n=6 (2 male, 4 female), Control+BH4 n=7 (3 male, 4 female), sRA+Vehicle n=8 (3 male, 5 female), sRA+BH4 n=10 (3 male, 7 female).

Results: Plasma vasopressin values were indistinguishable in water-replete control and littermate sRA mice treated with vehicle for three days. This is similar to our previous demonstration that steady-state plasma levels of vasopressin are relatively normal or only slightly elevated in water-replete sRA mice, with females exhibiting a small elevation and males exhibiting no change (29). Treatment of control mice with BH4 for three days had no effect on steady-state AVP levels. In contrast, treatment of sRA mice with BH4 for three days caused a significant (P=0.017) reduction in plasma AVP levels (FIG. 15).

Conclusion: From these data we conclude that steady-state levels of AVP are significantly reduced in sRA mice following a relatively short-term treatment with BH4. For this preliminary study we used the dose of BH4 that is used for human patients suffering from phenylketonuria (10 mg/kg/day), despite the elevated metabolism exhibited by mice. Further, the short timecourse of treatment (3 days) was selected based on the pharmacokinetics previously demonstrated for humans (3). Thus, it would be reasonable to believe that similar or greater efficacy would be observed in human patients.

Collectively, these data are consistent with the hypothesis that elevated (dehydration-independent) vasopressin secretion can be countered by administration of BH4. These data support the hypothesis that BH4 or related compounds represent a novel therapeutic intervention to suppress preeclampsia-related elevations in vasopressin secretion. Thus, in light of our demonstration that elevated vasopressin is predictive of preeclampsia in humans and sufficient to phenocopy preeclampsia in mice, BH4 and related compounds delivered to a pregnant patient may represent a novel therapeutic intervention to reduce the incidence and/or severity of preeclampsia.

REFERENCES

1. ACOG practice bulletin. Diagnosis and management of preeclampsia and eclampsia. Number 33, January 2002. *Obstetrics and gynecology* 99: 159-167, 2002.
2. Aoyagi T, Koshimizu T A, and Tanoue A. Vasopressin regulation of blood pressure and volume: findings from V1a receptor-deficient mice. *Kidney international* 76: 1035-1039, 2009.
3. Argent N B, Burrell L M, Goodship T H, Wilkinson R, and Baylis P H. Osmoregulation of thirst and vasopressin release in severe chronic renal failure. *Kidney international* 39: 295-300, 1991.
4. Bakris G, Bursztyn M, Gavras I, Bresnahan M, and Gavras H. Role of vasopressin in essential hypertension: racial differences. *Journal of hypertension* 15: 545-550, 1997.
5. Balanescu S, Kopp P, Gaskill M B, Morgenthaler N G, Schindler C, and Rutishauser J. Correlation of plasma copeptin and vasopressin concentrations in hypo-, iso-, and hyperosmolar States. *The Journal of clinical endocrinology and metabolism* 96: 1046-1052, 2011.
6. Bonjour J P and Malvin R L. Stimulation of ADH release by the renin-angiotensin system. *The American journal of physiology* 218: 1555-1559, 1970.
7. Burnatowska-Hledin M, Zeneberg A, Roulo A, Grobe J, Zhao P, Lelkes P I, Clare P, and Barney C. Expression of VACM-1 protein in cultured rat adrenal endothelial cells 7. is linked to the cell cycle. *Endothelium: journal of endothelial cell research* 8: 49-63, 2001.
8. Burnatowska-Hledin M, Zhao P, Capps B, Poel A, Parmelee K, Mungall C, Sharangpani A, and Listenberger L. VACM-1, a cullin gene family member, regulates cellular signaling. *American journal of physiology Cell physiology* 279: C266-273, 2000.
9. Burrell L M, Risvanis J, Johnston C I, Naitoh M, and Balding L C. Vasopressin receptor antagonism—a therapeutic option in heart failure and hypertension. *Experimental physiology* 85 Spec No: 259s-265s, 2000.
10. Cabo L A, Pagnin E, Davis P A, Sartori M, Ceolotto G, Pessina A C, and Semplicini A. Increased expression of regulator of G protein signaling-2 (RGS-2) in Bartter's/Gitelman's syndrome. A role in the control of vascular tone and implication for hypertension. *The Journal of clinical endocrinology and metabolism* 89: 4153-4157, 2004.
11. Campos L A, Couto A S, Iliescu R, Santos J A, Santos R A, Ganten D, Campagnole-Santos M J, Bader M, and Baltatu O. Differential regulation of central vasopressin receptors in transgenic rats with low brain angiotensinogen. *Regulatory peptides* 119: 177-182, 2004.
12. Chikanza I C, Petrou P, and Chrousos G. Perturbations of arginine vasopressin secretion during inflammatory stress. Pathophysiologic implications. *Annals of the New York Academy of Sciences* 917: 825-834, 2000.
13. Ciosek J and Guzek J W. (6R)-5,6,7,8-tetrahydro-alpha-biopterin affects vasopressin and oxytocin release from rat neurointermediate lobe in vitro. *Experimental and clinical endocrinology* 95: 287-291, 1990.
14. Ciosek J, Guzek J W, and Orlowska-Majdak M. Neurohypophysial vasopressin and oxytocin as influenced by (6R)-5,6,7,8-tetrahydro-alpha-biopterin in euhydrated and dehydrated rats. *Biological chemistry Hoppe-Seyler* 373: 1079-1083, 1992.
15. Coleman C G, Anrather J, Iadecola C, and Pickel V M. Angiotensin II type 2 receptors have a major somatodendritic distribution in vasopressin-containing neurons in the mouse hypothalamic paraventricular nucleus. *Neuroscience* 163: 129-142, 2009.
16. Crofton J T, Share L, Shade R E, Lee-Kwon W J, Manning M, and Sawyer W H. The importance of vasopressin in the development and maintenance of DOC-salt hypertension in the rat. *Hypertension* 1: 31-38, 1979.
17. D'Antonio F, Rijo C, Thilaganathan B, Akolekar R, Khalil A, Papageourgiou A, and Bhide A. Association between first-trimester maternal serum pregnancy-associated plasma protein-A and obstetric complications. *Prenatal diagnosis* 33: 839-847, 2013.
18. da Silva A Q, Fontes M A, and Kanagy N L. Chronic infusion of angiotensin receptor antagonists in the hypothalamic paraventricular nucleus prevents hypertension in a rat model of sleep apnea. *Brain research* 1368: 231-238, 2011.
19. Davisson R L, Yang G, Beltz T G, Cassell M D, Johnson A K, and Sigmund C D. The brain renin-angiotensin system contributes to the hypertension in mice containing both the human renin and human angiotensinogen transgenes. *Circulation research* 83: 1047-1058, 1998.
20. de Oliveira-Sales E B, Nishi E E, Boim M A, Dolnikoff M S, Bergamaschi C T, and Campos R R. Upregulation of AT1R and iNOS in the rostral ventrolateral medulla (RVLM) is essential for the sympathetic hyperactivity and hypertension in the 2K-1C Wistar rat model. *American journal of hypertension* 23: 708-715, 2010.
21. de Paula R B, Plavnik F L, Rodrigues C I, Neves Fde A, Kohlmann O, Jr., Ribeiro A B, Gavras I, and Gavras H. Contribution of vasopressin to orthostatic blood pressure maintenance in essential hypertension. *American journal of hypertension* 6: 794-798, 1993.
22. Fay M J, Du J, Yu X, and North W G. Evidence for expression of vasopressin V2 receptor mRNA in human lung. *Peptides* 17: 477-481, 1996.
23. Gagnon D J, Cousineau D, and Boucher P J. Release of vasopressin by angiotensin II and prostaglandin E2 from the rat neuro-hypophysis in vitro. *Life sciences* 12: 487-497, 1973.
24. Garovic V D and Hayman S R. Hypertension in pregnancy: an emerging risk factor for cardiovascular disease. *Nature clinical practice Nephrology* 3: 613-622, 2007.
25. Gassanov N, Semmo N, Semmo M, Nia A M, Fuhr U, and Er F. Arginine vasopressin (AVP) and treatment with arginine vasopressin receptor antagonists (vaptans) in congestive heart failure, liver cirrhosis and syndrome of inappropriate antidiuretic hormone secretion (SIADH). *European journal of clinical pharmacology* 67: 333-346, 2011.
26. Gavras H. Pressor systems in hypertension and congestive heart failure. Role of vasopressin. *Hypertension* 16: 587-593, 1990.
27. Gendron R L, Nestel F P, Lapp W S, and Baines M G. Lipopolysaccharide-induced fetal resorption in mice is associated with the intrauterine production of tumour necrosis factor-alpha. *Journal of reproduction and fertility* 90: 395-402, 1990.
28. Gozdz A, Szczepanska-Sadowska E, Szczepanska K, Maslinski W, and Luszczyk B. Vasopressin V1a, V1b and V2 receptors mRNA in the kidney and heart of the renin transgenic TGR(mRen2)27 and Sprague Dawley rats. *Journal of physiology and pharmacology: an official journal of the Polish Physiological Society* 53: 349-357, 2002.
29. Grobe J L, Grobe C L, Beltz T G, Westphal S G, Morgan D A, Xu D, de Lange W J, Li H, Sakai K, Thedens D R, Cassis L A, Rahmouni K, Mark A L, Johnson A K, and Sigmund C D. The brain Renin-angiotensin system controls divergent efferent mechanisms to regulate fluid and energy balance. *Cell metabolism* 12: 431-442, 2010.
30. Grobe J L, Xu D, and Sigmund C D. An intracellular renin-angiotensin system in neurons: fact, hypothesis, or fantasy. *Physiology (Bethesda, Md.)* 23: 187-193, 2008.
31. Gu S, Anton A, Salim S, Blumer K J, Dessauer C W, and Heximer S P. Alternative translation initiation of human regulators of G-protein signaling-2 yields a set of functionally distinct proteins. *Molecular pharmacology* 73: 1-11, 2008.
32. Halabi C M, Beyer A M, de Lange W J, Keen H L, Baumbach G L, Faraci F M, and Sigmund C D. Interference with PPAR gamma function in smooth muscle causes vascular dysfunction and hypertension. *Cell metabolism* 7: 215-226, 2008.
33. Hao J, Michalek C, Zhang W, Zhu M, Xu X, and Mende U. Regulation of cardiomyocyte signaling by RGS proteins: differential selectivity towards G proteins and susceptibility to regulation. *Journal of molecular and cellular cardiology* 41: 51-61, 2006.
34. Head G A and Mayorov D N. Central angiotensin and baroreceptor control of circulation. *Annals of the New York Academy of Sciences* 940: 361-379, 2001.
35. Herse F, Dechend R, Harsem N K, Wallukat G, Janke J, Qadri F, Hering L, Muller D N, Luft F C, and Staff A C.

Dysregulation of the circulating and tissue-based renin-angiotensin system in preeclampsia. *Hypertension* 49: 604-611, 2007.
36. Heximer S P, Knutsen R H, Sun X, Kaltenbronn K M, Rhee M H, Peng N, Oliveira-dos-Santos A, Penninger J M, Muslin A J, Steinberg T H, Wyss J M, Mecham R P, and Blumer K J. Hypertension and prolonged vasoconstrictor signaling in RGS2-deficient mice. *The Journal of clinical investigation* 111: 445-452, 2003.
37. Heximer S P, Watson N, Linder M E, Blumer K J, and Hepler J R. RGS2/G0S8 is a selective inhibitor of Gqalpha function. *Proceedings of the National Academy of Sciences of the United States of America* 94: 14389-14393, 1997.
38. Huang B S and Leenen F H. Both brain angiotensin II and "ouabain" contribute to sympathoexcitation and hypertension in Dahl S rats on high salt intake. *Hypertension* 32: 1028-1033, 1998.
39. Iovino M and Steardo L. Vasopressin release to central and peripheral angiotensin II in rats with lesions of the subfornical organ. *Brain research* 322: 365-368, 1984.
40. Itaya Y, Suzuki H, Matsukawa S, Kondo K, and Saruta T. Central renin-angiotensin system and the pathogenesis of DOCA-salt hypertension in rats. *The American journal of physiology* 251: H261-268, 1986.
41. Johren O, Imboden H, Hauser W, Maye I, Sanvitto G L, and Saavedra J M. Localization of angiotensin-converting enzyme, angiotensin II, angiotensin II receptor subtypes, and vasopressin in the mouse hypothalamus. *Brain research* 757: 218-227, 1997.
42. Kajantie E, Eriksson J G, Osmond C, Thornburg K, and Barker D J. Pre-eclampsia is associated with increased risk of stroke in the adult offspring: the Helsinki birth cohort study. *Stroke; a journal of cerebral circulation* 40: 1176-1180, 2009.
43. Karahasanovic A, Sorensen S, and Nilas L. First trimester pregnancy-associated plasma protein A and human chorionic gonadotropin-beta in early and late pre-eclampsia. *Clinical chemistry and laboratory medicine: CCLM/FESCC:* 1-5, 2013.
44. Kashanian M, Aghbali F, and Mahali N. Evaluation of the diagnostic value of the first-trimester maternal serum high-sensitivity C-reactive protein level for prediction of pre-eclampsia. *The journal of obstetrics and gynaecology research* 39: 1549-1554, 2013.
45. Kato Y, Igarashi N, Hirasawa A, Tsujimoto G, and Kobayashi M. Distribution and developmental changes in vasopressin V2 receptor mRNA in rat brain. *Differentiation; research in biological diversity* 59: 163-169, 1995.
46. Kleinrouweler C E, Wiegerinck M M, Ris-Stalpers C, Bossuyt P M, van der Post J A, von Dadelszen P, Mol B W, and Pajkrt E. Accuracy of circulating placental growth factor, vascular endothelial growth factor, soluble fms-like tyrosine kinase 1 and soluble endoglin in the prediction of pre-eclampsia: a systematic review and meta-analysis. *BJOG: an international journal of obstetrics and gynaecology* 119: 778-787, 2012.
47. Knepel W, Nutto D, and Meyer D K. Effect of transection of subfornical organ efferent projections on vasopressin release induced by angiotensin or isoprenaline in the rat. *Brain research* 248: 180-184, 1982.
48. Koshimizu T A, Nasa Y, Tanoue A, Oikawa R, Kawahara Y, Kiyono Y, Adachi T, Tanaka T, Kuwaki T, Mori T, Takeo S, Okamura H, and Tsujimoto G. V1a vasopressin receptors maintain normal blood pressure by regulating circulating blood volume and baroreflex sensitivity. *Proceedings of the National Academy of Sciences of the United States of America* 103: 7807-7812, 2006.
49. Kubo T, Yamaguchi H, Tsujimura M, Hagiwara Y, and Fukumori R. An angiotensin system in the anterior hypothalamic area anterior is involved in the maintenance of hypertension in spontaneously hypertensive rats. *Brain research bulletin* 52: 291-296, 2000.
50. Kubo T, Yamaguchi H, Tsujimura M, Hagiwara Y, and Fukumori R. Blockade of angiotensin receptors in the anterior hypothalamic preoptic area lowers blood pressure in DOCA-salt hypertensive rats. *Hypertension research: official journal of the Japanese Society of Hypertension* 23: 109-118, 2000.
51. Laragh J H. Biochemical profiling and the natural history of hypertensive diseases: low-renin essential hypertension, a benign condition. *Circulation* 44: 971-974, 1971.
52. Levine R J, Lam C, Qian C, Yu K F, Maynard S E, Sachs B P, Sibai B M, Epstein F H, Romero R, Thadhani R, and Karumanchi S A. Soluble endoglin and other circulating antiangiogenic factors in preeclampsia. *The New England journal of medicine* 355: 992-1005, 2006.
53. Littlejohn N K, Siel R B, Jr., Ketsawatsomkron P, Pelham C J, Pearson N A, Hilzendeger A M, Buehrer B A, Weidemann B J, Li H, Davis D R, Thompson A P, Liu X, Cassell M D, Sigmund C D, and Grobe J L. Hypertension in mice with transgenic activation of the brain renin-angiotensin system is vasopressin dependent. *American journal of physiology Regulatory, integrative and comparative physiology* 304: R818-828, 2013.
54. Livak K J and Schmittgen T D. Analysis of relative gene expression data using real-time quantitative PCR and the 2(-Delta Delta C(T)) Method. *Methods (San Diego, Calif.)* 25: 402-408, 2001.
55. Lykke J A, Langhoff-Roos J, Sibai B M, Funai E F, Triche E W, and Paidas M J. Hypertensive pregnancy disorders and subsequent cardiovascular morbidity and type 2 diabetes mellitus in the mother. *Hypertension* 53: 944-951, 2009.
56. Magnussen E B, Vatten L J, Smith G D, and Romundstad P R. Hypertensive disorders in pregnancy and subsequently measured cardiovascular risk factors. *Obstetrics and gynecology* 114: 961-970, 2009.
57. Matsuguchi H and Schmid P G. Acute interaction of vasopressin and neurogenic mechanisms in DOC-salt hypertension. *The American journal of physiology* 242: H37-43, 1982.
58. Mattsson R, Sulila P, Bernadotte F, and Mattsson A. Allopregnancy in B-cell deprived C57/BL mice—an investigation focusing on the relationship between survival of the fetuses and anti-paternal immune activity of the mothers. *Developmental and comparative immunology* 12: 167-176, 1988.
59. Mayorov D N and Head G A. AT1 receptors in the RVLM mediate pressor responses to emotional stress in rabbits. *Hypertension* 41: 1168-1173, 2003.
60. Mohring J and Mohring B. Reevaluation of DOCA escape phenomenon. *The American journal of physiology* 223: 1237-1245, 1972.
61. Morimoto S, Cassell M D, and Sigmund C D. The brain renin-angiotensin system in transgenic mice carrying a highly regulated human renin transgene. *Circulation research* 90: 80-86, 2002.
62. Neves M F, Virdis A, and Schiffrin E L. Resistance artery mechanics and composition in angiotensin II-infused rats: effects of aldosterone antagonism. *Journal of hypertension* 21: 189-198, 2003.

63. Northcott C A, Watts S, Chen Y, Morris M, Chen A, and Haywood J R. Adenoviral inhibition of AT1a receptors in the paraventricular nucleus inhibits acute increases in mean arterial blood pressure in the rat. *American journal of physiology Regulatory, integrative and comparative physiology* 299: R1202-1211, 2010.

64. Odibo A O, Rada C C, Cahill A G, Goetzinger K R, Tuuli M G, Odibo L, Macones G A, and England S K. First-trimester serum soluble fms-like tyrosine kinase-1, free vascular endothelial growth factor, placental growth factor and uterine artery Doppler in preeclampsia. *Journal of perinatology: official journal of the California Perinatal Association* 33: 670-674, 2013.

65. Oparil S, Yang R H, Jin H G, Chen S J, Meng Q C, Berecek K H, and Wyss J M. Role of anterior hypothalamic angiotensin II in the pathogenesis of salt sensitive hypertension in the spontaneously hypertensive rat. *The American journal of the medical sciences* 307 Suppl 1: S26-37, 1994.

66. Os I, Kjeldsen S E, Skjoto J, Westheim A, Lande K, Aakesson I, Frederichsen P, Leren P, Hjermann I, and Eide I K. Increased plasma vasopressin in low renin essential hypertension. *Hypertension* 8: 506-513, 1986.

67. Padfield P L, Brown J J, Lever A F, Morton J J, and Robertson J I. Blood pressure in acute and chronic vasopressin excess: studies of malignant hypertension and the syndrome of inappropriate antidiuretic hormone secretion. *The New England journal of medicine* 304: 1067-1070, 1981.

68. Papageorghiou A T, To M S, Yu C K, and Nicolaides K H. Repeatability of measurement of uterine artery pulsatility index using transvaginal color Doppler. *Ultrasound in obstetrics & gynecology: the official journal of the International Society of Ultrasound in Obstetrics and Gynecology* 18: 456-459, 2001.

69. Park C G and Leenen F H. Effects of centrally administered losartan on deoxycorticosterone-salt hypertension rats. *Journal of Korean medical science* 16: 553-557, 2001.

70. Phillips M I. Angiotensin in the brain. *Neuroendocrinology* 25: 354-377, 1978.

71. Poon L C, Kametas N A, Chelemen T, Leal A, and Nicolaides K H. Maternal risk factors for hypertensive disorders in pregnancy: a multivariate approach. *Journal of human hypertension* 24: 104-110, 2010.

72. Poon L C, Karagiannis G, Leal A, Romero X C, and Nicolaides K H. Hypertensive disorders in pregnancy: screening by uterine artery Doppler imaging and blood pressure at 11-13 weeks. *Ultrasound in obstetrics & gynecology: the official journal of the International Society of Ultrasound in Obstetrics and Gynecology* 34: 497-502, 2009.

73. Ramsay D S. Effects of circulating angiotensin II on the brain. In: *Frontiers in Neuroendocrinology*, edited by Ganong W F and Martini L. New York: Raven, 1982, p. 263-285.

74. Romero R, Mazor M, and Tartakovsky B. Systemic administration of interleukin-1 induces preterm parturition in mice. *American journal of obstetrics and gynecology* 165: 969-971, 1991.

75. Russell J A and Walley K R. Vasopressin and its immune effects in septic shock. *Journal of innate immunity* 2: 446-460, 2010.

76. Sakai K, Agassandian K, Morimoto S, Sinnayah P, Cassell M D, Davisson R L, and Sigmund C D. Local production of angiotensin II in the subfornical organ causes elevated drinking. *The Journal of clinical investigation* 117: 1088-1095, 2007.

77. Salim S, Sinnarajah S, Kehrl J H, and Dessauer C W. Identification of RGS2 and type V adenylyl cyclase interaction sites. *The Journal of biological chemistry* 278: 15842-15849, 2003.

78. Santillan M K, Santillan D A, Sigmund C D, and Hunter S K. From molecules to medicine: a future cure for preeclampsia? *Drug news & perspectives* 22: 531-541, 2009.

79. Schinke M, Baltatu O, Bohm M, Peters J, Rascher W, Bricca G, Lippoldt A, Ganten D, and Bader M. Blood pressure reduction and diabetes insipidus in transgenic rats deficient in brain angiotensinogen. *Proceedings of the National Academy of Sciences of the United States of America* 96: 3975-3980, 1999.

80. Semplicini A, Lenzini L, Sartori M, Papparella I, Cabo L A, Pagnin E, Strapazzon G, Benna C, Costa R, Avogaro A, Ceolotto G, and Pessina A C. Reduced expression of regulator of G-protein signaling 2 (RGS2) in hypertensive patients increases calcium mobilization and ERK1/2 phosphorylation induced by angiotensin II. *Journal of hypertension* 24: 1115-1124, 2006.

81. Shah D M. The role of RAS in the pathogenesis of preeclampsia. *Current hypertension reports* 8: 144-152, 2006.

82. Shi P, Diez-Freire C, Jun J Y, Qi Y, Katovich M J, Li Q, Sriramula S, Francis J, Sumners C, and Raizada M K. Brain microglial cytokines in neurogenic hypertension. *Hypertension* 56: 297-303, 2010.

83. Siljee J E, Wortelboer E J, Koster M P, Imholz S, Rodenburg W, Visser G H, de Vries A, Schielen P C, and Pennings J L. Identification of interleukin-1 beta, but no other inflammatory proteins, as an early onset pre-eclampsia biomarker in first trimester serum by bead-based multiplexed immunoassays. *Prenatal diagnosis* 33: 1183-1188, 2013.

84. Sinn P L, Zhang X, and Sigmund C D. JG cell expression and partial regulation of a human renin genomic transgene driven by a minimal renin promoter. *The American journal of physiology* 277: F634-642, 1999.

85. Steegers E A, von Dadelszen P, Duvekot J J, and Pijnenborg R. Pre-eclampsia. *Lancet* 376: 631-644, 2010.

86. Sulila P, Holmdahl R, Hansson I, Bernadotte F, Mattsson A, and Mattsson R. An investigation of allogeneic pregnancy in multiparous mice subjected to in vivo depletion of CD8 (Ly2)-positive lymphocytes by monoclonal antibody treatment. *Journal of reproductive immunology* 14: 235-245, 1988.

87. Sun X, Kaltenbronn K M, Steinberg T H, and Blumer K J. RGS2 is a mediator of nitric oxide action on blood pressure and vasoconstrictor signaling. *Molecular pharmacology* 67: 631-639, 2005.

88. Sun Z, Cade R, and Morales C. Role of central angiotensin II receptors in cold-induced hypertension. *American journal of hypertension* 15: 85-92, 2002.

89. Szczepanska-Sadowska E, Paczwa P, Lon S, and Ganten D. Increased pressor function of central vasopressinergic system in hypertensive renin transgenic rats. *Journal of hypertension* 16: 1505-1514, 1998.

90. Szinnai G, Morgenthaler N G, Berneis K, Struck J, Muller B, Keller U, and Christ-Crain M. Changes in plasma copeptin, the c-terminal portion of arginine vasopressin during water deprivation and excess in healthy subjects. *The Journal of clinical endocrinology and metabolism* 92: 3973-3978, 2007.

91. Takimoto E, Koitabashi N, Hsu S, Ketner E A, Zhang M, Nagayama T, Bedj a D, Gabrielson K L, Blanton R, Siderovski D P, Mendelsohn M E, and Kass D A. Regulator of G protein signaling 2 mediates cardiac compensation to pressure overload and antihypertrophic effects of PDE5 inhibition in mice. *The Journal of clinical investigation* 119: 408-420, 2009.

92. Tang K M, Wang G R, Lu P, Karas R H, Aronovitz M, Heximer S P, Kaltenbronn K M, Blumer K J, Siderovski D P, Zhu Y, and Mendelsohn M E. Regulator of G-protein signaling-2 mediates vascular smooth muscle relaxation and blood pressure. *Nature medicine* 9: 1506-1512, 2003.

93. Thadhani R, Kisner T, Hagmann H, Bossung V, Noack S, Schaarschmidt W, Jank A, Kribs A, Comely O A, Kreyssig C, Hemphill L, Rigby A C, Khedkar S, Lindner T H, Mallmann P, Stepan H, Karumanchi S A, and Benzing T. Pilot study of extracorporeal removal of soluble fms-like tyrosine kinase 1 in preeclampsia. *Circulation* 124: 940-950, 2011.

94. Trinder D, Phillips P A, Stephenson J M, Risvanis J, Aminian A, Adam W, Cooper M, and Johnston C I. Vasopressin V1 and V2 receptors in diabetes mellitus. *The American journal of physiology* 266: E217-223, 1994.

95. Tsang S, Woo A Y, Zhu W, and Xiao R P. Deregulation of RGS2 in cardiovascular diseases. *Frontiers in bioscience (Scholar edition)* 2: 547-557, 2010.

96. Wrobel L J, Dupre A, and Raggenbass M. Excitatory action of vasopressin in the brain of the rat: role of cAMP signaling. *Neuroscience* 172: 177-186, 2011.

97. Wu C S, Nohr E A, Bech B H, Vestergaard M, Catov J M, and Olsen J. Health of children born to mothers who had preeclampsia: a population-based cohort study. *American journal of obstetrics and gynecology* 201: 269.e261-269.e210, 2009.

98. Wu C S, Sun Y, Vestergaard M, Christensen J, Ness R B, Haggerty C L, and Olsen J. Preeclampsia and risk for epilepsy in offspring. *Pediatrics* 122: 1072-1078, 2008.

99. Yamamoto J, Yamane Y, Umeda Y, Yoshioka T, Nakai M, and Ikeda M. Cardiovascular hemodynamics and vasopressin blockade in DOCA-salt hypertensive rats. *Hypertension* 6: 397-407, 1984.

100. Yang C R, Phillips M I, and Renaud L P. Angiotensin II receptor activation depolarizes rat supraoptic neurons in vitro. *The American journal of physiology* 263: R1333-1338, 1992.

101. Yang J, Kamide K, Kokubo Y, Takiuchi S, Tanaka C, Banno M, Miwa Y, Yoshii M, Horio T, Okayama A, Tomoike H, Kawano Y, and Miyata T. Genetic variations of regulator of G-protein signaling 2 in hypertensive patients and in the general population. *Journal of hypertension* 23: 1497-1505, 2005.

102. Yang R H, Jin H, Wyss J M, and Oparil S. Depressor effect of blocking angiotensin subtype 1 receptors in anterior hypothalamus. *Hypertension* 19: 475-481, 1992.

103. Ye S, Zhong H, Duong V N, and Campese V M. Losartan reduces central and peripheral sympathetic nerve activity in a rat model of neurogenic hypertension. *Hypertension* 39: 1101-1106, 2002.

104. Zhang W, Anger T, Su J, Hao J, Xu X, Zhu M, Gach A, Cui L, Liao R, and Mende U. Selective loss of fine tuning of Gq/11 signaling by RGS2 protein exacerbates cardiomyocyte hypertrophy. *The Journal of biological chemistry* 281: 5811-5820, 2006.

105. Zhang X, Hense H W, Riegger G A, and Schunkert H. Association of arginine vasopressin and arterial blood pressure in a population-based sample. *Journal of hypertension* 17: 319-324, 1999.

106. Zicha J, Kunes J, Lebl M, Pohlova I, Slaninova J, and Jelinek J. Antidiuretic and pressor actions of vasopressin in age-dependent DOCA-salt hypertension. *The American journal of physiology* 256: R138-145, 1989.

107. Zimmerman M C, Lazartigues E, Sharma R V, and Davisson R L. Hypertension caused by angiotensin II infusion involves increased superoxide production in the central nervous system. *Circulation research* 95: 210-216, 2004.

108. Zulfikaroglu E, Islimye M, Tonguc E A, Payasli A, Isman F, Var T, and Danisman N. Circulating levels of copeptin, a novel biomarker in pre-eclampsia. *The journal of obstetrics and gynaecology research* 37: 1198-1202, 2011.

---

What is claimed is:

1. A method of treating preeclampsia in a subject in need thereof, comprising administering to the subject a therapeutically effective amount of an arginine vasopressin (AVP) receptor antagonist, wherein the AVP receptor antagonist comprises one or more vaptan drugs.

2. The method of claim 1, wherein the one or more vaptan drugs inhibit the action of AVP on its receptors.

3. The method of claim 2, wherein the AVP receptors comprise V1A, V2, and V1B.

4. A method of treating preeclampsia in a subject in need thereof, comprising:
administering to the subject a therapeutically effective amount of a pharmaceutical compound,
wherein the pharmaceutical compound is tetrahydrobiopterin (BH4) or a chemically related compound.

5. The method of claim 1, wherein the vaptan drugs comprise conivaptan, tolvaptan, relcovaptan, and combinations thereof.

6. The method of claim 1, wherein the administering of the therapeutically effective amount of the one or more vaptan drugs reduces the blood pressure of the subject.

7. The method of claim 4 further comprising administering to the subject a therapeutically effective amount of an AVP receptor antagonist.

8. The method of claim 7, wherein the AVP receptor antagonist comprises one or more vaptan drugs.

9. The method of claim 8, wherein the one or more vaptan drugs comprise conivaptan, tolvaptan, relcovaptan, and combinations thereof.

10. The method of claim 9, wherein administration of the therapeutically effective amount of the one or more vaptan drugs reduces the blood pressure of the subject.

11. The method of claim 1, wherein the therapeutically effective amount of the AVP receptor antagonist is administered in the first trimester of pregnancy.

12. The method of claim 4, wherein the therapeutically effective amount of the pharmaceutical compound is administered in the first trimester of pregnancy.

* * * * *

UNITED STATES PATENT AND TRADEMARK OFFICE
CERTIFICATE OF CORRECTION

PATENT NO. : 9,937,182 B2
APPLICATION NO. : 14/766574
DATED : April 10, 2018
INVENTOR(S) : Grobe et al.

Page 1 of 1

It is certified that error appears in the above-identified patent and that said Letters Patent is hereby corrected as shown below:

In the Specification

At Column 1, Line 16:
Under the Cross Reference To Related Applications paragraph please insert:
-- STATEMENT REGARDING FEDERALLY SPONSORED RESEARCH OR DEVELOPMENT
This invention was made with government support under HD000849 and HL098276 awarded by the National Institutes of Health. The government has certain rights in the invention. --

Signed and Sealed this
Fifteenth Day of May, 2018

Andrei Iancu
*Director of the United States Patent and Trademark Office*

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: SYBR188 green assays NKCC2 FORWARD

<400> SEQUENCE: 1
ccatggtaac ctctatcact gggt                                          24

<210> SEQ ID NO 2
<211> LENGTH: 24
<212> TYPE: DNA
<213> ORGANISM: Artificial Sequence
<220> FEATURE:
<223> OTHER INFORMATION: SYBR188 green assays NKCC2 reverse

<400> SEQUENCE: 2
tcaagcctat tgacccaccg aact                                          24
```

```
<210> SEQ ID NO 3
<211> LENGTH: 24
<212> TYPE: DNA
<213> ORGANISM: Artificial Sequence
<220> FEATURE:
<223> OTHER INFORMATION: SYBR188 green assays NCC FORWARD

<400> SEQUENCE: 3
aagtcgggtg gcacctattt cctt                                          24

<210> SEQ ID NO 4
<211> LENGTH: 24
<212> TYPE: DNA
<213> ORGANISM: Artificial Sequence
<220> FEATURE:
<223> OTHER INFORMATION: SYBR188 green assays NCC reverse

<400> SEQUENCE: 4
ttacggtttc tgcaaagccc acag                                          24

<210> SEQ ID NO 5
<211> LENGTH: 24
<212> TYPE: DNA
<213> ORGANISM: Artificial Sequence
<220> FEATURE:
<223> OTHER INFORMATION: SYBR188 green assays NHE3 FORWARD

<400> SEQUENCE: 5
tcctctcagc cattgaggac atct                                          24

<210> SEQ ID NO 6
<211> LENGTH: 24
<212> TYPE: DNA
<213> ORGANISM: Artificial Sequence
<220> FEATURE:
<223> OTHER INFORMATION: SYBR188 green assays NHE3 REVERSE

<400> SEQUENCE: 6
actttgctga ggaacttccg gtca                                          24

<210> SEQ ID NO 7
<211> LENGTH: 24
<212> TYPE: DNA
<213> ORGANISM: Artificial Sequence
<220> FEATURE:
<223> OTHER INFORMATION: SYBR188 green assays ENaC -1 forward

<400> SEQUENCE: 7
acaatggttt gtccctgaca ctgc                                          24

<210> SEQ ID NO 8
<211> LENGTH: 24
<212> TYPE: DNA
<213> ORGANISM: Artificial Sequence
<220> FEATURE:
<223> OTHER INFORMATION: SYBR188 green assays ENaC -1 REVERSE

<400> SEQUENCE: 8
tcacgttgaa gccaccatca tcca                                          24

<210> SEQ ID NO 9
<211> LENGTH: 24
<212> TYPE: DNA
<213> ORGANISM: Artificial Sequence
<220> FEATURE:
<223> OTHER INFORMATION: SYBR188 green assays ENaC-2 FORWARD
```

```
<400> SEQUENCE: 9
tctgccaacc ctgggactga attt                                              24

<210> SEQ ID NO 10
<211> LENGTH: 24
<212> TYPE: DNA
<213> ORGANISM: Artificial Sequence
<220> FEATURE:
<223> OTHER INFORMATION: SYBR188 green assays ENaC-2 REVERSE

<400> SEQUENCE: 10
tggcatagat gccctcctct ctaa                                              24

<210> SEQ ID NO 11
<211> LENGTH: 24
<212> TYPE: DNA
<213> ORGANISM: Artificial Sequence
<220> FEATURE:
<223> OTHER INFORMATION: SYBR188 green assays ENaC-3 FORWARD

<400> SEQUENCE: 11
gccaatcagt gtgcaagcaa tcct                                              24

<210> SEQ ID NO 12
<211> LENGTH: 24
<212> TYPE: DNA
<213> ORGANISM: Artificial Sequence
<220> FEATURE:
<223> OTHER INFORMATION: SYBR188 green assays ENaC-3 REVERSE

<400> SEQUENCE: 12
ttatttgctg gctttggtcc cagg                                              24

<210> SEQ ID NO 13
<211> LENGTH: 24
<212> TYPE: DNA
<213> ORGANISM: Artificial Sequence
<220> FEATURE:
<223> OTHER INFORMATION: SYBR188 green assays NKA-1 forward

<400> SEQUENCE: 13
tgaagctgac accacggaga atca                                              24

<210> SEQ ID NO 14
<211> LENGTH: 23
<212> TYPE: DNA
<213> ORGANISM: Artificial Sequence
<220> FEATURE:
<223> OTHER INFORMATION: SYBR188 green assays NKA-1 REVERSE

<400> SEQUENCE: 14
tgccgcttaa gaataggcag gtt                                               23

<210> SEQ ID NO 15
<211> LENGTH: 24
<212> TYPE: DNA
<213> ORGANISM: Artificial Sequence
<220> FEATURE:
<223> OTHER INFORMATION: SYBR188 green assays V2R FORWARD

<400> SEQUENCE: 15
tgtgattgtc tacgtgctgt gctg                                              24

<210> SEQ ID NO 16
<211> LENGTH: 24
```

```
<212> TYPE: DNA
<213> ORGANISM: Artificial Sequence
<220> FEATURE:
<223> OTHER INFORMATION: SYBR188 green assays V2R REVERSE

<400> SEQUENCE: 16
gggttggtac agctgttaag gcta                                          24

<210> SEQ ID NO 17
<211> LENGTH: 24
<212> TYPE: DNA
<213> ORGANISM: Artificial Sequence
<220> FEATURE:
<223> OTHER INFORMATION: SYBR188 green assays AQP1 FORWARD

<400> SEQUENCE: 17
ctgggcattg agatcattgg cact                                          24

<210> SEQ ID NO 18
<211> LENGTH: 24
<212> TYPE: DNA
<213> ORGANISM: Artificial Sequence
<220> FEATURE:
<223> OTHER INFORMATION: SYBR188 green assays AQP1 REVERSE

<400> SEQUENCE: 18
tgataccgca gccagtgtag tcaa                                          24

<210> SEQ ID NO 19
<211> LENGTH: 24
<212> TYPE: DNA
<213> ORGANISM: Artificial Sequence
<220> FEATURE:
<223> OTHER INFORMATION: SYBR188 green assays AQP2 FORWARD

<400> SEQUENCE: 19
tagccctgct ctctccattg gttt                                          24

<210> SEQ ID NO 20
<211> LENGTH: 24
<212> TYPE: DNA
<213> ORGANISM: Artificial Sequence
<220> FEATURE:
<223> OTHER INFORMATION: SYBR188 green assays AQP2 REVERSE

<400> SEQUENCE: 20
aaacttgcca gtgacaactg ctgg                                          24

<210> SEQ ID NO 21
<211> LENGTH: 24
<212> TYPE: DNA
<213> ORGANISM: Artificial Sequence
<220> FEATURE:
<223> OTHER INFORMATION: SYBR188 green assays AQP3 FORWARD

<400> SEQUENCE: 21
atggtggctt cctcaccatc aact                                          24

<210> SEQ ID NO 22
<211> LENGTH: 24
<212> TYPE: DNA
<213> ORGANISM: Artificial Sequence
<220> FEATURE:
<223> OTHER INFORMATION: SYBR188 green assays AQP3 REVERSE

<400> SEQUENCE: 22
```
aggaagcaca ttgcgaaggt caca                                          24

<210> SEQ ID NO 23
<211> LENGTH: 24
<212> TYPE: DNA
<213> ORGANISM: Artificial Sequence
<220> FEATURE:
<223> OTHER INFORMATION: SYBR188 green assays AQP4 FORWARD

<400> SEQUENCE: 23
tgccagctgt gattccaaac gaac                                          24

<210> SEQ ID NO 24
<211> LENGTH: 24
<212> TYPE: DNA
<213> ORGANISM: Artificial Sequence
<220> FEATURE:
<223> OTHER INFORMATION: SYBR188 green assays AQP4 REVERSE

<400> SEQUENCE: 24
tcccatgata actgcgggtc caaa                                          24

<210> SEQ ID NO 25
<211> LENGTH: 24
<212> TYPE: DNA
<213> ORGANISM: Artificial Sequence
<220> FEATURE:
<223> OTHER INFORMATION: SYBR188 green assays PGES FORWARD

<400> SEQUENCE: 25
tttgcaacaa gtactggccc atgc                                          24

<210> SEQ ID NO 26
<211> LENGTH: 24
<212> TYPE: DNA
<213> ORGANISM: Artificial Sequence
<220> FEATURE:
<223> OTHER INFORMATION: SYBR188 green assays PGES REVERSE

<400> SEQUENCE: 26
tgttcggtac acgttgggag agat                                          24

<210> SEQ ID NO 27
<211> LENGTH: 24
<212> TYPE: DNA
<213> ORGANISM: Artificial Sequence
<220> FEATURE:
<223> OTHER INFORMATION: SYBR188 green assays UT1-A FORWARD

<400> SEQUENCE: 27
cactggcgac atgaaggaat gcaa                                          24

<210> SEQ ID NO 28
<211> LENGTH: 26
<212> TYPE: DNA
<213> ORGANISM: Artificial Sequence
<220> FEATURE:
<223> OTHER INFORMATION: SYBR188 green assays UT1-A REVERSE

<400> SEQUENCE: 28
gggttgttga caaacatcac ctgagc                                        26

<210> SEQ ID NO 29
<211> LENGTH: 24
<212> TYPE: DNA
<213> ORGANISM: Artificial Sequence

```
<220> FEATURE:
<223> OTHER INFORMATION: B-actin Forward

<400> SEQUENCE: 29
catcctcttc ctccctggag aaga                                          24

<210> SEQ ID NO 30
<211> LENGTH: 27
<212> TYPE: DNA
<213> ORGANISM: Artificial Sequence
<220> FEATURE:
<223> OTHER INFORMATION: B-actin Reverse

<400> SEQUENCE: 30
acaggattcc atacccaaga aggaagg                                       27
```